United States Patent
Yang et al.

(10) Patent No.: US 7,462,594 B2
(45) Date of Patent: Dec. 9, 2008

(54) PEPTIDE-LIKE COMPOUNDS THAT INHIBIT CORONAVIRAL 3CL AND FLAVIVIRIDAE VIRAL PROTEASES

(75) Inventors: Syaulan Yang, Taipei (TW); Jen-Dar Wu, Chiayi County (TW); Feng-Yih Su, Pingtung County (TW); Chun-Wei Kuo, Taipei (TW); Wen-Chang Chen, Taipei (TW); Ming-Chu Hsu, Glendora, CA (US); Yibin Xiang, Acton, MA (US); Ching-Cheng Wang, Taipei (TW); Shao-Ying Liao, Taipei (TW)

(73) Assignee: Taigen Biotechnology Co., Ltd., Taipei (TW)

( * ) Notice: Subject to any disclaimer, the term of this patent is extended or adjusted under 35 U.S.C. 154(b) by 415 days.

(21) Appl. No.: 11/067,264

(22) Filed: Feb. 25, 2005

(65) Prior Publication Data

US 2005/0143320 A1    Jun. 30, 2005

Related U.S. Application Data

(63) Continuation-in-part of application No. 11/024,929, filed on Dec. 29, 2004, now Pat. No. 7,304,088.

(60) Provisional application No. 60/533,779, filed on Dec. 31, 2003.

(51) Int. Cl.
  *A61K 38/00*  (2006.01)
  *A61K 31/40*  (2006.01)
  *A01N 37/18*  (2006.01)
  *A01N 43/36*  (2006.01)

(52) U.S. Cl. ............................. 514/2; 514/11; 514/424

(58) Field of Classification Search ................. 514/424, 514/2, 11
See application file for complete search history.

(56) References Cited

U.S. PATENT DOCUMENTS

| | | | |
|---|---|---|---|
| 5,856,530 A | 1/1999 | Webber et al. | |
| 5,962,487 A | 10/1999 | Webber et al. | ............... 514/378 |
| 6,214,799 B1 | 4/2001 | Webber et al. | |
| 6,355,807 B1 | 3/2002 | Tian et al. | |
| 6,362,166 B1 | 3/2002 | Webber et al. | |
| 6,514,997 B2 | 2/2003 | Dragovich et al. | |
| 6,531,452 B1 | 3/2003 | Dragovich et al. | |
| 6,534,530 B1 | 3/2003 | Dragovich et al. | |
| 2001/0047006 A1 | 11/2001 | Dragovich et al. | |
| 2002/0006943 A1 | 1/2002 | Johnson, Jr. et al. | |
| 2002/0133020 A1 | 9/2002 | Tian et al. | |
| 2006/0014821 A1* | 1/2006 | He et al. | ..................... 514/424 |

FOREIGN PATENT DOCUMENTS

WO    WO 97/43305    11/1997

WO    WO 99/57135    11/1999

OTHER PUBLICATIONS

Dragovich et al., "Structure-Based Design of Irreversible, Tripeptidyl Human Rhinovirus 3C Protease Inhibitors Containing N-Methyl Amino Acids", Bioorganic & Medicinal Chemistry Letters, 9 (1999) 2189-2194.
Dragovich et al., "Structure-Based Design of Ketone-Containing, Tripeptidyl Human Rhinovirus 3C Protease Inhibitors", Bioorganic & Medicinal Chemistry Letters, 10 (2000) 45-48.
Dragovich et al., "Solid-phase Synthesis of Irreversible Human Rhinovirus 3C Protease Inhibitors. Part 1: Optimization of Tripeptides Incorporating N-terminal Amides", Bioorganic & Medicinal Chemistry 7 (1999) 589-598.
Dragovich et al., "Structure-Based Design, Synthesis, and Biological Evaluation of Irreversible Human Rhinovirus 3C Protease Inhibitors. Part 7: Structure—Activity Studies of Bicyclic 2-Pyridone-Containing Peptidomimetics", Bioorganic & Medicinal Chemistry Letters 12 (2002) 733-738.
Dragovich et al., "Synthesis of an Optically Active, Bicyclic 2-Pyridone Dipeptide Mimetic", J. Org. Chem. 2002, 67,741-746.
Dragovich et al., "Structure-Based Design, Synthesis, and Biological Evaluation of Irreversible Human Rhinovirus 3C Protease Inhibitors. 1. Michael Acceptor Structure—Activity Studies", J. Med. Chem. 1998, 41, 2806-2818.
Dragovich et al., "Structure-Based Design, Synthesis, and Biological Evaluation of Irreversible Human Rhinovirus 3C Protease Inhibitors. 2. Peptide Structure—Activity Studies", J. Med. Chem. 1998, 41, 2819-2834.
Dragovich et al., "Structure-Based Design, Synthesis, and Biological Evaluation of Irreversible Human Rhinovirus 3C Protease Inhibitors. 3. Structure—Activity Studies of Ketomethylene-Containing Peptidomimetics", J. Med. Chem. 1999, 42, 1203-1212.
Dragovich et al., "Structure-Based Design, Synthesis, and Biological Evaluation of Irreversible Human Rhinovirus 3C Protease Inhibitors. 4. Incorporation of $P_1$ Lactam Moieties as L-Glutamine Replacements", J. Med. Chem. 1999, 42, 1213-1224.
Dragovich et al., "Structure-Based Design, Synthesis, and Biological Evaluation of Irreversible Human Rhinovirus 3C Protease Inhibitors. 6. Structure—Activity Studies of Orally Bioavailable, 2-Pydridone-Containing Peptidomimetics", J. Med. Chem. 2002, 45, 1607-1623.

(Continued)

*Primary Examiner*—Frederick Krass
*Assistant Examiner*—Benjamin Packard
(74) *Attorney, Agent, or Firm*—Occhiuti Rohlicek & Tsao LLP

(57) ABSTRACT

This invention relates to treating an infection with a virus using protease inhibitors. Examples of the protease inhibitors include compounds of formula (II). Each variable is defined in the specification.

(II)

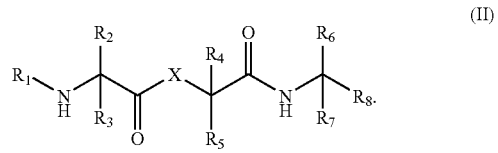

2 Claims, No Drawings

OTHER PUBLICATIONS

Dragovich et al., "Structure-Based Design, Synthesis, and Biological Evaluation of Irreversible Human Rhinovirus 3C Protease Inhibitors. 8. Pharmacological Optimization of Orally Bioavailable 2-Pyridone-Containing Peptidomimetics", J. Med. Chem. 2003, 46, 4572-4585.

Johnson et al., "Structure-Based Design of a Parallel Synthetic Array Directed Toward the Discovery of Irreversible Inhibitors of Human Rhinovirus 3C Protease", J. Med. Chem. 2002, 45, 2016-2023.

Matthews et al., "Structure-assisted design of mechanism-based irreversible inhibitors of human rhinovirus 3C protease with potent antiviral activity against multiple rhinovirus serotypes", Proc. Natl. Acad. Sci USA, vol. 96, pp. 11000-11007, Sep. 1999.

Reich et al., "Substituted Benzamide Inhibitors of Human Rhinovirus 3C Protease: Structure-Based Design, Synthesis, and Biological Evaluation", J. Med. Chem. 2000, 43, 1670-1683.

Tian et al., "An efficient synthesis of a key intermediate for the preparation of the rhinovirus protease inhibitor AG7088 via asymmetric dianionic cyanomethylation of N-Boc-L-(+)-glutamic acid dimethyl ester", Tetrahedron Letters, 42, 2001, 6807-6809.

Wang, "Design of rhinovirus protease inhibitors for the treatment of the common cold", Drugs of the Future, 2000, 25(3):279-286.

Webber et al., "Design and Synthesis of Irreversible Depsipeptidyl Human Rhinovirus 3C Protease Inhibitors", Bioorganic & Medicinal Chemistry Letters, 11, 2001, 2683-2686.

Caulfield et al., "Parallel Solid-Phase Synthesis of Peptidyl Michael Acceptors", J. Comb. Chem. 2:600-603, 2000.

Jenwitheesuk et al., "Identifying Inhibitors of the SARS Coronavirus Proteinase", Bioorganic & Medicinal Chemistry Letters 13:3989-3992, 2003.

* cited by examiner

PEPTIDE-LIKE COMPOUNDS THAT INHIBIT CORONAVIRAL 3CL AND FLAVIVIRIDAE VIRAL PROTEASES

CROSS REFERENCE TO RELATED APPLICATIONS

This application is a continuation-in-part application of U.S. Utility application Ser. No. 11/024,929, filed Dec. 29, 2004, now U.S. Pat. No. 7,304,088 which in turn claims priority to U.S. Provisional Application Ser. No. 60/533,779, filed Dec. 31, 2003. The contents of both applications are hereby incorporated by reference.

BACKGROUND

Coronavirus is a family of viruses that have the appearance of a corona when viewed under a microscope. Members of the coronavirus family can cause hepatitis in mice, gastroenteritis in pigs, and respiratory infections in birds and humans. Coronavirus was first isolated from chickens in 1937 by Beaudette and Hudson. In 1965, Tyrrell and Bynoe used cultures of human ciliated embryonic trachea to propagate the first human coronavirus in vitro.

Among the more than 30 strains of coronavirus isolated so far, three or four infect humans. For example, the severe acute respiratory syndrome, a newly emerged infectious disease, is associated with a novel coronavirus (Ksiazek et al., New England Journal Medicine, 2003, 348(20): 1953-1966). This life-threatening respiratory disease caused worldwide outbreaks in 2003. Vaccines and drugs against severe acute respiratory syndrome virus are being vigorously sought. Nevertheless, the progress is rather slow due to safety concerns. Thus, there exists a need to develop drugs that are effective in treating infections with coronaviruses, as well as infections with other viruses.

SUMMARY

This invention is based on the unexpected discovery that certain peptide-like compounds are effective in treating viral infections by inhibiting viral proteases (e.g., coronaviral 3CL proteases or flaviviridae viral proteases).

In one aspect, this invention features a method for treating an infection with a virus. The method includes administering to a subject in need thereof an effective amount of a compound of formula (I):

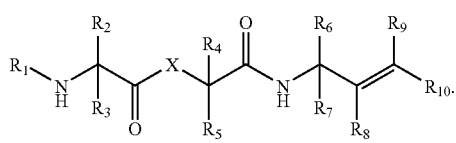

(I)

In this formula, X is $N(R_{a1})$, O, or $CH_2$; or X and one of $R_2$ and $R_3$, together with the atom or atoms to which they are bonded, are $C_3$-$C_{20}$ heterocycloalkyl; in which $R_{a1}$ is H or $C_1$-$C_{15}$ alkyl; $R_1$ is H, $C_1$-$C_{15}$ alkyl, $C_3$-$C_{20}$ cycloalkyl, $C_3$-$C_{20}$ heterocycloalkyl, heteroaryl, aryl, $C(O)R_{b1}$, $CO_2R_{b1}$, $C(O)NR_{b1}R_{b2}$, $C(O)$—$N(R_{b1})$—$OR_{b2}$, $C(S)R_{b1}$, $C(S)NR_{b1}R_{b2}$, $S(O)R_{b1}$, $SO_2R_{b1}$, $S(O)NR_{b1}R_{b2}$, $S(O)$—$N(R_{b1})$—$OR_{b2}$, $SO_2NR_{b1}R_{b2}$, or $SO_3R_{b1}$; in which each of $R_{b1}$ and $R_{b2}$, independently, is H, $C_1$-$C_{15}$ alkyl, $C_3$-$C_{20}$ cycloalkyl, $C_3$-$C_{20}$ heterocycloalkyl, heteroaryl, or aryl; each of $R_2$ and $R_3$, independently, is H, $C_1$-$C_{15}$ alkyl, $C_3$-$C_{20}$ cycloalkyl, $C_3$-$C_{20}$ heterocycloalkyl, heteroaryl, aryl, $OR_{c1}$, $SR_{c1}$, or $NR_{c1}R_{c2}$; or X and one of $R_2$ and $R_3$, together with the atom or atoms to which they are bonded, are $C_3$-$C_{20}$ heterocycloalkyl; in which each of $R_{c1}$ and $R_{c2}$, independently, is H, $C_1$-$C_{15}$ alkyl, $C_3$-$C_{20}$ cycloalkyl, $C_3$-$C_{20}$ heterocycloalkyl, heteroaryl, or aryl; each of $R_4$ and $R_5$, independently, is H, halogen, $C_1$-$C_{15}$ alkyl, $C_3$-$C_{20}$ cycloalkyl, $C_3$-$C_{20}$ heterocycloalkyl, heteroaryl, or aryl; one of $R_6$ and $R_7$ is $C_1$-$C_{15}$ alkyl substituted with $C_3$-$C_{20}$ heterocycloalkyl, heteroaryl, or aryl; and the other of $R_6$ and $R_7$ is H, $C_1$-$C_{15}$ alkyl, $C_3$-$C_{20}$ cycloalkyl, $C_3$-$C_{20}$ heterocycloalkyl, heteroaryl, or aryl; $R_8$ is H, halogen, $C_1$-$C_{15}$ alkyl, $C_3$-$C_{20}$ cycloalkyl, $C_3$-$C_{20}$ heterocycloalkyl, heteroaryl, aryl, $OR_{d1}$, or $SR_{d1}$; in which $R_{d1}$ is H and $C_1$-$C_{15}$ alkyl; and each of $R_9$ and $R_{10}$, independently, is H, halogen, $C_1$-$C_{15}$ alkyl, $C_3$-$C_{20}$ cycloalkyl, $C_3$-$C_{20}$ heterocycloalkyl, heteroaryl, aryl, $C(O)R_{e1}$, $CO_2R_{e1}$, $C(O)NR_{e1}R_{e2}$, $C(O)$—$N(R_{e1})$—$OR_{e2}$, $C(S)R_{e1}$, $C(S)NR_{e1}R_{e2}$, CN, $NO_2$, $S(O)R_{e1}$, $SO_2R_{e1}$, $S(O)NR_{e1}R_{e2}$, $S(O)$—$N(R_{e1})$—$OR_{e2}$, $SO_2NR_{e1}R_{e2}$, $SO_3R_{e1}$, $PO(OR_{e1})(OR_{e2})$, $PO(R_{e1})(R_{e2})$, $PO(NR_{e1}R_{e2})(OR_{e3})$, $PO(NR_{e1}R_{e2})(NR_{e3}R_{e4})$, $C(O)$—$N(R_{e1})$—$NR_{e2}R_{e3}$, or $C(S)$—$N(R_{e1})$—$NR_{e2}R_{e3}$; or $R_8$ and $R_{10}$, taken together, is $C_3$-$C_{20}$ cycloalkyl or $C_3$-$C_{20}$ heterocycloalkyl; or $R_9$ and $R_{10}$, taken together, is $C_3$-$C_{20}$ cycloalkyl or $C_3$-$C_{20}$ heterocycloalkyl; in which each of $R_{e1}$, $R_{e2}$, $R_{e3}$, and $R_{e4}$, independently, is H, $C_1$-$C_{15}$ alkyl, $C_3$-$C_{20}$ cycloalkyl, $C_3$-$C_{20}$ heterocycloalkyl, heteroaryl, or aryl; or any two of $R_{e1}$, $R_{e2}$, $R_{e3}$, and $R_{e4}$, together with the atom or atoms to which they are bonded, is $C_3$-$C_{20}$ heterocycloalkyl; and the virus is a coronavirus or a flaviviridae virus. Exemplary coronaviruses include a severe acute respiratory syndrome virus or a human coronavirus 229E. Exemplary flaviviridae viruses include flaviviruses (e.g., dengue virus, West Nile virus, Japanese encephalitis virus, yellow fever virus, and tick-borne encephalitis virus), pestiviruses (e.g., bovine viral diarrhea virus, classical swine fever virus, and border disease virus), and hepaciviruses (e.g., hepatitis C virus).

In particular, this invention features a method for treating an infection with a severe acute respiratory syndrome virus, a human coronavirus 229E, or a hepatitis C virus, by administering to a subject in need thereof an effective amount of a compound of formula (I) shown above.

For example, one can administer to a subject infected with a virus (e.g., a severe acute respiratory syndrome virus) a compound of formula (I), in which X is $N(R_{a1})$ or O; or X and one of $R_2$ and $R_3$, together with the atom or atoms to which they are bonded, are $C_3$-$C_{20}$ heterocycloalkyl; $R_1$ is H, $C(O)R_{b1}$, $CO_2R_{b1}$, $C(O)NR_{b1}R_{b2}$, $C(S)NR_{b1}R_{b2}$, or $SO_2R_{b1}$; each of $R_2$ and $R_3$, independently, is H or $C_1$-$C_{15}$ alkyl; or X and one of $R_2$ and $R_3$, together with the atom or atoms to which they are bonded, are $C_3$-$C_{20}$ heterocycloalkyl; each of $R_4$ and $R_5$, independently, is H or $C_1$-$C_{15}$ alkyl; one of $R_6$ and $R_7$ is $C_1$-$C_{15}$ alkyl substituted with $C_3$-$C_{20}$ heterocycloalkyl, and the other of $R_6$ and $R_7$ is H; $R_8$ is H; and each of $R_9$ and $R_{10}$, independently, is H or $CO_2R_{e1}$. In this compound, one of $R_6$ and $R_7$ can be

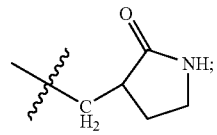

one of $R_2$ and $R_3$ can be H or $C_1$-$C_{15}$ alkyl optionally substituted with halogen, heteroaryl, aryl, $OR_{c1}$, $SR_{c1}$, $OC(O)R_{c1}$, $CO_2R_{c1}$, $C(O)NR_{c1}R_{c2}$, $NR_{c1}R_{c2}$, $N(R_{c1})$—$CO_2R_{c2}$, $N(R_{c1})$—$C(O)R_{c2}$, $N(R_{c1})$—$C(O)$—$NR_{c2}R_{c3}$, $N(R_{c1})$—$SO_2R_{c2}$, $SO_2R_{c1}$, or $O$—$SO_2$—$R_{c1}$; or X and one of $R_2$ and $R_3$, together with the atom or atoms to which they are bonded, are $C_3$-$C_{20}$ heterocycloalkyl; in which $R_{c3}$ is H, $C_1$-$C_{15}$ alkyl, $C_3$-$C_{20}$ cycloalkyl, $C_3$-$C_{20}$ heterocycloalkyl, heteroaryl, or aryl; and one of $R_4$ and $R_5$ can be H or $C_1$-$C_{15}$ alkyl optionally substituted with halogen, aryl, $OR_{f1}$, $SR_{f1}$, $CO_2R_{f1}$, $C(O)NR_{f1}R_{f2}$, $SO_2R_{f1}$, $SO_3R_{f1}$, or $NR_{f1}R_{f2}$; in which each of $R_{f1}$ and $R_{f2}$, independently, is H, $C_1$-$C_{15}$ alkyl, $C_3$-$C_{20}$ cycloalkyl, $C_3$-$C_{20}$ heterocycloalkyl, heteroaryl, or aryl.

The term "treating" refers to administering one or more compounds of the invention to a subject, who has an infection with a virus, a symptom of such an infection, or a predisposition toward such an infection, with the purpose to confer a therapeutic effect, e.g., to cure, relieve, alter, affect, ameliorate, or prevent the infection with a virus, the symptom of it, or the predisposition toward it. The term "an effective amount" refers to the amount of one or more active compounds of the invention that is required to confer a therapeutic effect on a treated subject.

The term "alkyl" refers to a saturated or unsaturated, linear or branched, non-aromatic hydrocarbon moiety, such as —$CH_3$, —$CH_2$—, —$CH_2$—$CH$=$CH_2$—, or branched —$C_3H_7$. The term "cycloalkyl" refers to a saturated or unsaturated, non-aromatic, cyclic hydrocarbon moiety, such as cyclohexyl or cyclohexen-3-yl. The term "heterocycloalkyl" refers to a saturated or unsaturated, non-aromatic, cyclic moiety having at least one ring heteroatom, such as 4-tetrahydropyranyl or 4-pyranyl. The term "aryl" refers to a hydrocarbon moiety having one or more aromatic rings. Examples of an aryl moiety include phenyl, phenylene, naphthyl, naphthylene, pyrenyl, anthryl, and phenanthryl. The term "heteroaryl" refers to a moiety having one or more aromatic rings that contain at least one heteroatom. Examples of a heteroaryl moiety include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, cycloalkyl, heterocycloalkyl, aryl, and heteroaryl mentioned herein include both substituted and unsubstituted moieties, unless specified otherwise. Examples of substituents on cycloalkyl, heterocycloalkyl, aryl, and heteroaryl include $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, halogen, thio, $C_1$-$C_{10}$ alkylthio, arylthio, $C_1$-$C_{10}$ alkylsulfonyl, arylsulfonyl, cyano, nitro, acyl, acyloxy, carboxyl, and carboxylic ester. On the other hand, examples of substituents on alkyl include all of the above-recited substituents except $C_1$-$C_{10}$ alkyl, $C_2$-$C_{10}$ alkenyl, and $C_2$-$l_{10}$ alkynyl. Cycloalkyl, heterocycloalkyl, aryl, and heteroaryl also include fused groups.

In another aspect, this invention features a method for inhibiting a viral protease (e.g., a coronaviral 3CL protease or a flaviviridae viral protease) in a cell. The method includes contacting the cell with an effective amount of a compound of formula (I) shown above. In particular, this invention features a method for inhibiting a severe acute respiratory syndrome viral 3CL protease, a human coronaviral 229E protease, or a hepatitis C viral protease.

In still another aspect, this invention features a compound of formula (I) shown above except that $R_1$ is H, $C_1$-$C_{15}$ alkyl, $C_3$-$C_{20}$ cycloalkyl, $C_3$-$C_{20}$ heterocycloalkyl, heteroaryl, aryl, $C(O)R_{b1}$, $CO_2R_{b2}$, $C(O)NR_{b3}R_{b4}$, $C(O)$—$N(R_{b3})$—$OR_{b4}$, $C(S)R_{b3}$, $C(S)NR_{b3}R_{b4}$, $S(O)R_{b3}$, $SO_2R_{b3}$, $S(O)NR_{b3}R_{b4}$, $S(O)$—$N(R_{b3})$—$OR_{b4}$, $SO_2NR_{b3}R_{b4}$, or $SO_3R_{b3}$; in which $R_{b1}$ is H, $C_1$-$C_{15}$ alkyl, $C_3$-$C_{20}$ cycloalkyl, $C_3$-$C_{20}$ heterocycloalkyl, 6-membered heteroaryl, fused heteroaryl, aryl, or $NHCO_2R_{b5}$; $R_{b2}$ is H, $C_3$-$C_{20}$ cycloalkyl, $C_3$-$C_{20}$ heterocycloalkyl, aryl, heteroaryl, or $C_1$-$C_{15}$ alkyl optionally substituted with halogen, $C_3$-$C_{20}$ cycloalkyl, $C_3$-$C_{20}$ heterocycloalkyl, heteroaryl, $OR_{b5}$, $CO_2R_{b5}$, or $S(O)_2R_{b5}$; and each of $R_{b3}$ and $R_{b4}$, independently, is H, $C_1$-$C_{15}$ alkyl, $C_3$-$C_{20}$ cycloalkyl, $C_3$-$C_{20}$ heterocycloalkyl, heteroaryl, or aryl; $R_{b5}$ being H, $C_1$-$C_{15}$ alkyl, heteroaryl, or aryl.

Referring to formula (I), a subset of the just-described compounds are those in which X is $N(R_{a1})$; or X and one of $R_2$ and $R_3$, together with the atom or atoms to which they are bonded, are $C_3$-$C_{20}$ heterocycloalkyl; $R_1$ is H, $C(O)R_{b1}$, $CO_2R_{b2}$, $C(O)NR_{b1}R_{b2}$, $C(S)NR_{b1}R_{b2}$, or $SO_2R_{b1}$, in which $R_{b1}$ is H, aryl, or $C_1$-$C_{15}$ alkyl optionally substituted with halogen, aryl, or $NHCO_2R_{b5}$; and $R_{b2}$ is aryl or $C_1$-$C_{15}$ alkyl optionally substituted with halogen, $OR_{b5}$, or $CO_2R_{b5}$; each of $R_2$ and $R_3$, independently, is H or $C_1$-$C_{15}$ alkyl optionally substituted with $OR_{c1}$, $C(O)$—$NR_{c1}R_{c2}$, $NR_{c1}R_{c2}$, $N(R_{c1})$—$CO_2R_{c2}$, $N(R_{c1})$—$SO_2R_{c2}$, or $O$—$SO_2$—$R_{c1}$; or X and one of $R_2$ and $R_3$, together with the atom or atoms to which they are bonded, are $C_3$-$C_{20}$ heterocycloalkyl; each of $R_4$ and $R_5$, independently, is H or $C_1$-$C_{15}$ alkyl; one of $R_6$ and $R_7$ is $C_1$-$C_{15}$ alkyl substituted with $C_3$-$C_{20}$ heterocycloalkyl, and the other of $R_6$ and $R_7$ is H; $R_8$ is H; and each of $R_9$ and $R_{10}$, independently, is H or $CO_2R_{c1}$. In these compounds, one of $R_6$ and $R_7$ can be

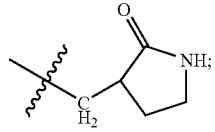

and one of $R_4$ and $R_5$ can be H or $C_1$-$C_{15}$ alkyl optionally substituted with aryl.

In still another aspect, this invention features a compound of formula (I) shown above except that $R_1$ is H, $C_1$-$C_{15}$ alkyl, $C_3$-$C_{20}$ cycloalkyl, $C_3$-$C_{20}$ heterocycloalkyl, heteroaryl, aryl, $C(O)R_{b1}$, $CO_2R_{b2}$, $C(O)NR_{b2}R_{b3}$, $C(O)$—$N(R_{b2})$—$OR_{b3}$, $C(S)R_{b2}$, $C(S)NR_{b2}R_{b3}$, $S(O)R_{b2}$, $SO_2R_{b2}$, $S(O)NR_{b2}R_{b3}$, $S(O)$—$N(R_{b2})$—$OR_{b3}$, $SO_2NR_{b2}R_{b3}$, or $SO_3R_{b2}$; in which $R_{b1}$ is H, $C_1$-$C_{15}$ alkyl, $C_3$-$C_{20}$ cycloalkyl, $C_3$-$C_{20}$ heterocycloalkyl, aryl, 6-membered heteroaryl, or fused heteroaryl; and each of $R_{b2}$ and $R_{b3}$, independently, is H, $C_1$-$C_{15}$ alkyl, $C_3$-$C_{20}$ cycloalkyl, $C_3$-$C_{20}$ heterocycloalkyl, aryl, or heteroaryl; and one of $R_2$ and $R_3$ is $C_1$-$C_{15}$ alkyl substituted with halogen, $OR_{c1}$, $SR_{c1}$, $CO_2R_{c1}$, $OC(O)R_{c1}$, $C(O)NR_{c1}R_{c2}$, $SO_2R_{c1}$, $O$—$SO_2$—$R_{c1}$, $NR_{c1}R_{c2}$, $N(R_{c1})$—$C(O)R_{c2}$, $N(R_{c1})$—$CO_2R_{c2}$, $N(R_{c1})$—$SO_2R_{c2}$, $N(R_{c1})$—$C(O)$—$N(R_{c2}R_{c3})$; the other of $R_2$ and $R_3$ is H, $C_1$-$C_{15}$ alkyl, $C_3$-$C_{20}$ cycloalkyl, $C_3$-$C_{20}$ heterocycloalkyl, heteroaryl, aryl, $OR_{c1}$, $SR_{c1}$, or $NR_{c1}R_{c2}$; in which each of $R_{c1}R_{c2}$, and $R_{c3}$, independently, is H, $C_1$-$C_{15}$ alkyl, $C_3$-$C_{20}$ cycloalkyl, $C_3$-$C_{20}$ heterocycloalkyl, heteroaryl, or aryl.

Referring to formula (I), a subset of the just-described compounds are those in which X is $N(R_{a1})$ or O; or X and one of $R_2$ and $R_3$, together with the atom or atoms to which they are bonded, are $C_3$-$C_{20}$ heterocycloalkyl; $R_1$ is $CO_2R_{b2}$, in which $R_{b2}$ is alkyl substituted with aryl; one of $R_2$ and $R_3$ is $C_1$-$C_{15}$ alkyl substituted with $OR_{c1}$, $SR_{c1}$, $OC(O)R_{c1}$, $CO_2R_{c1}$, $C(O)NR_{c1}R_{c2}$, $SO_2R_{c1}$, $O$—$SO_2$—$R_{c1}$, $NR_{c1}R_{c2}$, $N(R_{c1})$—$C(O)R_{c2}$, $N(R_{c1})$—$CO_2R_{c2}$, $N(R_{c1})$—$SO_2R_{c2}$, $N(R_{c1})$—$C(O)$—$N(R_{c2}R_{c3})$, and the other of $R_2$ and $R_3$ is H; or X and one of $R_2$ and $R_3$, together with the atom or atoms to which they are bonded, are $C_3$-$C_{20}$ *heterocycloalkyl; each of*

$R_4$ and $R_5$, independently, is H or $C_1$-$C_{15}$ alkyl; one of $R_6$ and $R_7$ is $C_1$-$C_{15}$ alkyl substituted with $C_3$-$C_{20}$ heterocycloalkyl, and the other of $R_6$ and $R_7$ is H; $R_8$ is H; and each of $R_9$ and $R_{10}$, independently, is H, CN, C(O)$R_{e1}$, CO$_2R_{e1}$, or C(O)NR$_{e1}R_{e2}$; or $R_9$ and $R_{10}$, taken together, are $C_3$-$C_{20}$ heterocycloalkyl. In these compounds, one of $R_6$ and $R_7$ can be

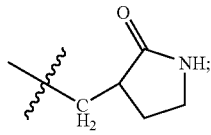

and one of $R_4$ and $R_5$ can be H or $C_1$-$C_{15}$ alkyl optionally substituted with aryl, $C_3$-$C_{20}$ cycloalkyl, OR$_{f1}$, SR$_{f1}$, NR$_{f1}R_{f2}$, or C(O)NR$_{f1}R_{f2}$; in which each of R$_{f1}$ and R$_{f2}$, independently, is H, $C_1$-$C_{15}$ alkyl, $C_3$-$C_{20}$ cycloalkyl, $C_3$-$C_{20}$ heterocycloalkyl, heteroaryl, or aryl.

In still another aspect, this invention features a compound of formula (I) shown above except that $R_1$ is H, $C_1$-$C_{15}$ alkyl, $C_3$-$C_{20}$ cycloalkyl, $C_3$-$C_{20}$ heterocycloalkyl, heteroaryl, aryl, C(O)$R_{b1}$, CO$_2R_{b2}$, C(O)NR$_{b2}R_{b3}$, C(O)—N($R_{b2}$)—OR$_{b3}$, C(S)$R_{b2}$, C(S)NR$_{b2}R_{b3}$, S(O)$R_{b2}$, SO$_2R_{b2}$, S(O)NR$_{b2}R_{b3}$, S(O)—N($R_{b2}$)—OR$_{b3}$, SO$_2$NR$_{b2}R_{b3}$, or SO$_3R_{b2}$; in which $R_{b1}$ is H, $C_1$-$C_{15}$ alkyl, $C_3$-$C_{20}$ cycloalkyl, $C_3$-$C_{20}$ heterocycloalkyl, aryl, 6-membered heteroaryl, or fused heteroaryl; and each of $R_{b2}$ and $R_{b3}$, independently, is H, $C_1$-$C_{15}$ alkyl, $C_3$-$C_{20}$ cycloalkyl, $C_3$-$C_{20}$ heterocycloalkyl, aryl, or heteroaryl; one of $R_4$ and $R_5$ is $C_1$-$C_{15}$ alkyl substituted with halogen, OR$_{d1}$, SR$_{d1}$, CO$_2R_{d1}$, C(O)NR$_{d1}R_{d2}$, SO$_2R_{d1}$, SO$_3R_{d1}$, or NR$_{d1}R_{d2}$; the other of $R_4$ and $R_5$ is H, halogen, $C_1$-$C_{15}$ alkyl, $C_3$-$C_{20}$ cycloalkyl, $C_3$-$C_{20}$ heterocycloalkyl, heteroaryl, or aryl; in which each of $R_{d1}$ and $R_{d2}$, independently, is H, $C_1$-$C_{15}$ alkyl, $C_3$-$C_{20}$ cycloalkyl, $C_3$-$C_{20}$ heterocycloalkyl, heteroaryl, or aryl; $R_8$ is H, halogen, $C_1$-$C_{15}$ alkyl, $C_3$-$C_{20}$ cycloalkyl, $C_3$-$C_{20}$ heterocycloalkyl, heteroaryl, aryl, OR$_{e1}$, or SR$_{e1}$; in which $R_{e1}$ is H and $C_1$-$C_{15}$ alkyl; and each of $R_9$ and $R_{10}$, independently, is H, halogen, $C_1$-$C_{15}$ alkyl, $C_3$-$C_{20}$ cycloalkyl, $C_3$-$C_{20}$ heterocycloalkyl, heteroaryl, aryl, C(O)$R_{f1}$, CO$_2R_{f1}$, C(O)NR$_{f1}R_{f2}$, C(O)—N($R_{f1}$)—OR$_{f2}$, C(S)R$_{f1}$, C(S)NR$_{f1}R_{f2}$, CN, NO$_2$, S(O)R$_{f1}$, S(O)NR$_{f1}R_{f2}$, S(O)—N($R_{f1}$)—OR$_{f2}$, SO$_2$NR$_{f1}R_{f2}$, SO$_3R_{f1}$, PO(OR$_{f1}$)(OR$_{f2}$), PO(R$_{f1}$)(R$_{f2}$), PO(NR$_{f1}R_{f2}$)(OR$_{f3}$), PO(NR$_{f1}R_{f2}$)(NR$_{f3}R_{f4}$), C(O)—N(R$_{f1}$)—NR$_{f2}R_{f3}$, or C(S)—N(R$_{f1}$)—NR$_{f2}R_{f3}$; or $R_8$ and $R_{10}$, taken together, is $C_3$-$C_{20}$ cycloalkyl or $C_3$-$C_{20}$ heterocycloalkyl; or $R_9$ and $R_{10}$, taken together, is $C_3$-$C_{20}$ cycloalkyl or $C_3$-$C_{20}$ heterocycloalkyl; in which each of R$_{f1}$, R$_{f2}$, R$_{f3}$, and R$_{f4}$, independently, is H, $C_1$-$C_{15}$ alkyl, $C_3$-$C_{20}$ cycloalkyl, $C_3$-$C_{20}$ heterocycloalkyl, heteroaryl, or aryl; or any two of R$_{f1}$, R$_{f2}$, R$_{f3}$, and R$_{f4}$, together with the atom or atoms to which they are bonded, is $C_3$-$C_{20}$ heterocycloalkyl.

Referring to formula (I), a subset of the just-described compounds are those in which X is N(R$_{a1}$) or O; $R_1$ is CO$_2R_{b2}$, in which R$_{b2}$ is alkyl substituted with aryl; each of $R_2$ and $R_3$, independently, is H or $C_1$-$C_{15}$ alkyl optionally substituted with aryl; one of $R_4$ and $R_5$ is $C_1$-$C_{15}$ alkyl substituted with SR$_{d1}$ or C(O)NR$_{d1}R_{d2}$, and the other of $R_4$ and $R_5$ is H; one of $R_6$ and $R_7$ is $C_1$-$C_{15}$ alkyl substituted with $C_3$-$C_{20}$ heterocycloalkyl, and the other of $R_6$ and $R_7$ is H; $R_8$ is H; and each of $R_9$ and $R_{10}$, independently, is H or CO$_2R_{f1}$. In these compounds, one of $R_6$ and $R_7$ can be

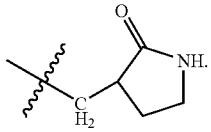

In a further aspect, this invention features a method for treating an infection with a virus. The method includes administering to a subject in need thereof an effective amount of a compound of formula (II):

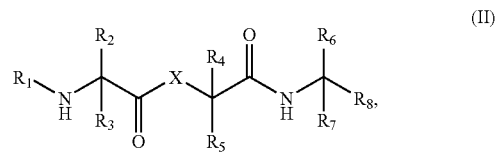

(II)

In this formula, X is N(R$_{a1}$), O, or CH$_2$; or X and one of $R_2$ and $R_3$, together with the atom or atoms to which they are bonded, are $C_3$-$C_{20}$ heterocycloalkyl; in which R$_{a1}$ is H or $C_1$-$C_{15}$ alkyl; $R_1$ is H, $C_1$-$C_{15}$ alkyl, $C_3$-$C_{20}$ cycloalkyl, $C_3$-$C_{20}$ heterocycloalkyl, heteroaryl, aryl, C(O)$R_{b1}$, CO$_2R_{b1}$, C(O)NR$_{b1}R_{b2}$, C(O)—N($R_{b1}$)—OR$_{b2}$, C(S)$R_{b1}$, C(S)NR$_{b1}R_{b2}$, S(O)R$_{b1}$, SO$_2R_{b1}$, S(O)NR$_{b1}R_{b2}$, S(O)—N($R_{b1}$)—OR$_{b2}$, SO$_2$NR$_{b1}R_{b2}$, or SO$_3R_{b1}$; in which each of $R_{b1}$ and $R_{b2}$, independently, is H, $C_1$-$C_{15}$ alkyl, $C_3$-$C_{20}$ cycloalkyl, $C_3$-$C_{20}$ heterocycloalkyl, heteroaryl, or aryl; each of $R_2$ and $R_3$, independently, is H, $C_1$-$C_{15}$ alkyl, $C_3$-$C_{20}$ cycloalkyl, $C_3$-$C_{20}$ heterocycloalkyl, heteroaryl, aryl, OR$_{c1}$, SR$_{c1}$, or NR$_{c1}R_{c2}$; or X and one of $R_2$ and $R_3$, together with the atom or atoms to which they are bonded, are $C_3$-$C_{20}$ heterocycloalkyl; in which each of R$_{c1}$ and R$_{c2}$, independently, is H, $C_1$-$C_{15}$ alkyl, $C_3$-$C_{20}$ cycloalkyl, $C_3$-$C_{20}$ heterocycloalkyl, heteroaryl, or aryl; each of $R_4$ and $R_5$, independently, is H, halogen, $C_1$-$C_{15}$ alkyl, $C_3$-$C_{20}$ cycloalkyl, $C_3$-$C_{20}$ heterocycloalkyl, heteroaryl, or aryl; and one of $R_6$, $R_7$, and $R_8$ is $C_1$-$C_{15}$ alkyl substituted with $C_3$-$C_{20}$ heterocycloalkyl, heteroaryl, or aryl; and the others of $R_6$, $R_7$, and $R_8$, independently, is H, halogen, $C_1$-$C_{15}$ alkyl, $C_3$-$C_{20}$ cycloalkyl, $C_3$-$C_{20}$ heterocycloalkyl, heteroaryl, aryl, OR$_{d1}$, SR$_{d1}$, C(O)$R_{d1}$, CO$_2R_{d1}$, C(O)NR$_{d1}R_{d2}$, or C(O)—N(R$_{d1}$)—OR$_{d2}$; in which R$_{d1}$ and R$_{d2}$, independently, is H, $C_1$-$C_{15}$ alkyl, $C_3$-$C_{20}$ cycloalkyl, $C_3$-$C_{20}$ heterocycloalkyl, heteroaryl, or aryl; and the virus is a coronavirus or a flaviviridae virus.

In particular, this invention features a method for treating an infection with a severe acute respiratory syndrome virus, a human coronavirus 229-E, or a hepatitis C virus, by administering to a subject in need thereof an effective amount of a compound of formula (II) shown above.

For example, one can administer to a subject infected with a virus (e.g., a severe acute respiratory syndrome virus) a compound of formula (II), in which X is N(R$_{a1}$); $R_1$ is CO$_2R_{b1}$, in which R$_{b1}$ is alkyl substituted with aryl; each of $R_2$ and $R_3$, independently, is H or $C_1$-$C_{15}$ alkyl optionally substituted with OR$_{c1}$, CO$_2R_{c1}$, N(R$_{c1}$)—CO$_2R_{c2}$, or OC(O)—NR$_{c1}R_{c2}$; each of $R_4$ and $R_5$, independently, is H or $C_1$-$C_{15}$ alkyl; $R_6$ is $C_1$-$C_{15}$ alkyl substituted with $C_3$-$C_{20}$ heterocycloalkyl; $R_7$ is H; and $R_8$ is C(O)R$_{d1}$, CO$_2R_{d1}$, C(O)—

$N(R_{d1})$—$OR_{d2}$, or $C_1$-$C_{15}$ alkyl optionally substituted with halogen or OH. In these compounds, $R_1$ can be

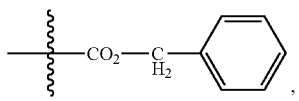

one of $R_6$ and $R_7$ can be

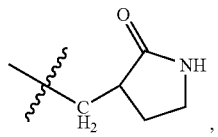

and $R_8$ is C(O)—N(CH$_3$)—OCH$_3$, CH$_2$OH, C(O)—CH=CH$_2$, CHO, CO$_2$CH$_3$, C(O)CH$_3$, or CH$_2$Cl.

In a further aspect, this invention features a method for inhibiting a viral protease (e.g., a coronaviral 3CL protease or a flaviviridae viral protease) in a cell, by contacting the cell with an effective amount of a compound of formula (II) shown above. In particular, this invention features a method for inhibiting a severe acute respiratory syndrome viral 3CL protease, a human coronaviral 229E protease, or a hepatitis C viral protease.

In a further aspect, this invention features a compound of formula (II) shown above.

In still a further aspect, this invention features a method for treating an infection with a picornavirus (e.g., an enterovirus or a rhinovirus). The method includes administering to a subject in need thereof an effective amount of a compound of formula (I) or a compound of formula (II).

In still a further aspect, this invention features a method for inhibiting a picornaviral protease (e.g., an enteroviral protease or a rhinoviral 3C protease) in a cell. The method includes contacting the cell with an effective amount of a compound of formula (I) or a compound of formula (II).

In yet a further aspect, this invention features a chemical synthetic method. The method includes reducing a compound of formula (III):

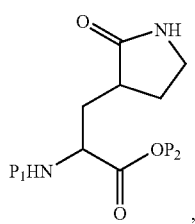

(III)

to form an alcohol, followed by reacting the alcohol with Ph$_3$P=COOR in the presence of pyridine sulfur trioxide to give a compound of formula (IV):

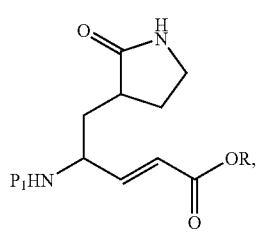

(IV)

in which $P_1$ is an amino-protecting group; $P_2$ is a carboxyl-protecting group; and R is $C_1$-$C_{15}$ alkyl, $C_3$-$C_{20}$ cycloalkyl, $C_3$-$C_{20}$ heterocycloalkyl, heteroaryl, or aryl. In formulas (III) and (IV), $P_1$ can be t-butoxycarbonyl, benzyloxycarbonyl, acetyl, phenylcarbonyl, or trialkylsilyl; $P_2$ can be $C_1$-$C_{15}$ alkyl; and R can be $C_1$-$C_{15}$ alkyl.

In particular, the chemical synthetic method can further include removing the amino-protecting group $P_1$ of the compound of formula (IV) to form a first de-protected intermediate, and then reacting the first de-protected intermediate with $P_3HN$—$CH(R_5)$—COOH to give a compound of formula (V):

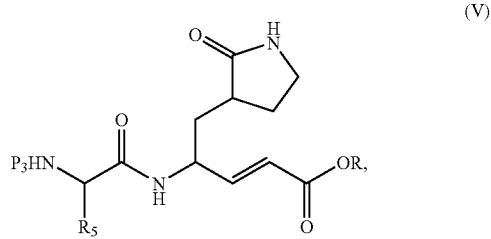

(V)

in which $P_3$ is an amino-protecting group and $R_5$ is H, halogen, $C_1$-$C_{15}$ alkyl, $C_3$-$C_{20}$ cycloalkyl, $C_3$-$C_{20}$ heterocycloalkyl, heteroaryl, or aryl. The method can further include removing the amino-protecting group $P_3$ of the compound of formula (V) to form a second de-protected intermediate, and then reacting the second de-protected intermediate with $R_1HN$—$CH(R_2)$—COOH to give a compound of formula (VI):

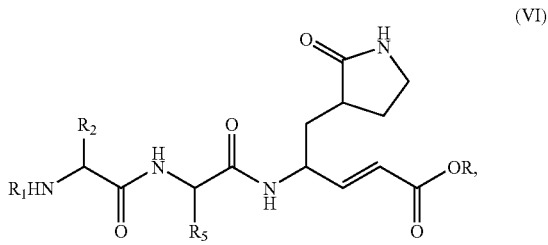

(VI)

in which $R_1$ is H, $C_1$-$C_{15}$ alkyl, $C_3$-$C_{20}$ cycloalkyl, $C_3$-$C_{20}$ heterocycloalkyl, heteroaryl, aryl, $C(O)R_{b1}$, $CO_2R_{b1}$, $C(O)NR_{b1}R_{b2}$, C(O)—N($R_{b1}$)—$OR_{b2}$, $C(S)R_{b1}$, $C(S)NR_{b1}R_{b2}$, $S(O)R_{b1}$, $SO_2R_{b1}$, $S(O)NR_{b1}R_{b2}$, S(O)—N($R_{b1}$)—$OR_{b2}$, $SO_2NR_{b1}R_{b2}$, or $SO_3R_{b1}$; in which each of $R_{b1}$ and $R_{b2}$, independently, is H, $C_1$-$C_{15}$ alkyl, $C_3$-$C_{20}$ cycloalkyl, $C_3$-$C_{20}$ heterocycloalkyl, heteroaryl, or aryl; and $R_2$ is H, $C_1$-$C_{15}$ alkyl, $C_3$-$C_{20}$ cycloalkyl, $C_3$-$C_{20}$ heterocycloalkyl, heteroaryl, aryl, $OR_{c1}$, $SR_{c1}$, or $NR_{c1}R_{c2}$; or X and one of $R_2$ and $R_3$, together with the atom or atoms to which they are bonded, are $C_3$-$C_{20}$ heterocycloalkyl; in which each of $R_{c1}$ and $R_{c2}$, independently, is H, $C_1$-$C_{15}$ alkyl, $C_3$-$C_{20}$ cycloalkyl, $C_3$-$C_{20}$ heterocycloalkyl, heteroaryl, or aryl. In formulas (V) and (VI), $P_3$ can be t-butoxycarbonyl, benzyloxycarbonyl, acetyl, phenylcarbonyl, or trialkylsilyl; and R can be $C_1$-$C_{15}$ alkyl.

Alternatively, the chemical synthetic method mentioned above can further include removing the amino-protecting group $P_1$ of the compound of formula (IV) to form a first de-protected intermediate, and then reacting the first de-protected intermediate with a compound of formula (VII):

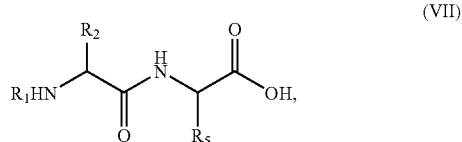

(VII)

(VII), to give a compound of formula (VI):

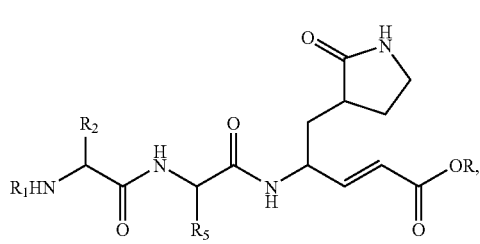

(VI)

in which $R_1$ is H, $C_1$-$C_{15}$ alkyl, $C_3$-$C_{20}$ cycloalkyl, $C_3$-$C_{20}$ heterocycloalkyl, heteroaryl, aryl, $C(O)R_{b1}$, $CO_2R_{b1}$, $C(O)NR_{b1}R_{b2}$, $C(O)$—$N(R_{b1})$—$OR_{b2}$, $C(S)R_{b1}$, $C(S)NR_{b1}R_{b2}$, $S(O)R_{b1}$, $SO_2R_{b1}$, $S(O)NR_{b1}R_{b2}$, $S(O)$—$N(R_{b1})$—$OR_{b2}$, $SO_2NR_{b1}R_{b2}$, or $SO_3R_{b1}$; in which each of $R_{b1}$ and $R_{b2}$, independently, is H, $C_1$-$C_{15}$ alkyl, $C_3$-$C_{20}$ cycloalkyl, $C_3$-$C_{20}$ heterocycloalkyl, heteroaryl, or aryl; $R_2$ is H, $C_1$-$C_{15}$ alkyl, $C_3$-$C_{20}$ cycloalkyl, $C_3$-$C_{20}$ heterocycloalkyl, heteroaryl, aryl, $OR_{c1}$, $SR_{c1}$, or $NR_{c1}R_{c2}$; or X and one of $R_2$ and $R_3$, together with the atom or atoms to which they are bonded, are $C_3$-$C_{20}$ heterocycloalkyl; in which each of $R_{c1}$ and $R_{c2}$, independently, is H, $C_1$-$C_{15}$ alkyl, $C_3$-$C_{20}$ cycloalkyl, $C_3$-$C_{20}$ heterocycloalkyl, heteroaryl, or aryl; and $R_5$ is H, halogen, $C_1$-$C_{15}$ alkyl, $C_3$-$C_{20}$ cycloalkyl, $C_3$-$C_{20}$ heterocycloalkyl, heteroaryl, or aryl.

In addition, the chemical synthetic method can further include removing the amino-protecting group $P_1$ of the compound of formula (IV) to form a first de-protected intermediate, and then reacting the first de-protected intermediate with a compound of formula (VIII):

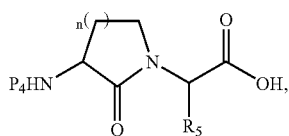

(VIII)

in which n is 1, 2, or 3; $P_4$ is an amino-protecting group; and $R_5$ is H, halogen, $C_1$-$C_{15}$ alkyl, $C_3$-$C_{20}$ cycloalkyl, $C_3$-$C_{20}$ heterocycloalkyl, heteroaryl, or aryl; followed by removing the amino-protecting group $P_4$ to give a compound of formula (IX):

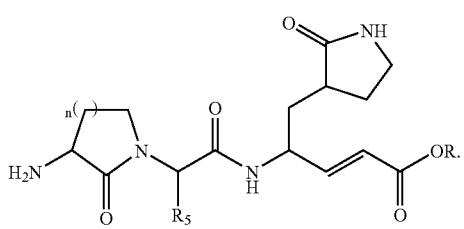

(IX)

The compound of formula (IX) can further react with $R_1$'COOH or $R_1$'COCl to give a compound of formula (X):

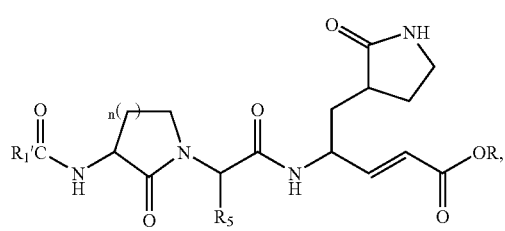

(X)

in which $R_1$' is H, $C_1$-$C_{15}$ alkyl, $C_3$-$C_{20}$ cycloalkyl, $C_3$-$C_{20}$ heterocycloalkyl, heteroaryl, aryl, or $OR_{b1}$; $R_{b1}$ being H, $C_1$-$C_{15}$ alkyl, $C_3$-$C_{20}$ cycloalkyl, $C_3$-$C_{20}$ heterocycloalkyl, heteroaryl, or aryl. In formulas (VIII), (IX), and (X), $P_4$ can be t-butoxycarbonyl, benzyloxycarbonyl, acetyl, phenylcarbonyl, or trialkylsilyl; and R can be $C_1$-$C_{15}$ alkyl.

In addition, this invention encompasses a pharmaceutical composition that contains an effective amount of at least one of the above-mentioned compounds and a pharmaceutically acceptable carrier.

The compounds of the invention include the compounds themselves, as well as their salts, prodrugs, and solvates, if applicable. A salt, for example, can be formed between an anion and a positively charged group (e.g., amino) on a compound of the invention. Examples of suitable anions include chloride, bromide, iodide, sulfate, nitrate, phosphate, citrate, methanesulfonate, trifluoroacetate, and acetate. Likewise, a salt can also be formed between a cation and a negatively charged group (e.g., carboxylate) on a compound of the invention. Examples of suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds of the invention. A solvate refers to a complex formed between an active compound of the invention and a pharmaceutically acceptable solvent. Examples of pharmaceutically acceptable solvents include water, ethanol, isopropanol, ethyl acetate, acetic acid, and ethanolamine.

Also within the scope of this invention is a composition containing one or more of the compounds described above for use in treating an infection with a virus, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

Shown below are the structures of compounds 1-145, exemplary compounds of this invention:

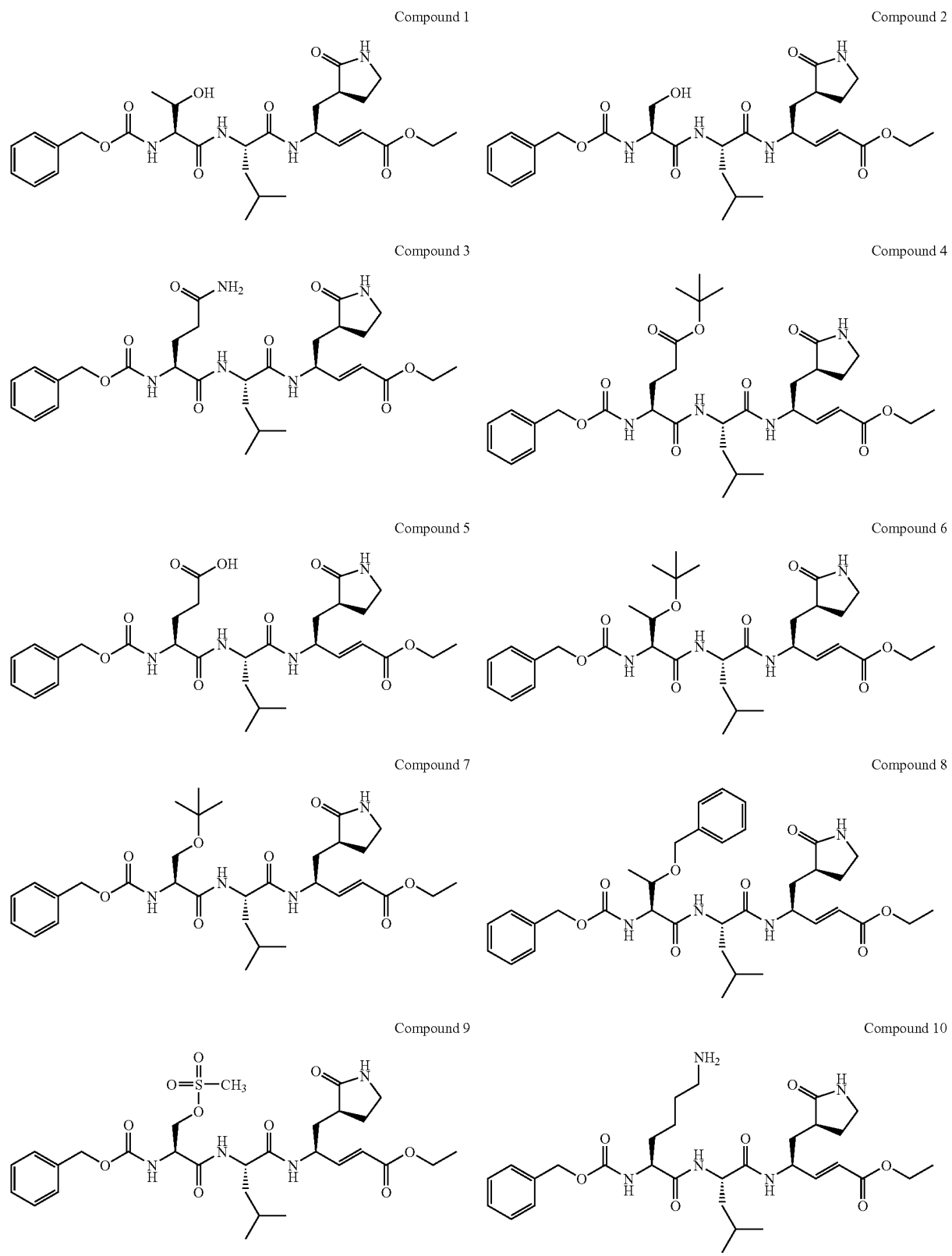

-continued
Compound 11
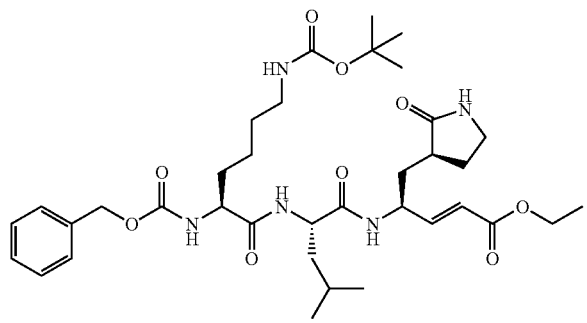
Compound 12
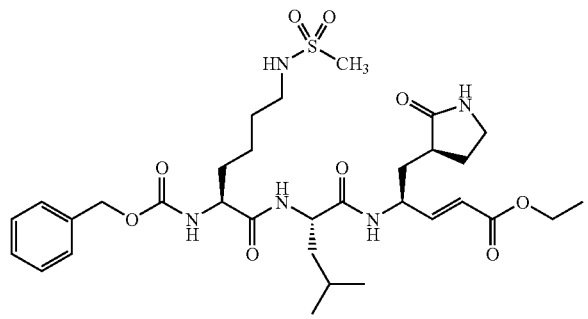
Compound 13
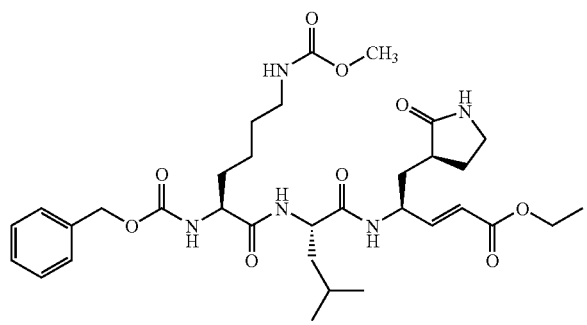
Compound 14
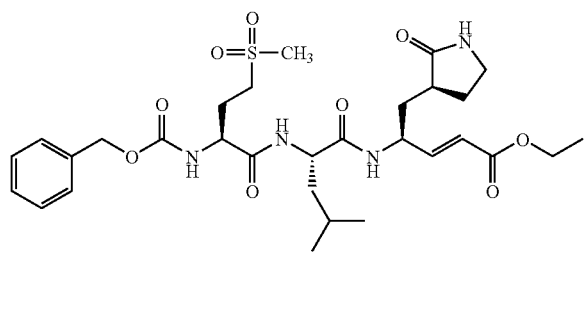
Compound 15
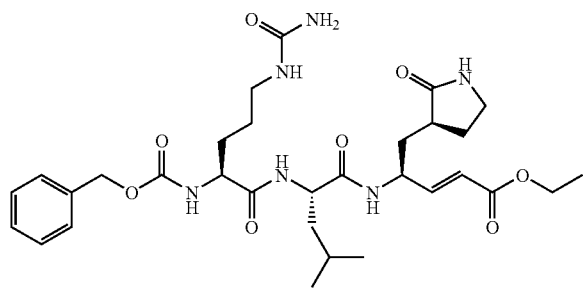
Compound 16
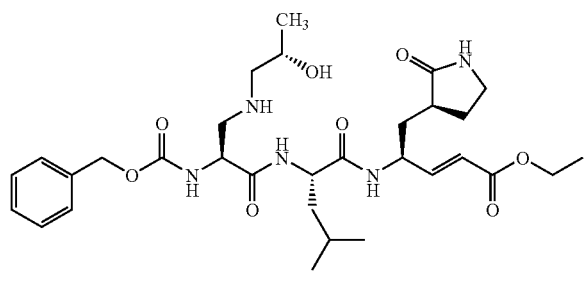
Compound 17
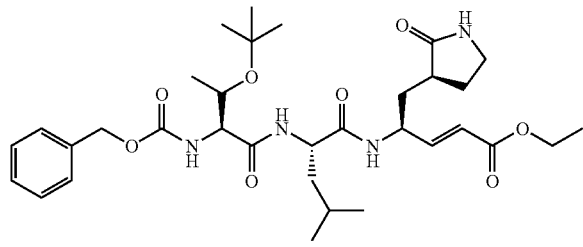
Compound 18
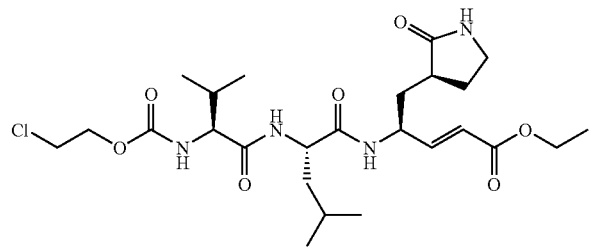
Compound 19
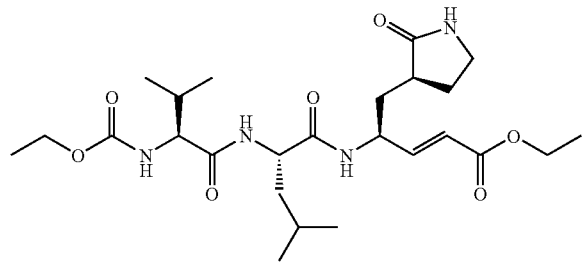
Compound 20
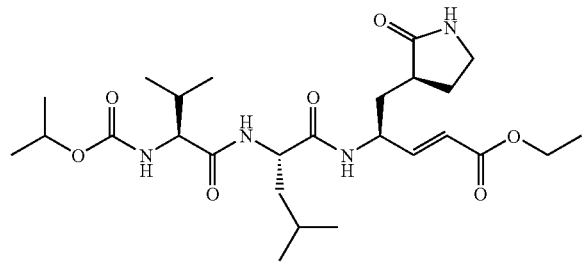

-continued
Compound 21
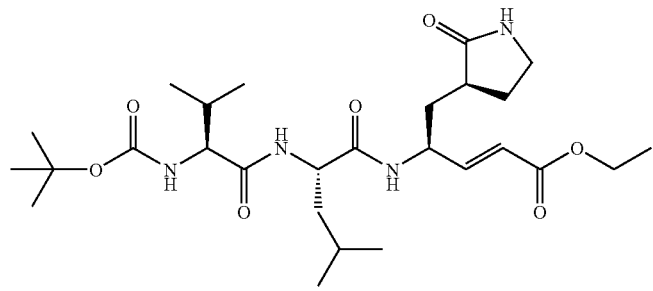
Compound 22
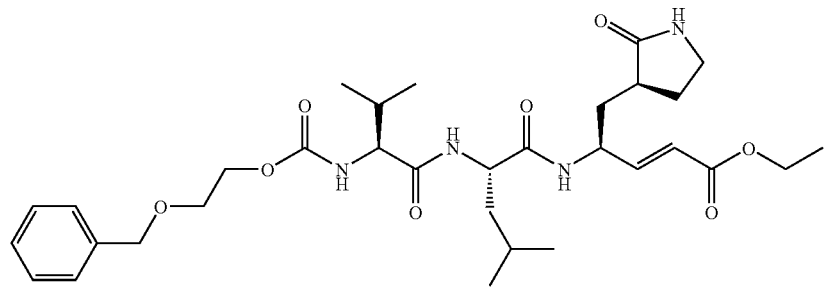
Compound 23
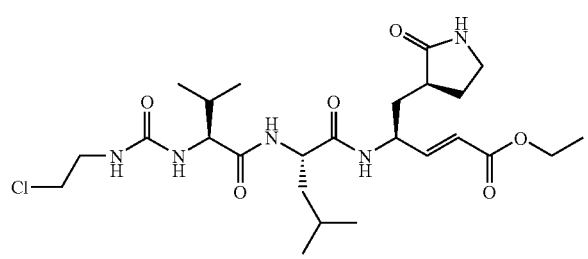
Compound 24
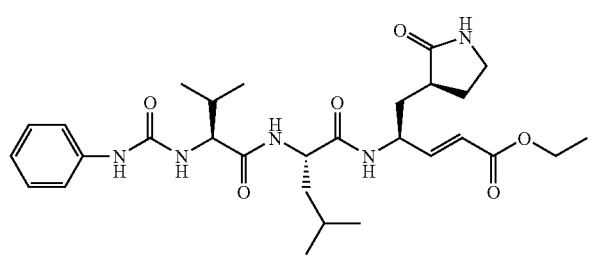
Compound 25
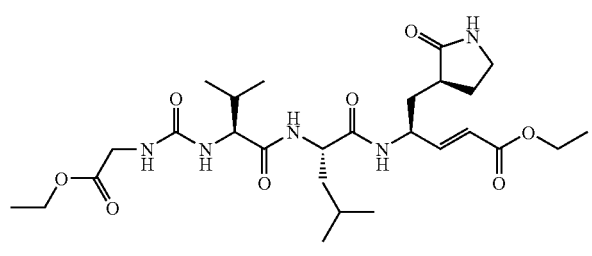
Compound 26
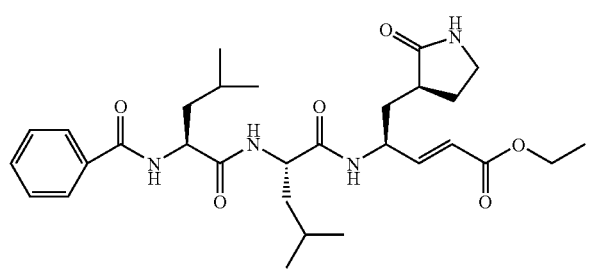
Compound 27
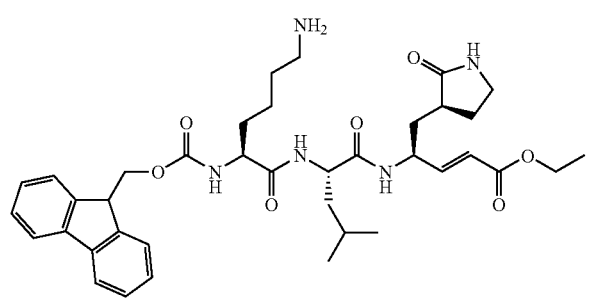
Compound 28
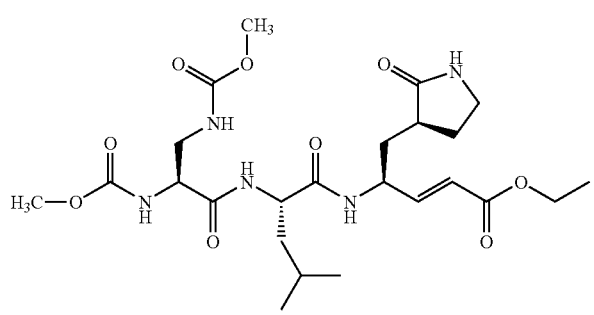

-continued
Compound 29
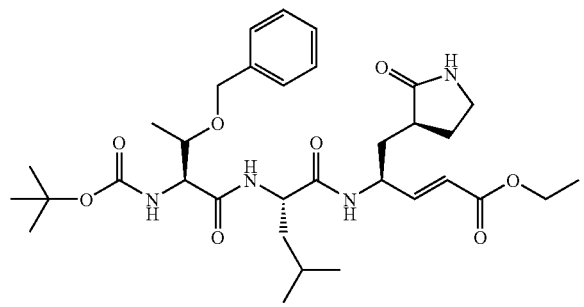
Compound 30
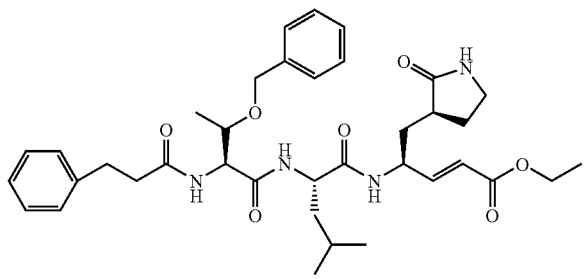
Compound 31
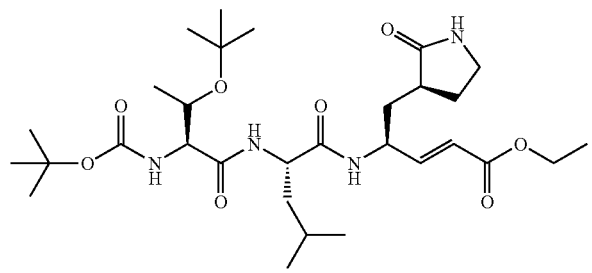
Compound 32
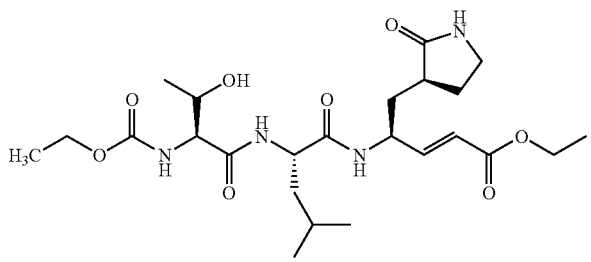
Compound 33
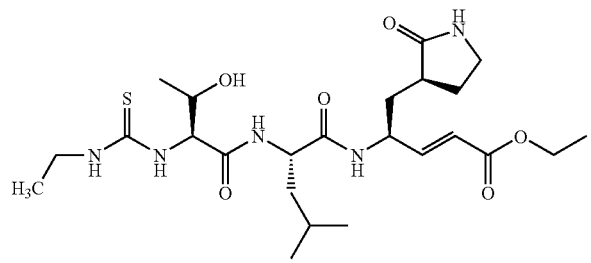
Compound 34
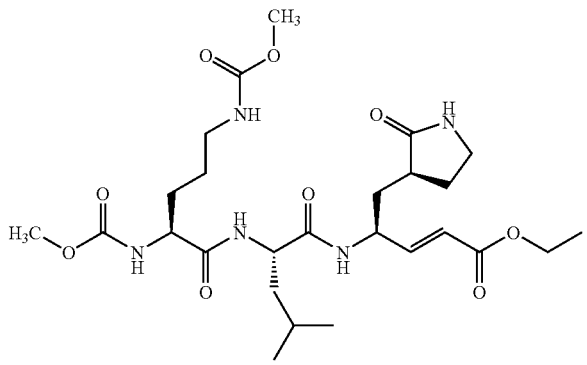
Compound 35
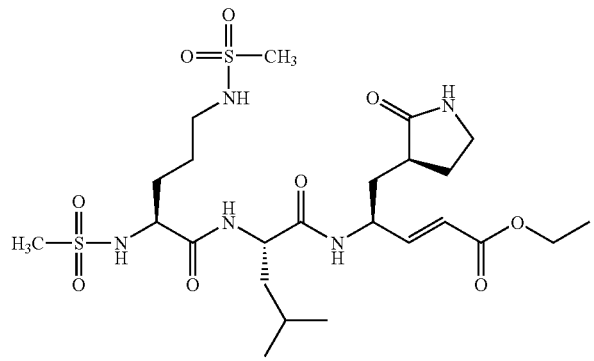
Compound 36
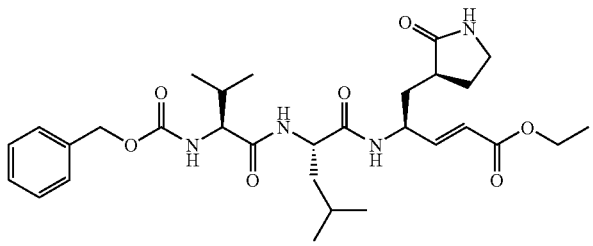

-continued
Compound 37
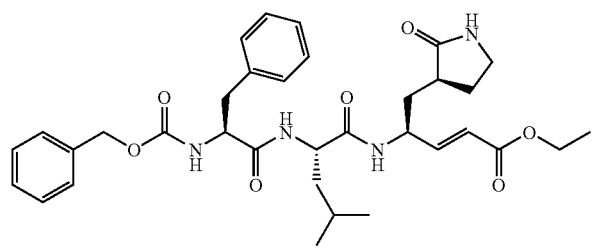
Compound 38
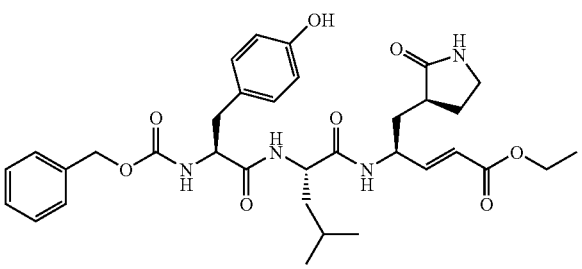
Compound 39
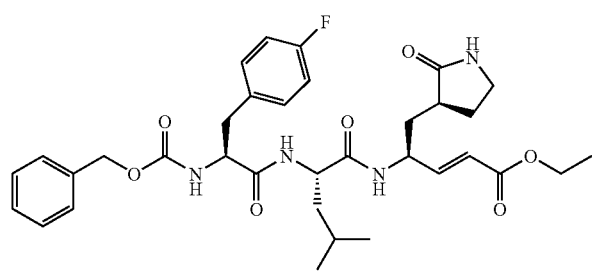
Compound 40
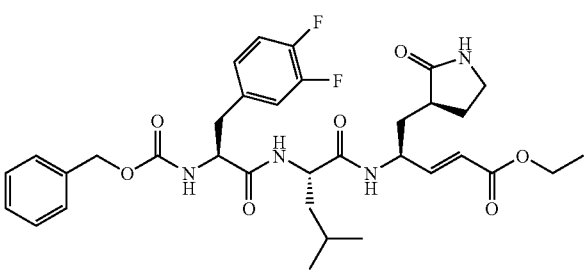
Compound 41
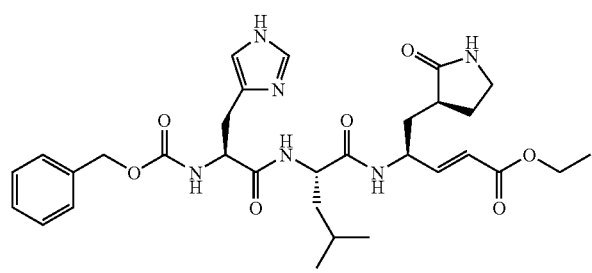
Compound 42
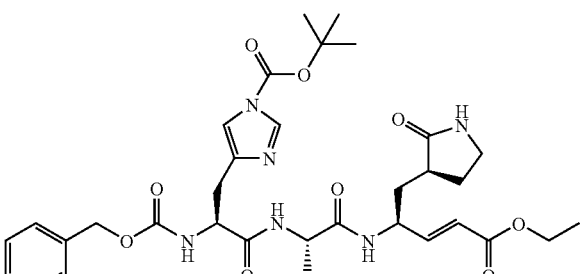
Compound 43
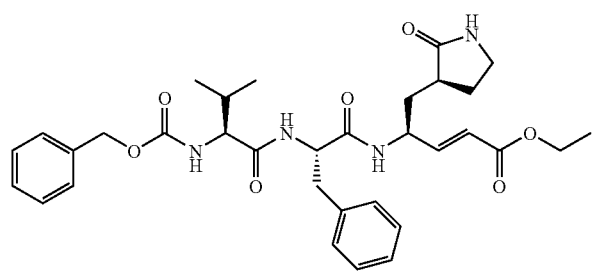
Compound 44
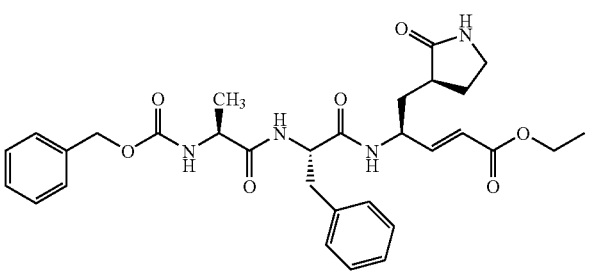
Compound 45
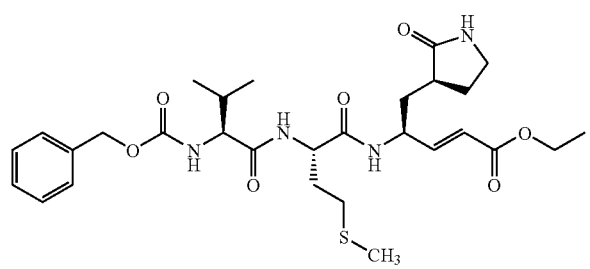
Compound 46
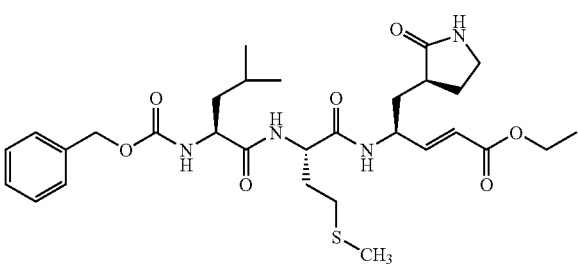

-continued
Compound 47
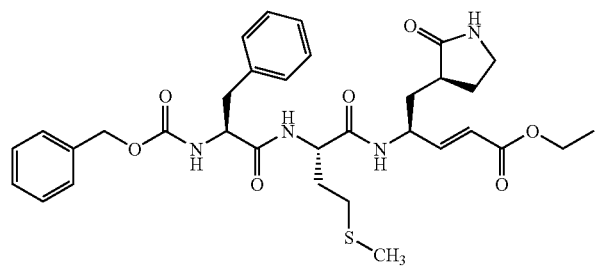
Compound 48
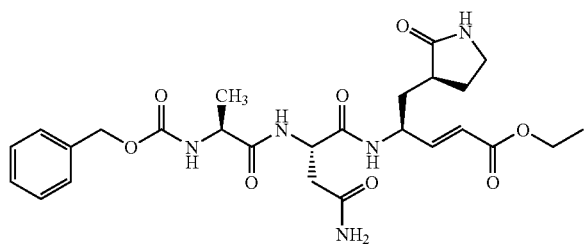
Compound 49
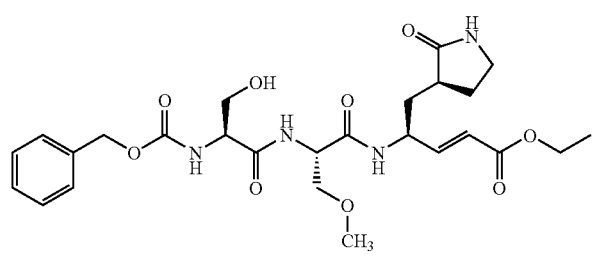
Compound 50
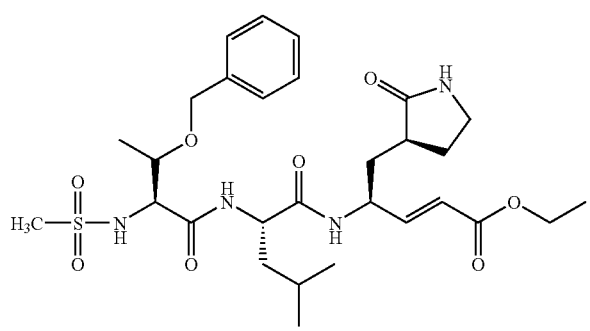
Compound 51
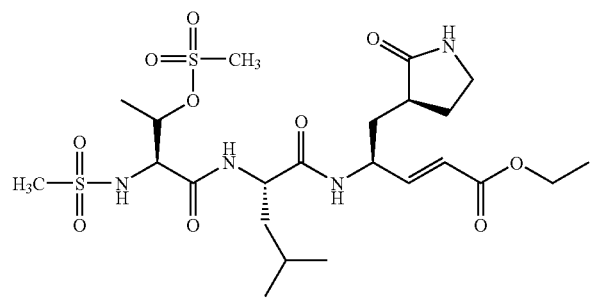
Compound 52
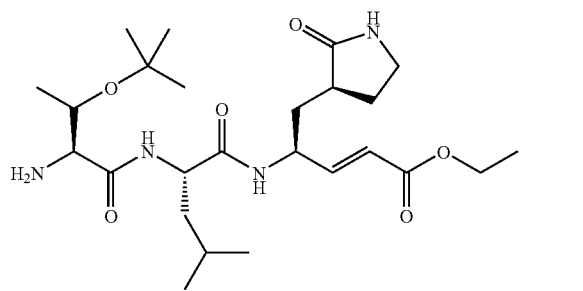
Compound 53
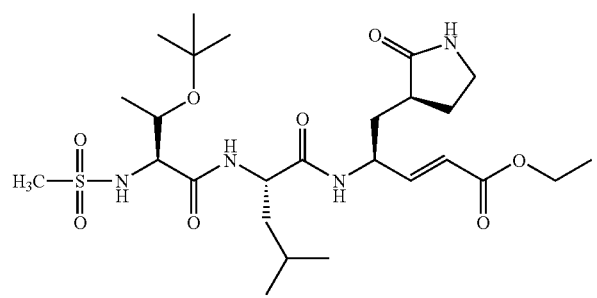
Compound 54
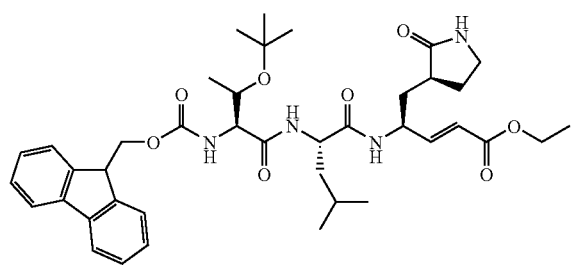
Compound 55
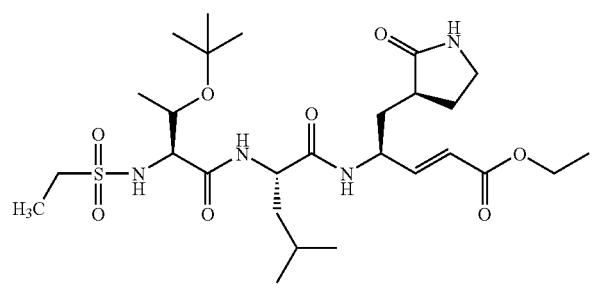
Compound 56
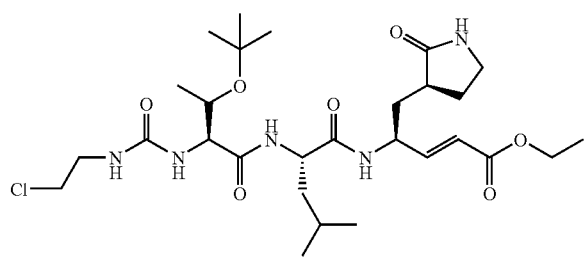

-continued
Compound 57
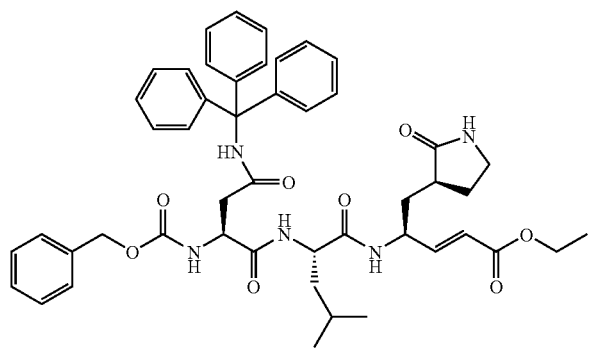
Compound 58
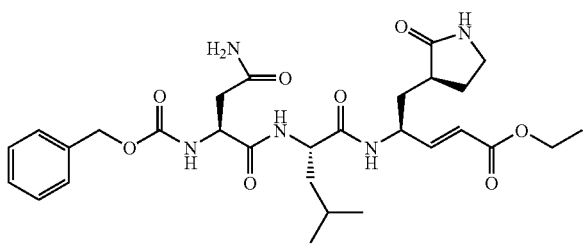
Compound 59
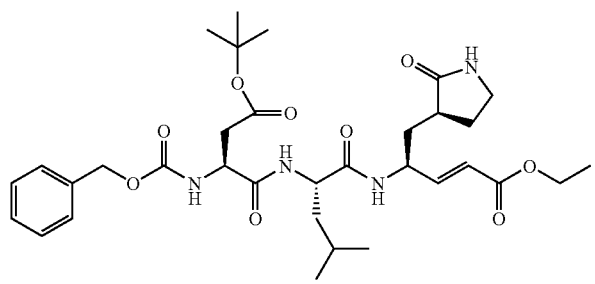
Compound 60
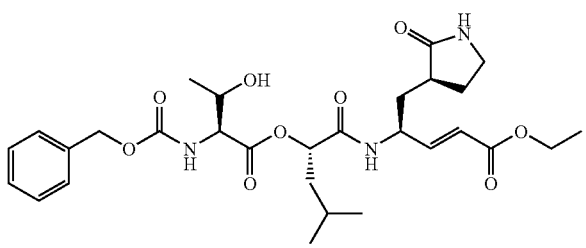
Compound 61
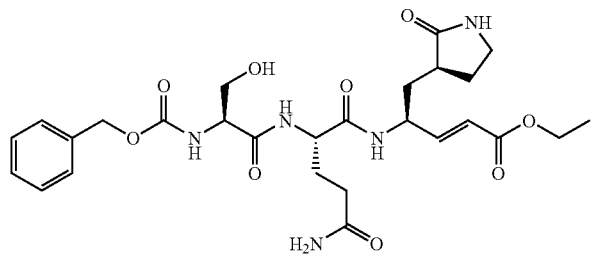
Compound 62
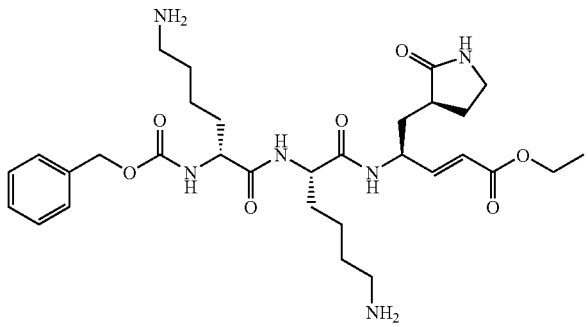
Compound 63
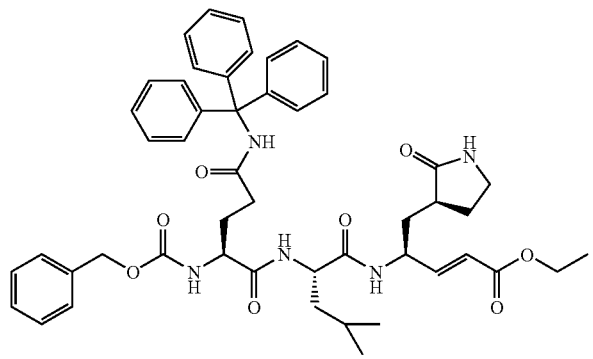
Compound 64
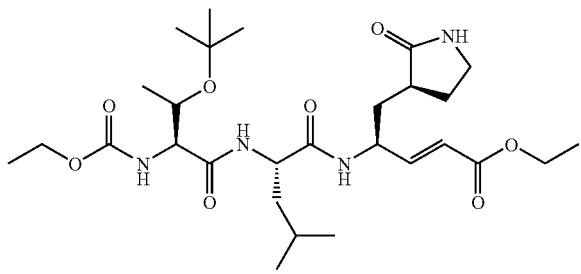

-continued
Compound 65
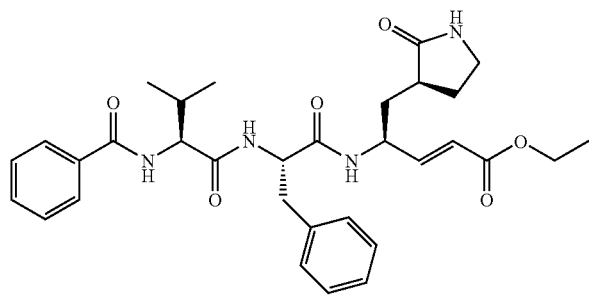
Compound 66
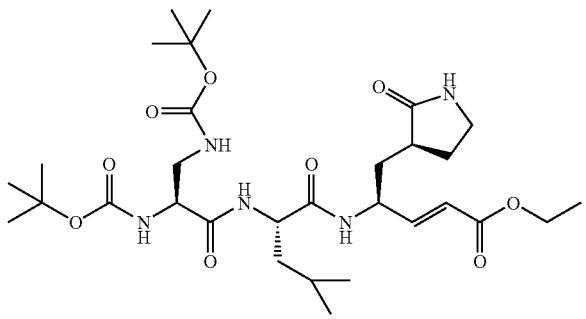
Compound 67
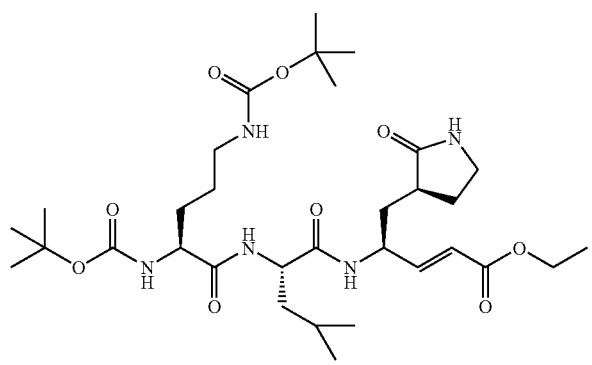
Compound 68
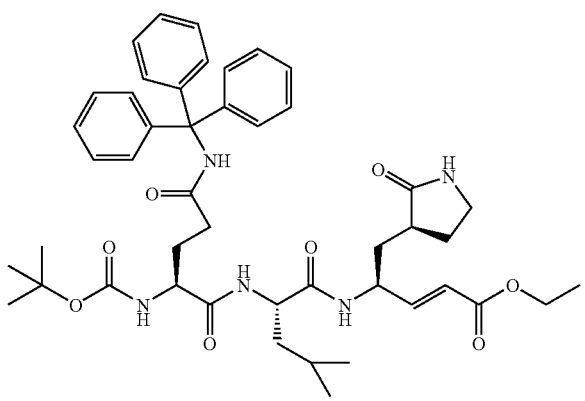
Compound 69
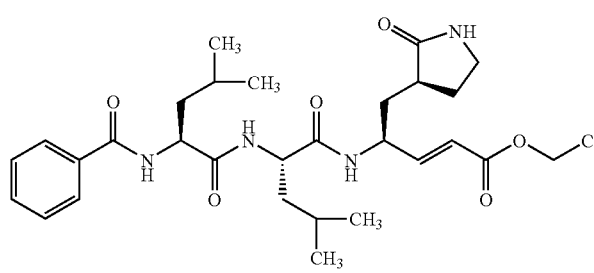
Compound 70
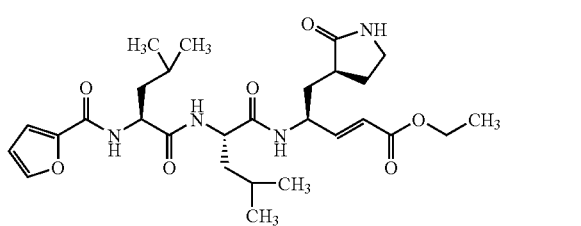
Compound 71
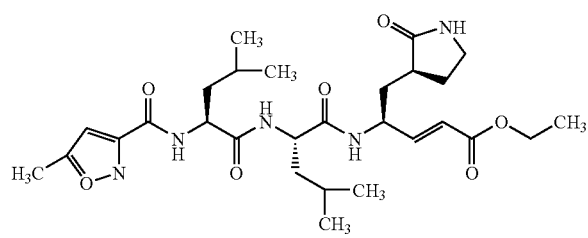
Compound 72
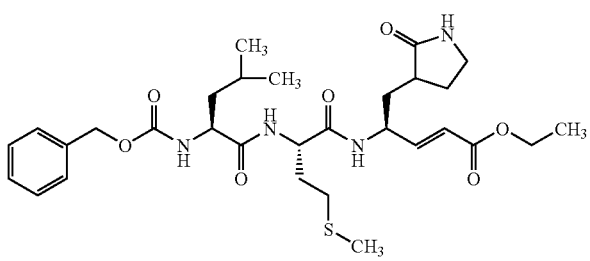
Compound 73
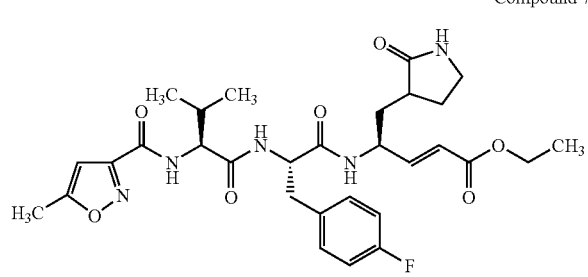
Compound 74
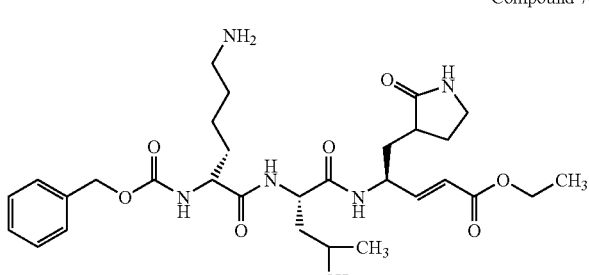

-continued
Compound 75
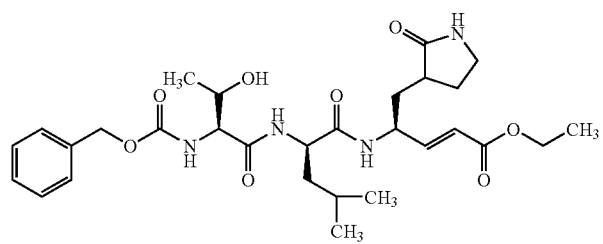
Compound 76
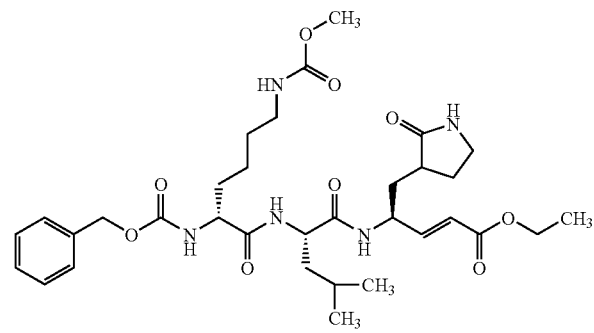
Compound 77
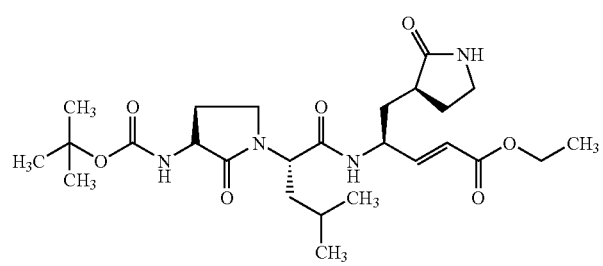
Compound 78
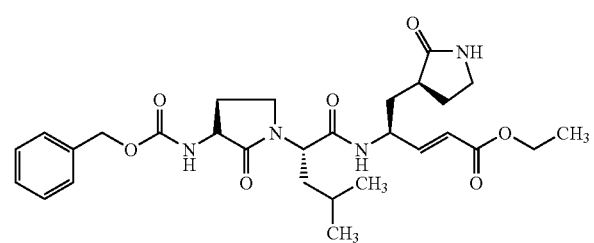
Compound 79
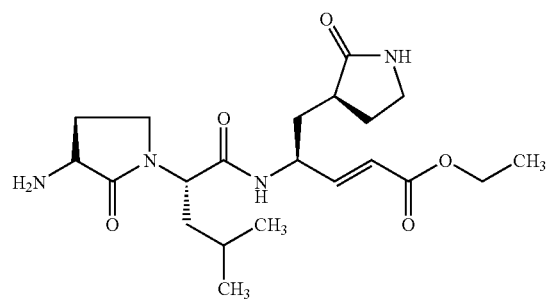
Compound 80
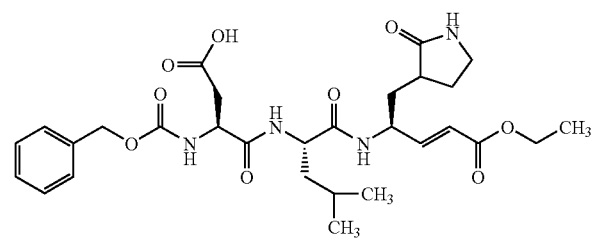
Compound 81
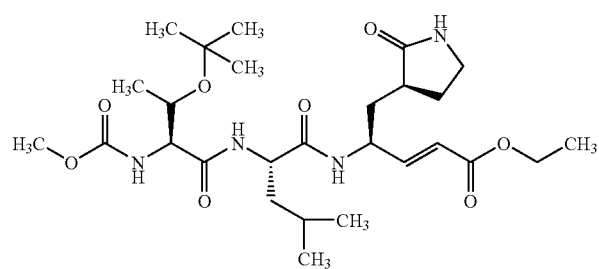
Compound 82
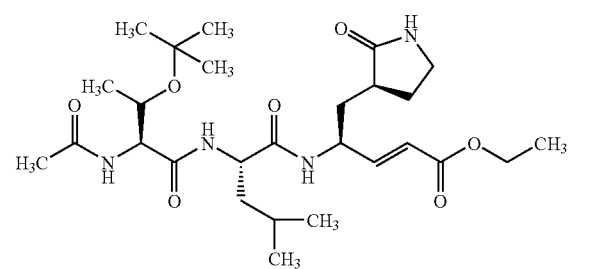
Compound 83
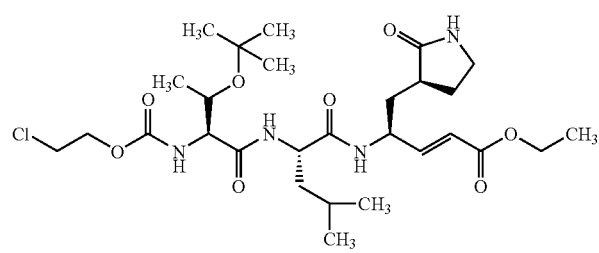
Compound 84
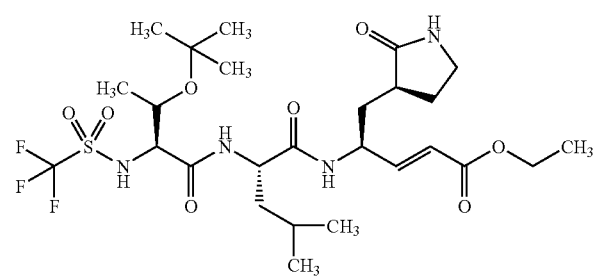

-continued
Compound 85
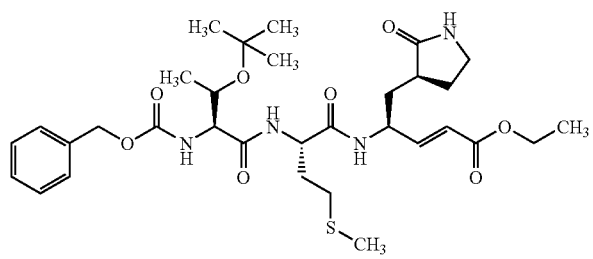
Compound 86
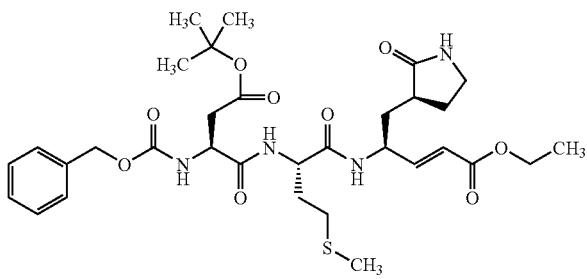
Compound 87
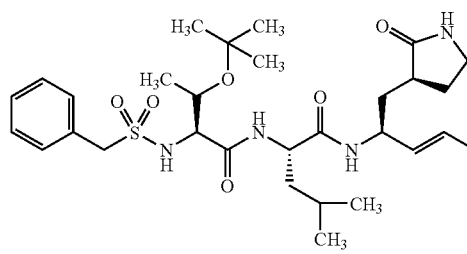
Compound 88
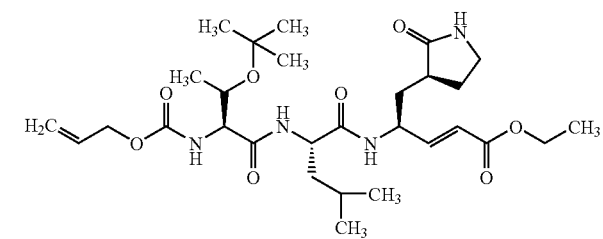
Compound 89
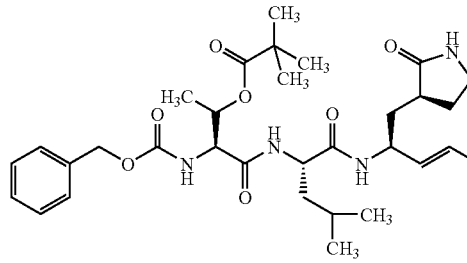
Compound 90
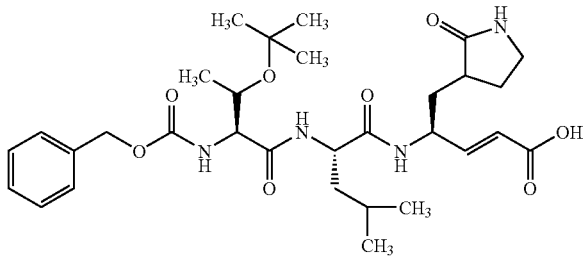
Compound 91
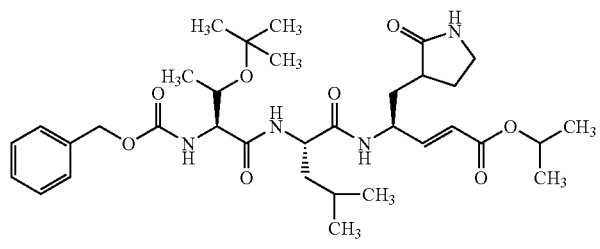
Compound 92
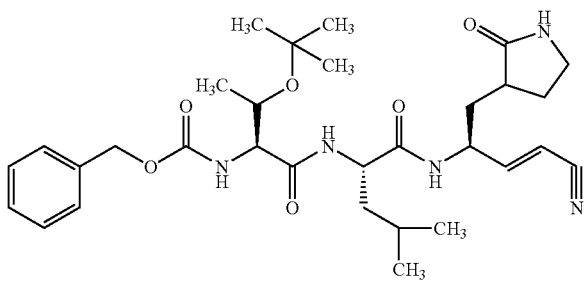
Compound 93
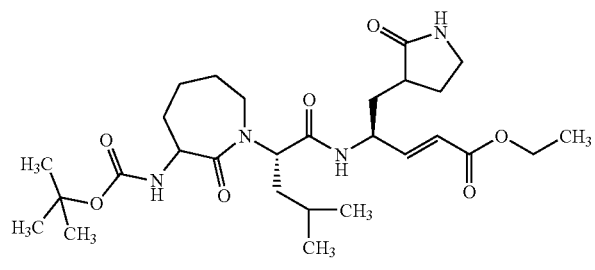
Compound 94
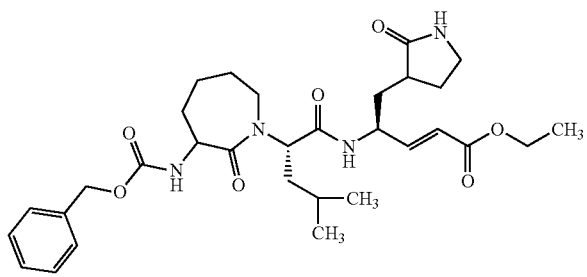

-continued
Compound 95
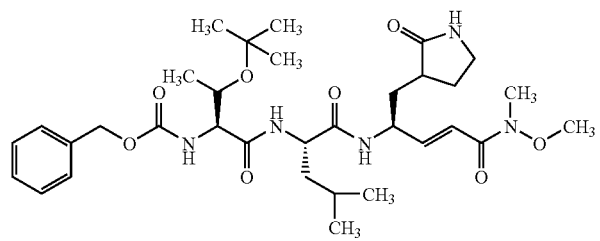
Compound 96
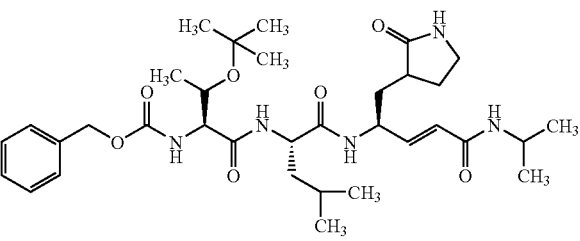
Compound 97
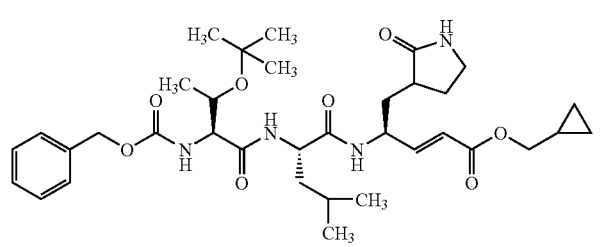
Compound 98
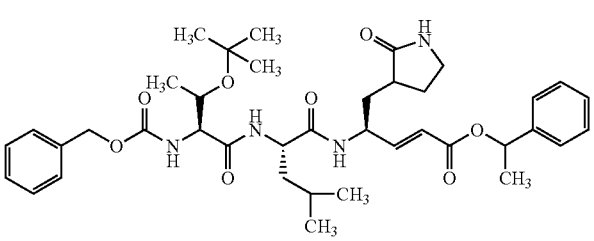
Compound 99
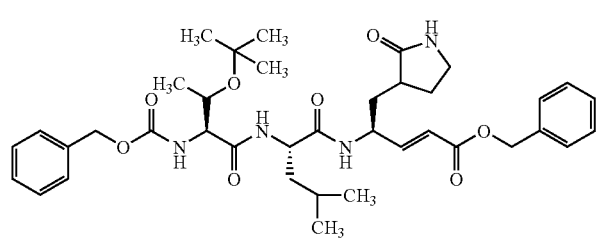
Compound 100
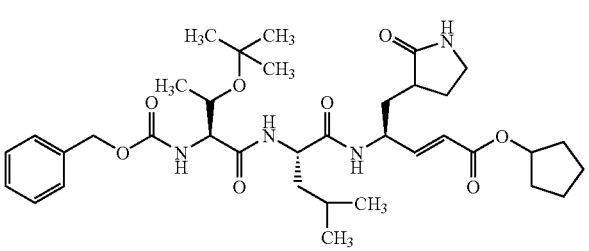
Compound 101
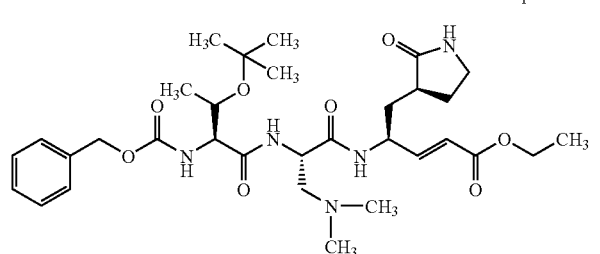
Compound 102
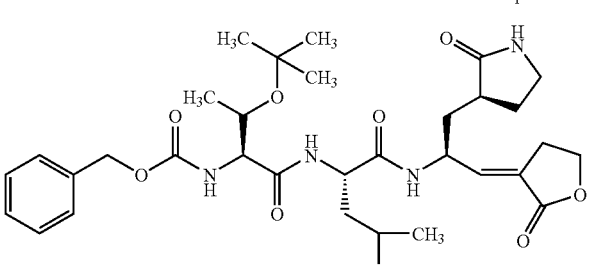
Compound 103
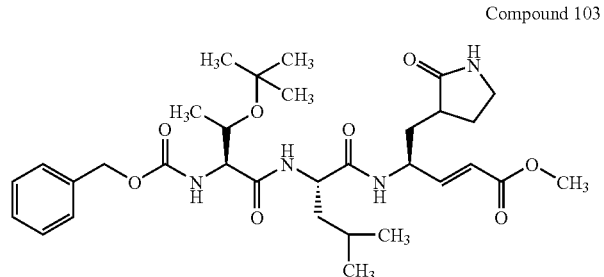
Compound 104
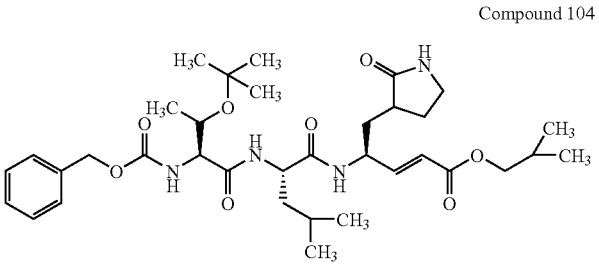
Compound 105
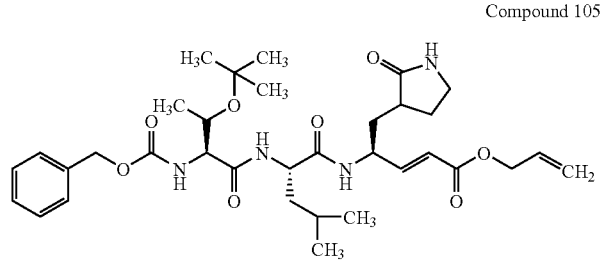
Compound 106
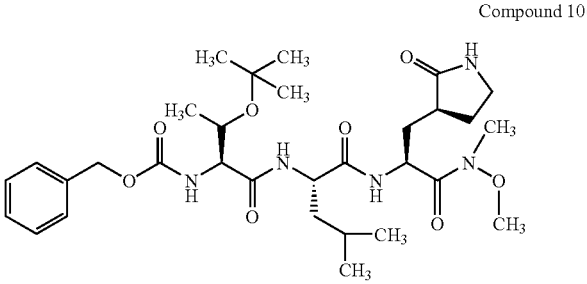

-continued
Compound 107
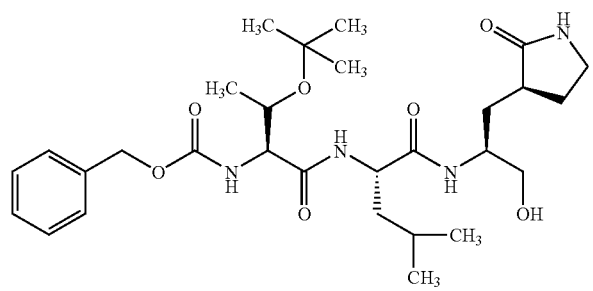
Compound 108
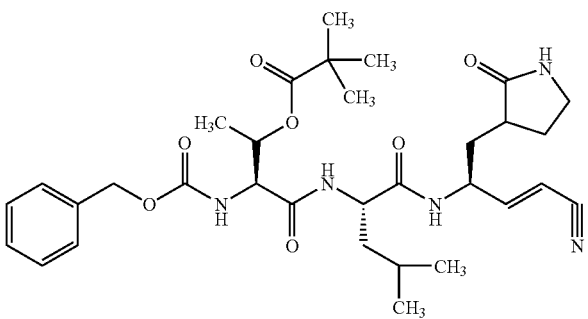
Compound 109
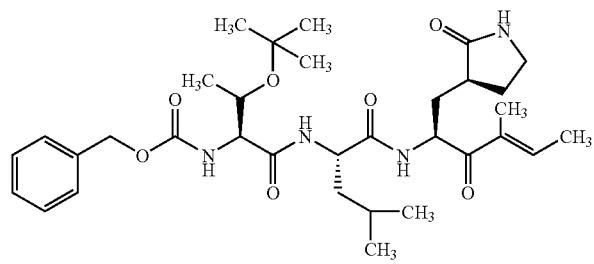
Compound 110
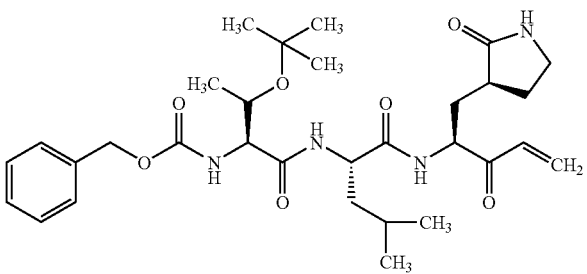
Compound 111
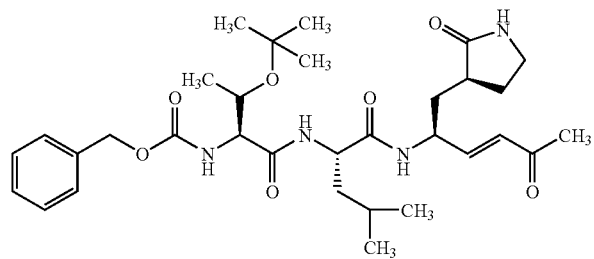
Compound 112
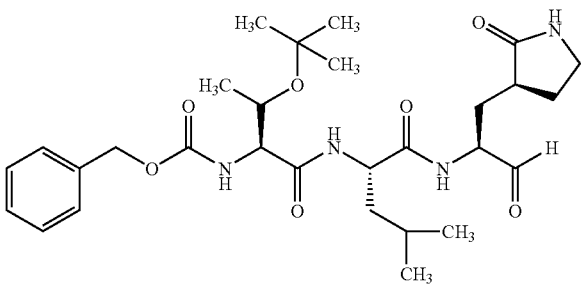
Compound 113
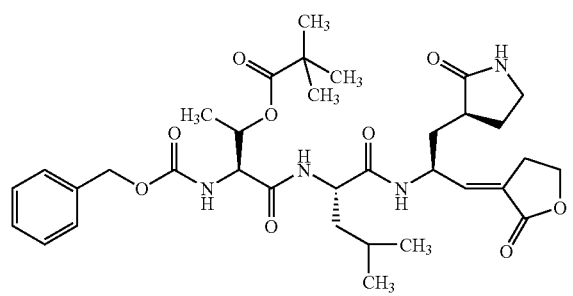
Compound 114
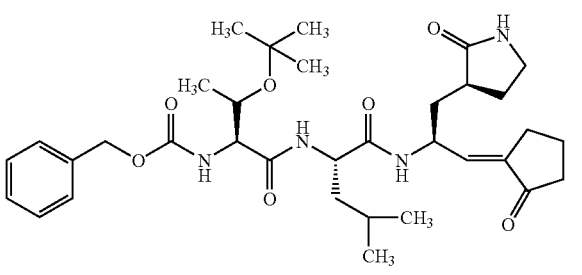
Compound 115
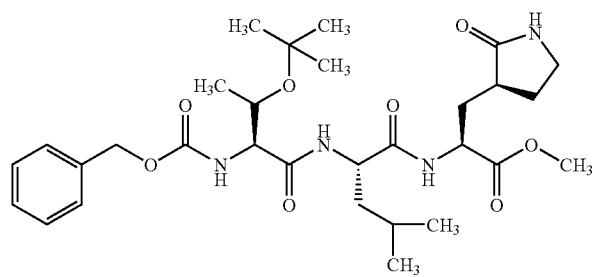
Compound 116
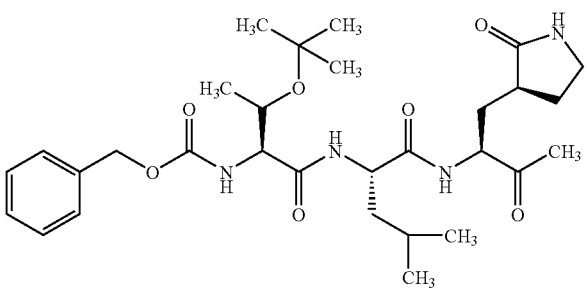

-continued
Compound 117 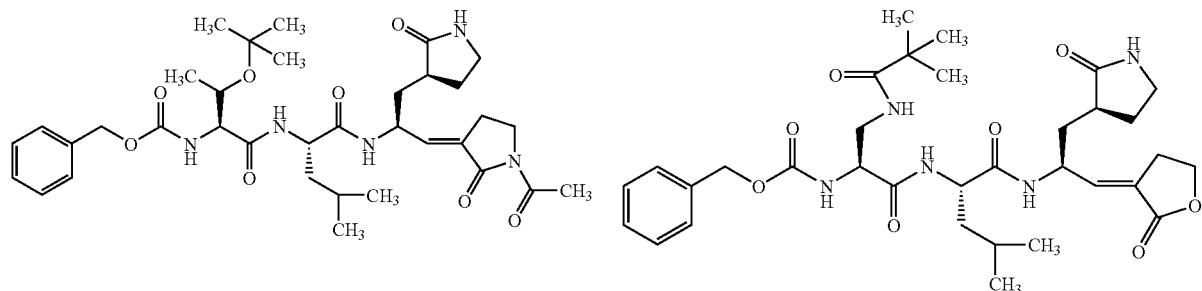 Compound 118
Compound 119 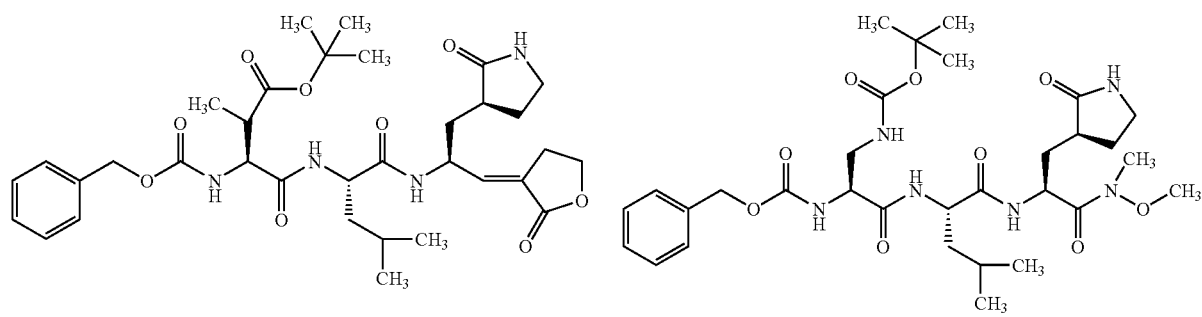 Compound 120
Compound 121 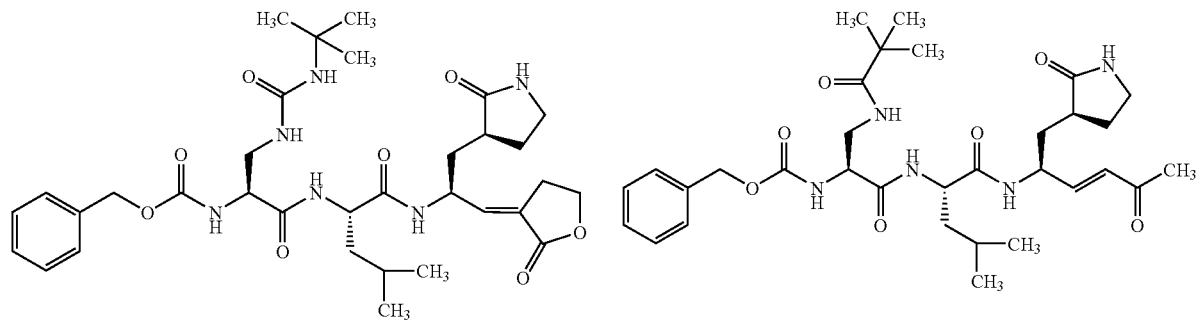 Compound 122
Compound 123 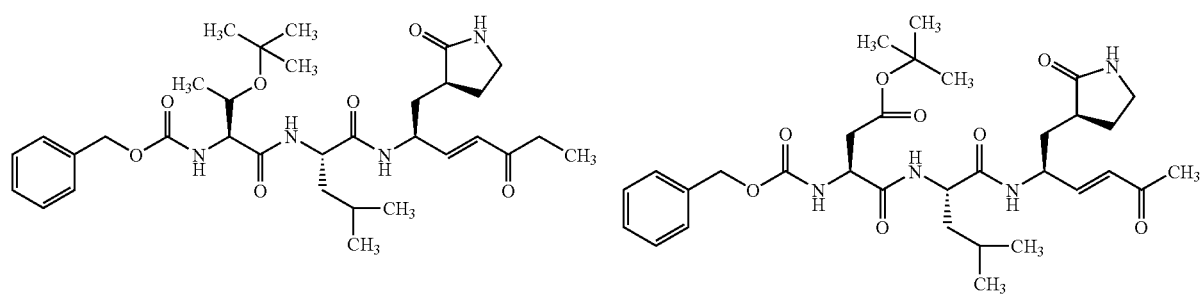 Compound 124
Compound 125 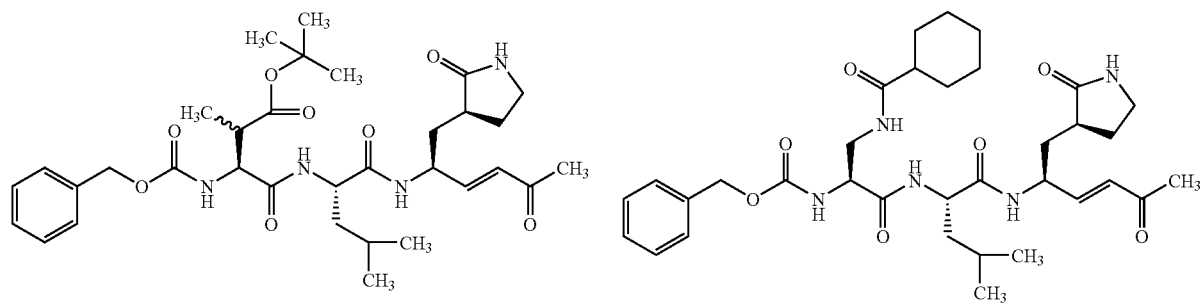 Compound 126

-continued
Compound 127
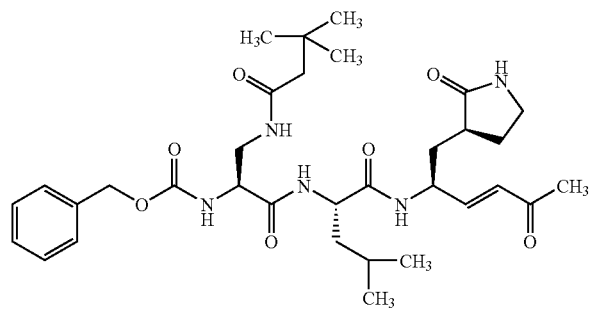
Compound 128
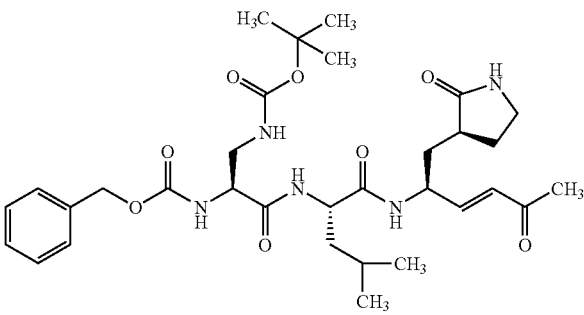
Compound 129
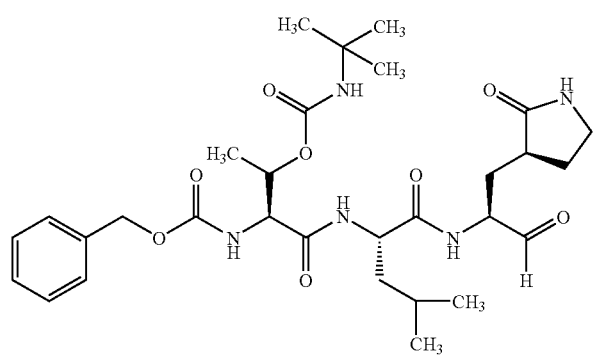
Compound 130
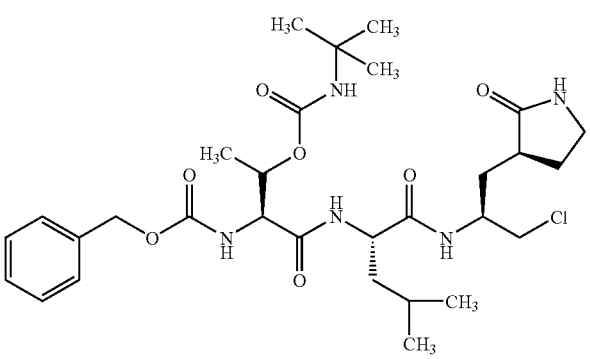
Compound 131
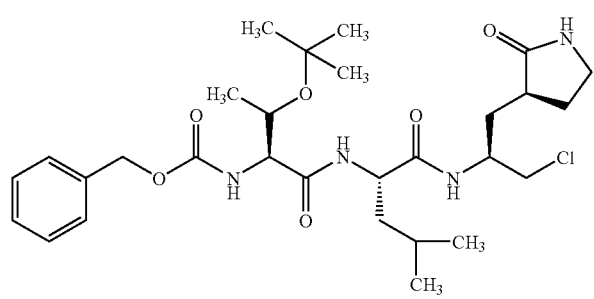
Compound 132
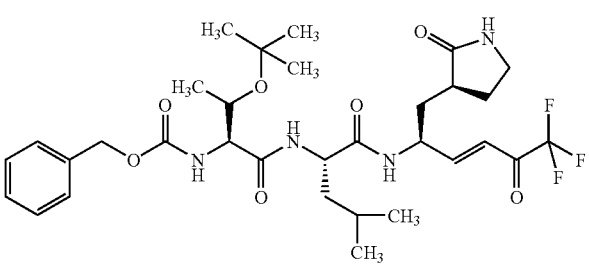
Compound 133
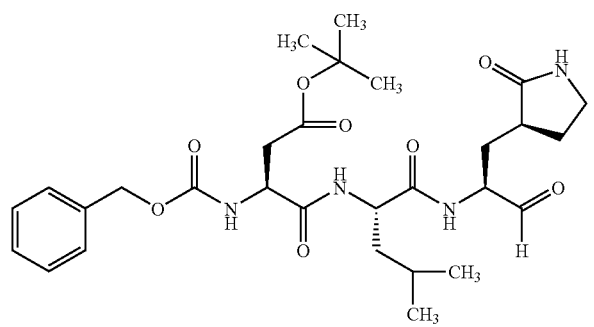
Compound 134
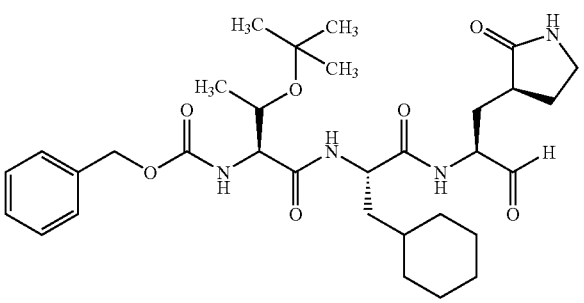
Compound 135
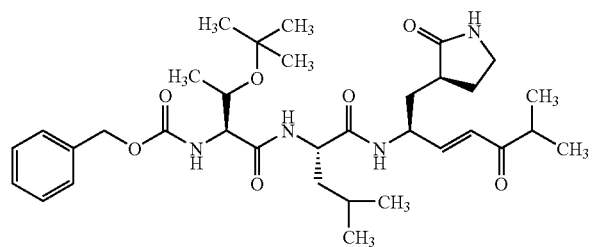
Compound 136
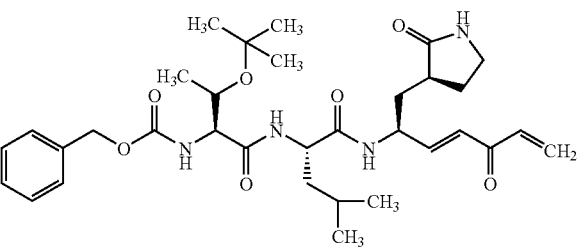

-continued
Compound 137
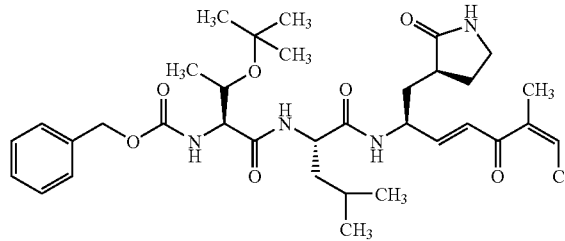
Compound 138
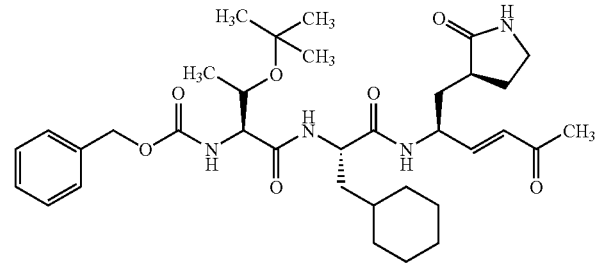
Compound 139
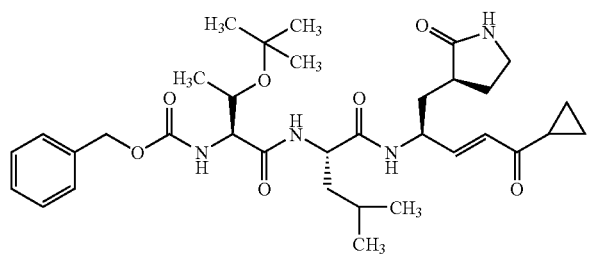
Compound 140
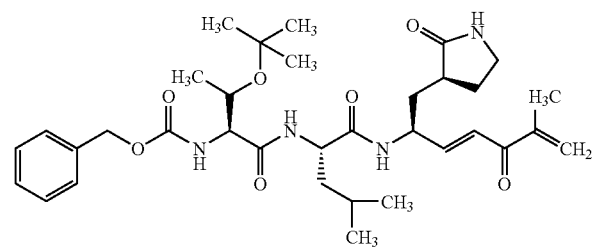
Compound 141
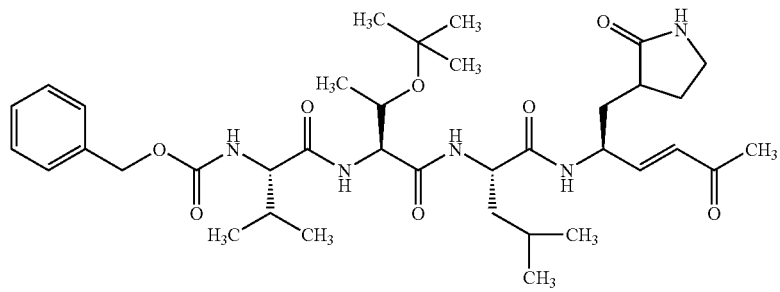
Compound 142
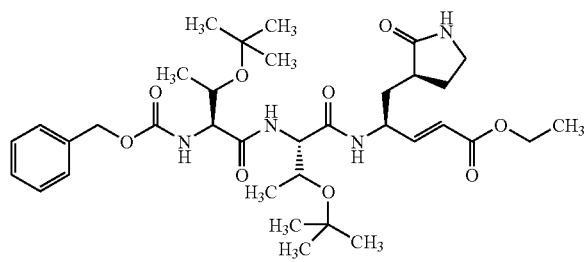
Compound 143
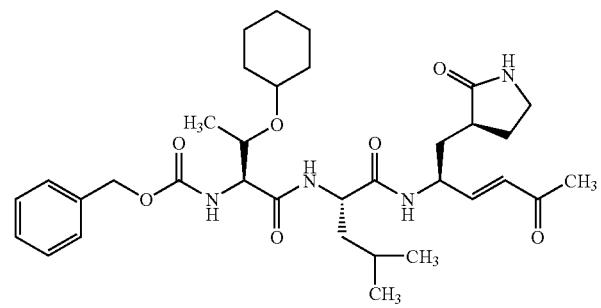
Compound 144
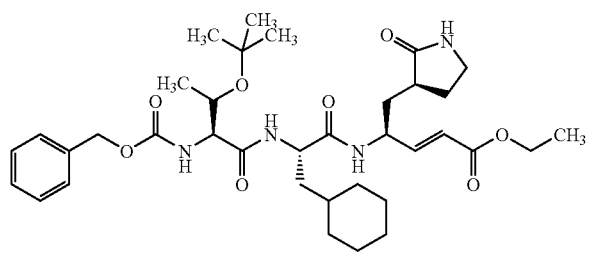
Compound 145
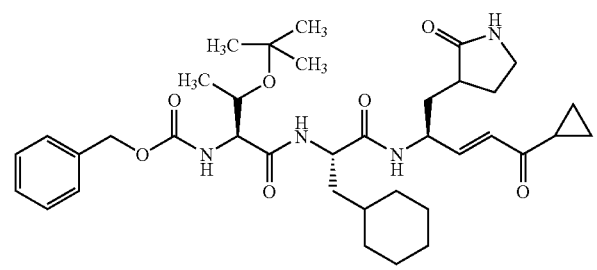

The compounds described above can be prepared by methods well known to a skilled person in the art. For example, Schemes I-IV shown below depict typical synthetic routes for preparing exemplary compounds. In these schemes, $R_1$, $R_1'$, $R_2$, and $R_5$ are as defined in the Summary section above. Details of preparation of these compounds are provided in Examples 1-145.
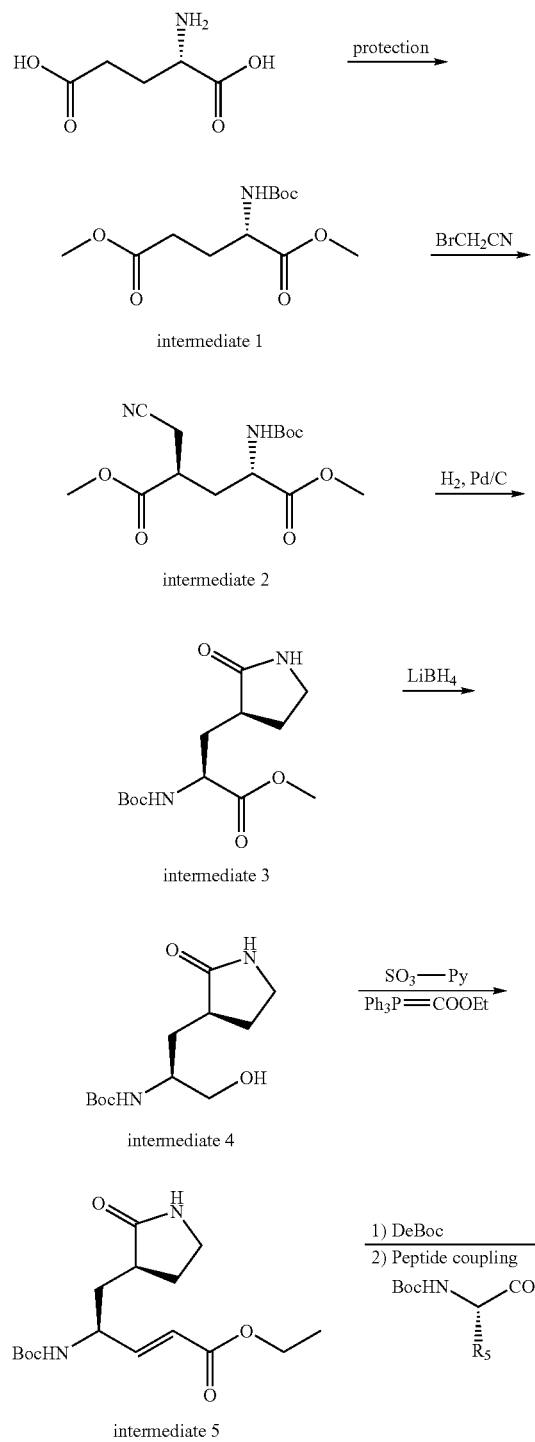
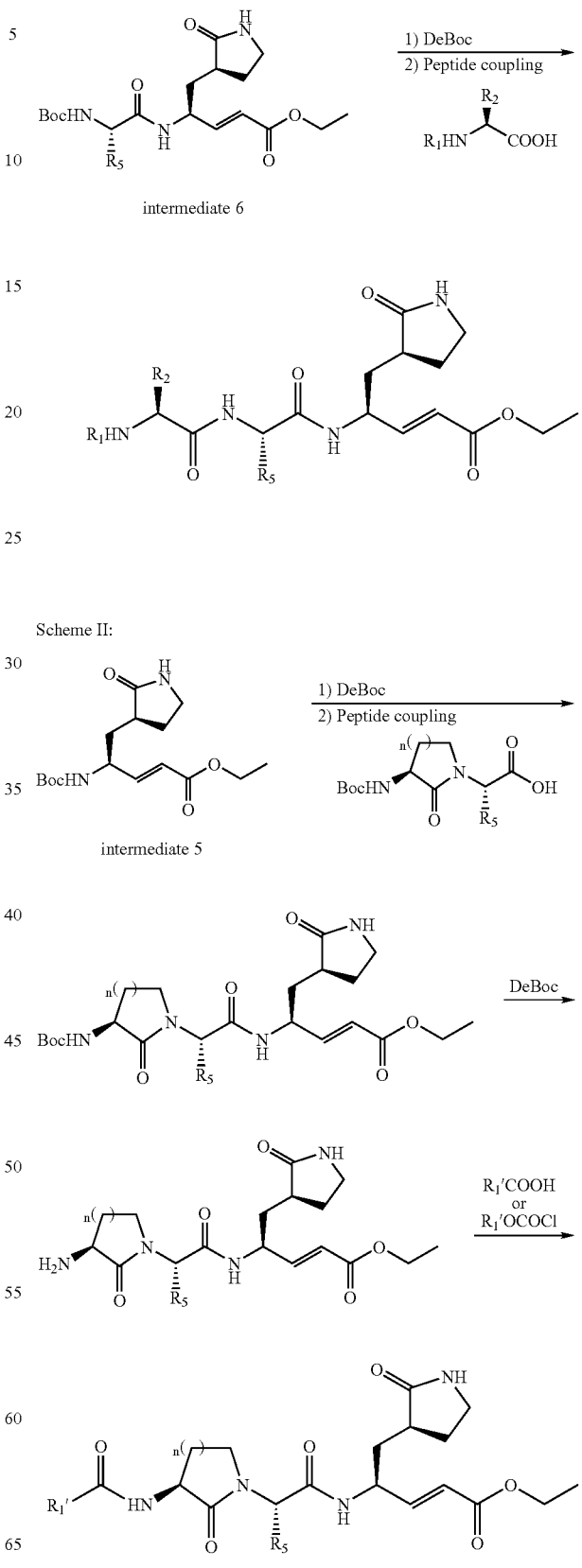

Scheme III:
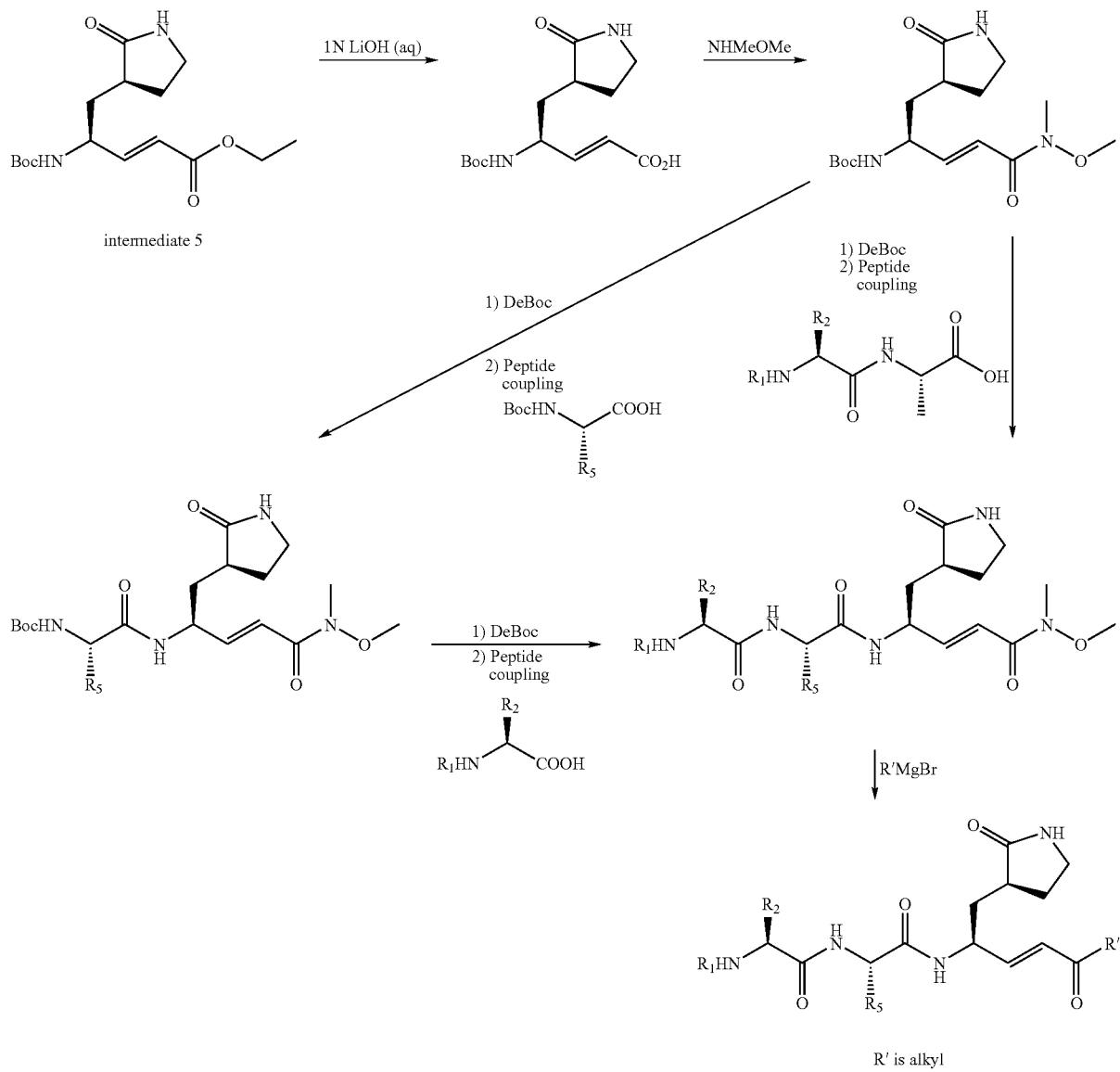
Scheme IV:
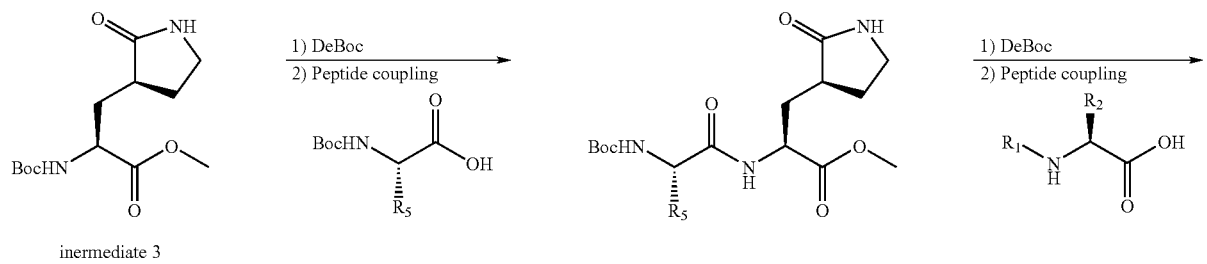

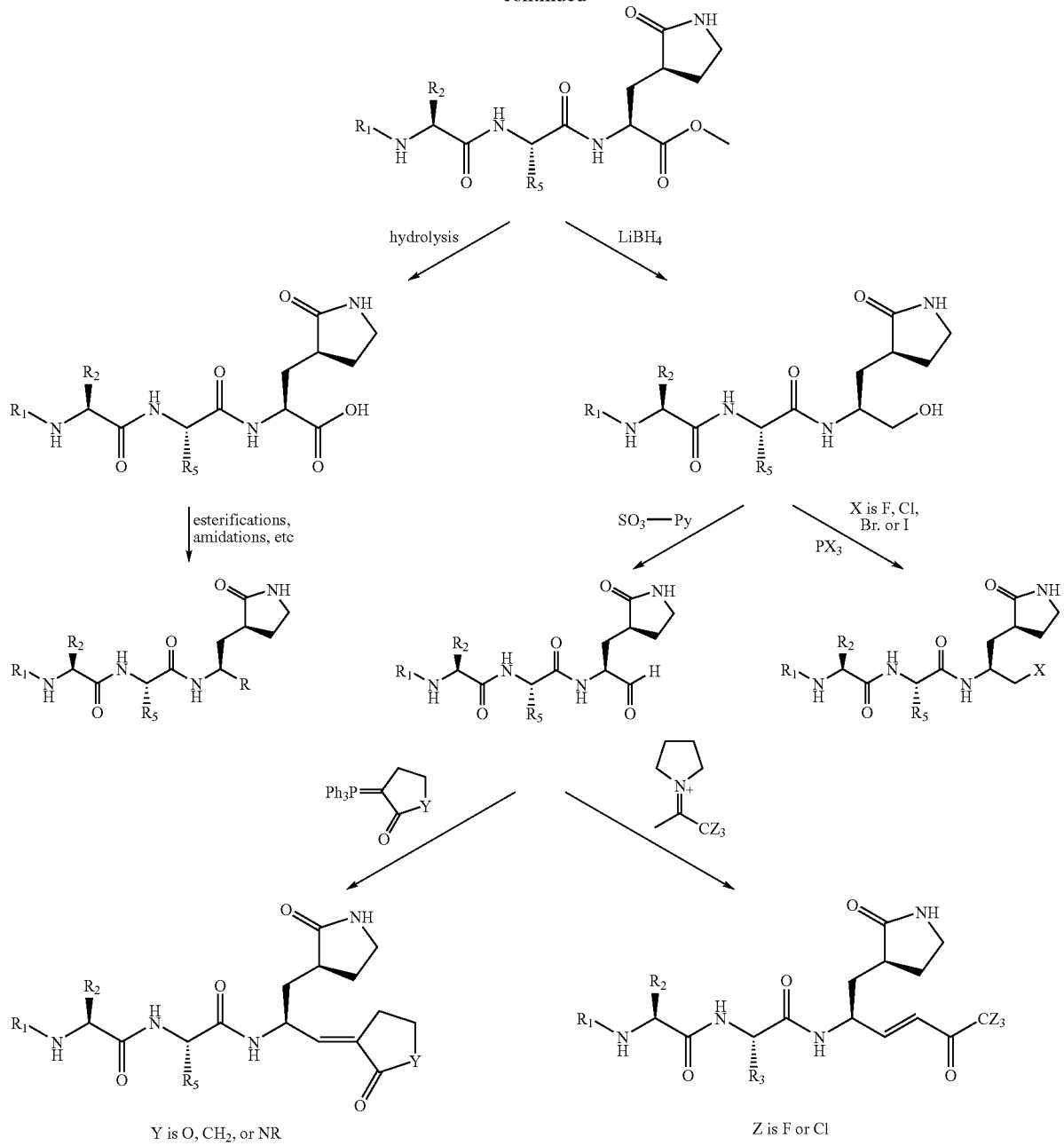

As shown in Scheme I, L-glutamic acid can first be protected with t-butoxylcarbonyl and methyl. The protected L-glutamic acid (intermediate 1) can then react with bromoacetonitrile and followed by a ring closure reaction to form an amino acid derivative that containing a 5-membered cyclic lactam (intermediate 3). Intermediate 3 can subsequently be transformed to intermediate 5 that includes an additional double bond. Intermediate 5 thus formed can sequentially couple with two amino acid derivatives to prepare a compound of formula (I). Reagents other than those shown in Scheme I can also be used. For example, intermediate 5 mentioned above can couple with an acid containing hydroxyl, before coupling to an amino acid to prepare a compound of formula (I) in which X is oxygen.

As shown in Scheme II, intermediate 5 can also couple with amino acid derivatives that contain a pyrrolidinone moiety to form certain compounds of formula (IX). The compounds thus obtained can be further modified (e.g., by reacting with an acid or an acyl chloride) to obtain compounds of formula (X).

As shown in Scheme III, intermediate 5 can also be hydrolyzed to form an acid, which in turn can react with O,N-dimethyl-hydroxylamine to form an amide. The amide can either sequentially couple with two amino acid derivatives or couple with a dipeptide derivative to form certain compounds of formula (I). The compounds thus obtained can further react with Grignard reagents to form other compounds of formula (I).

As shown in Scheme IV, intermediate 3 mentioned above can also sequentially couple with two amino acid derivatives (or couple with a dipeptide derivative) to form certain compounds of formula (I). The compounds thus obtained can be further reduced to form alcohols or oxidized to form acids. The alcohols can be further halogenated to form halides or oxidized to form aldehydes. The aldehydes can subsequently undergo either Wittig reactions or addition-elimination reactions to form certain compounds of formula (II). The acids just-mentioned can undergo, e.g., esterification reactions, Grignard reactions, or amidation reactions to form other compounds of formula (II).

A compound synthesized by the methods described above can be purified by a known method, such as column chromatography, high-pressure liquid chromatography, or recrystallization.

Other compounds of the invention can be prepared using other suitable starting materials following the synthetic routes disclosed herein and/or other synthetic methods known in the art. The methods described above may also additionally include steps, either before or after the steps described specifically herein, to add or remove suitable protecting groups in order to ultimately allow synthesis of the compounds of the invention. In addition, various synthetic steps may be performed in an alternate sequence or order to give the desired compounds. Synthetic chemistry transformations and protecting group methodologies (protection and deprotection) useful in synthesizing applicable compounds of the invention are known in the art and include, for example, those described in R. Larock, Comprehensive Organic Transformations, VCH Publishers (1989); T. W. Greene and P. G. M. Wuts, Protective Groups in Organic Synthesis, 2nd Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

The compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition contains an effective amount of at least one compound described above and a pharmaceutical acceptable carrier. Further, this invention covers a method of administering an effective amount of one or more of the compounds of the invention to a patient having an infection with a coronavirus or a flaviviridae virus. Effective doses will vary, as recognized by those skilled in the art, depending on the types of diseases treated, route of administration, excipient usage, and the possibility of co-usage with other therapeutic treatment.

To practice the method of the present invention, a composition having one or more compounds of the invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more compounds of the invention can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of a compound of the invention. Examples of other carriers include colloidal silicon oxide, magnesium stearate, cellulose, sodium lauryl sulfate, and D&C Yellow #10.

The compounds of this invention can be preliminarily screened for their efficacy in treating an infection with a virus by an in vitro assay (See Example 146 below) and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of Compound 1

TMSCl (190 mL, 4.4 eq) was slowly added to a stirred suspension of L-glutamic acid (50.0 g, 1 eq.) in dry MeOH (1100 mL, 0.3 M) surrounded by an ice-cold bath. After the addition was complete, the ice-clod bath was removed and the reaction was stirred overnight until TLC showed completed conversion. Then, Et₃N (306 mL, 6.5 eq) and (Boc)₂O (82 g, 1.1 eq) were added sequentially to the above reaction mixture. The reaction mixture was then stirred until TLC showed complete protection. The solvent was then removed under reduced pressure. The residue was then filtered and washed with Et₂O using a pad of celite. The organic layers were combined and concentrated. The resulting crude product was purified by silica gel column chromatography to afford intermediate 1, N-Boc-L-(+)-glutamic acid dimethyl ester, (88 g, 95%) as an oil: $^1$H NMR (CDCl₃) δ 1.40 (s, 9H), 1.91 (m, 1H), 2.14 (m, 2H), 2.37 (m, 2H), 3.64 (s, 3H), 3.70 (s, 3H), 4.29 (br, s, 1H). ESI-MS (M+H$^+$)=276.

To a solution of intermediate 1 (20 g, 1 eq.) in THF (50 mL) was added dropwise a solution of lithium hexamethyldisilazide (2.2 eq.) in THF (250 mL) at −78° C. under nitrogen atmosphere. The resulting mixture was stirred at −78° C. for another 1.5 hours. Bromoacetonitrile (13 g, 1.5 eq.) was added dropwise to the above solution over a period of 1 hour while maintaining the temperature below −70° C. using a cooling bath. The reaction mixture was stirred at −78° C. for additional for 1-2 hours and the disappearance of the starting material was confirmed by TLC analysis. The reaction was then quenched with pre-cooled methanol (10 mL) stirred for 10 minutes. The resulting methoxide was then quenched with a pre-cooled acetic acid in THF solution (9 mL HOAc/60 mL THF). After stirred for another 10 minutes, the cooling bath was removed and replaced with water bath. The reaction mixture was allowed to warm up to 0±5° C. and then poured into brine solution (10 g of NaCl in 100 mL water) in a 1 L extractor. The organic layer was separated and concentrated to afford a dark brown oil. Silica gel (25 g) and methylene chloride (60 mL) were added to the Rotovap flask and spun on a Rotovap for 1 hour without heat and vacuum. The slurry was then filtered and wash with another batch of methylene chloride (100 mL). The light brown filtrate was collected, concentrated, and purified by silica gel column chromatography to afford intermediate 2 (19 g), 2-tert-butoxycarbonyl-amino-4-cyanomethyl-pentanedioic acid dimethyl ester. $^1$H NMR (CDCl₃) δ 1.42 (s, 9H), 2.10-2.17 (m, 2H), 2.77-2.90 (m, 3H), 3.73 (s, 3H), 3.74 (s, 3H), 4.32-4.49 (m, 1H), 5.12 (d, J=6.0 Hz, 1H). ESI-MS (M+H$^+$)=315.

Intermediate 2 (10 g) was dissolved in HOAc (240 mL) and shaken with 10% Pd/C (20 g) under H₂ gas (70 psi) for 2 days. The mixture was filtered over celite. The filtrate was evaporated under reduced pressure and the residue was repeatedly evaporated from methyl tert-butyl ether to yield a light pink solid. The crude product was dissolved in THF and then Et₃N (20 mL) was added to the solution. The resulting mixture was stirred at 60° C. overnight. The reaction was quenched with by addition of H₂O (50 mL). The organic layer was separated and the aqueous layer was further extracted with methylene chloride. The organic layers were then combined, concentrated, and purified by silica gel column chromatography to afford intermediate 3, 2-tert-butoxycarbonylamino-3-(2-oxo-pyrrolidin-3-yl)-propionic acid methyl ester. $^1$H NMR (CDCl₃) δ 1.37 (s, 9H), 1.75-1.80 (m, 2H), 2.04-2.09 (m, 1H), 2.39-2.42 (m, 1H), 3.25-3.29 (m, 2H), 3.67 (s, 3H), 4.23-4.26 (m, 1H), 5.47 (d, J=8.0 Hz, 1H), 6.29 (s, 1H). ESI-MS (M+H$^+$)=287.

Intermediate 3 (6.0 g, 18.4 mmol) was solved in THF (200 mL) surrounded by an ice bath, followed by addition of 2.0 M LiBH₄/THF (46 ml, 5.0 eq). The ice bath was then removed and the mixture was stirred for 2 hours at room temperature. To the mixture was sequentialled added water (200 mL), ethyl acetate (200 mL), and MgSO₄ (400 g). Then MgSO₄ was removed and the aqueous layer was extracted with ethyl acetate. The organic layers were combined and concentrated to afford intermediate 4, [2-hydroxy-1-(2-oxo-pyrrolidin-3-ylmethyl)-ethyl]-carbamic acid tert-butyl ester, as a white solid (5.2 g, 95%). ESI-MS (M+H$^+$)=259.

Triethylamine (0.7 mL) was added to a solution of intermediate 4 (0.59 g, 2.28 mmol, 1 eq.) in methylsulfoxide (10.5 mL). The resulting solution was cooled to 15° C. using an ice-water bath and then sulfur trioxide-pyridine complex (1.8 g, 5 eq.) was added. The reaction was stirred at that temperature for 1 hour.

(Carboethoxymethylenetriphenyl)-phosphorane (2.4 g, 3 eq.) was added and the reaction was stirred at ambient temperature for another 3 hours. The reaction was then quenched by saturated brine (150 mL) and extracted with ethyl acetate (3×50 mL). The organic layers were combined, dried over anhydrous MgSO₄, filtered, and concentrated to afford a dark red oil. The oil was purified though column chromatography (50% ethyl acetate in hexane) to afford intermediate 5, 4-tert-butoxycarbonylamino-5-(2-oxo-pyrrolidin-3-yl)-pent-2-enoic acid ethyl ester, as a white solid (0.34 g, 45.7%). $^1$H NMR (CDCl₃) δ 1.21 (t, 3H, J=7.2), 1.36 (s, 9H), 1.48-1.57 (m, 1H), 1.66-1.79 (m, 1H), 1.90-1.97 (m, 1H), 2.38-2.47 (m, 2H), 3.26-3.29 (m, 2H), 4.10(q, 2H, J=6.9), 4.27(s, br, 1H), 5.46(d, 1H, J=7.5), 5.87 (d, 1H, J=15.6), 6.78 (dd, 1H, J=15.3, J=5.4), 6.98(s, br, 1H). ESI-MS (M+H$^+$)=577.

Intermediate 5 (100 mg, 0.3 mmol) was added to a solution of HCl in 1,4-dioxane (4.0 M, 3 mL) and the solution was stirred at room temperature for 30 minutes. The resulting solution was concentrated by removing 1,4-dioxane. CH₂Cl₂ (3 mL) was then added to the residue thus obtained and the solution was cooled down to 0-5° C. N-Methylmorpholine (0.13 mL, 4 eq.) was then added and the mixture was stirred for 10 minutes to form solution (a). Boc-L-Leu-OH (71 mg, 0.3 mmol) was mixed with 1,1-ethyl-3-(3-dimethylamino-propyl)carbodiimide (EDC, 70 mg, 1.2 eq.) and N-hydroxybenzotriazole (HOBt, 50 mg, 1.2 eq.) in CH₂Cl₂. The mixture was stirred for 20 minutes to form solution (b). Solution (a) was then added to solution (b) and the mixture was stirred at room temperature for 2 hours. The reaction residue was added with brine (25 mL) and extracted with ethyl acetate (3×5 mL). The organic layers were combined, dried over anhydrous MgSO₄, and concentrated. The residue was purified by flash column chromatography (3% MeOH in CH₂Cl₂) to afford intermediate 6, 4-(2-tert-butoxycarbonylamino-4-methyl-pentanoylamino)-5-(2-oxo-pyrrolidin-3-yl)-pent-2-enoic acid ethyl ester, as a white solid. $^1$H NMR (CDCl₃) δ 0.94 (d, 6H, J=5.1 Hz), 1.26 (t, 3H, J=7.2 Hz), 1.43 (s, 9H), 1.66-1.73 (m, 5H), 2.41 (br s, 1H), 3.33 (d, 2H, J=8.1 Hz), 4.16 (q, 2H, J=6.9 Hz), 4.58 (br, s, 1H), 5.03 (br, s, 1H), 5.9 (d, 1H, J=15.6 Hz), 6.82 (dd, 1H, J=15.3 Hz, 5.1 Hz), 7.50 (br, s, 1H). ESI-MS (M+H$^+$)=440.

Intermediate 7 (compound 6) was prepared in 60% yield from 2-benzyloxycarbonyl-amino-3-tert-butoxy-butyric acid and intermediate 6 using the procedure similar to that described in the preceding paragraph. $^1$H NMR (CDCl₃) δ 0.94-0.98 (m, 6H), 1.07 (d, 3H, J=6.3), 1.27 (s, 9H), 1.66-1.73 (m, 5H), 2.21-2.50 (m, 2H), 3.20-3.30 (m, 2H), 4.16 (q, 2H, J=6.9 Hz), 4.42 (br, s, 1H), 4.58 (br, s, 1H), 5.10 (s, 2H), 5.9 (d, 1H, J=15.6 Hz), 6.82 (dd, 1H, J=15.3 Hz, 5.1 Hz), 7.2-7.34 (m, 4H), 7.60 (d, 1H, J=7.5 Hz). ESI-MS (M+H$^+$)=631.

Compound 1 was prepared by treating intermediate 7 with trifluoroacetic acid (2 mL). $^1$H NMR (CDCl₃) δ 0.89-0.93 (m, 6H), 1.13-1.15 (m, 3H), 1.22-1.27 (m, 3H), 1.55-1.76 (m, 4H), 1.95-2 (m, 1H), 2.03-2.46 (m, 2H), 3.28-3.30 (m, 2H), 4.11-4.18 (m, 3H), 4.33 (br s, 1H), 4.54-4.56 (br s, 2H), 5.07 (s, 2H), 5.84-5.94 (d, 1H, J=15.9 Hz), 6.03-6.06 (d, J=7.2 Hz), 6.76-6.83 (dd, 1H, J=15.0 Hz, 5.4 Hz), 7.31 (br s, 5H), 8.02 (br s, 1H). ESI-MS (M+H$^+$)=575.

EXAMPLE 2

Preparation of Compound 2

Compound 2 was prepared in a manner similar to that described in Example 1.

$^1$H NMR (CDCl$_3$) δ 7.92 (d, J=7.5 Hz, 1H), 7.24-7.38 (m, 5H), 6.78 (dd, J=15, 2.7 Hz, 1H), 5.98 (d, J=7.8 Hz, 1H), 5.89 (d, J=15 Hz, 1H), 5.09 (d, J=4.2 Hz, 1H), 5.07 (s, 2H), 4.60-4.78 (m, 1H), 4.43-4.53 (m, 2H), 4.21-4.38 (m, 1H), 4.17 (q, J=5.1 Hz, 2H), 3.82-3.88 (m, 1H), 3.40-3.71 (m, 2H), 3.29 (m, 2H), 1.40-2.11 (m, 5H), 1.25 (t, J=5.1 Hz), 0.90 (br s, 6H). ESI-MS (M+H$^+$)=561.

EXAMPLE 3

Preparation of Compound 3

Compound 3 was prepared in a manner similar to that described in Example 1.

$^1$H NMR (CDCl$_3$) δ 0.91(s, br, 6H), 1.27(t, 3H, J=6.0), 1.60-1.66(m, 5H), 1.97-2.44(m, 7H), 3.26(m, 2H), 4.17(q, 2H, J=6.9), 4.24(m, 1H), 4.60(m, 1H), 5.06(s, 2H), 5.92(d, 1H, J=15.3), 6.12-6.18(m, 2H), 6.62-6.70(m, 1H), 6.83(dd, 1H, J=15.3, 5), 7.31(s, br, 5H), 7.56(m, 1H), 8.01(m, 1H). ESI-MS (M+Na$^+$)=623.9.

EXAMPLE 4

Preparation of Compound 4

Compound 4 was prepared in a manner similar to that described in Example 1.

$^1$H NMR (CDCl$_3$) δ 7.82 (d, J=8.0 Hz, 1H), 6.90 (d, J=7.5 Hz, 1H), 6.82 (dd, J=15, 5.4 Hz, 1H), 5.89 (m, 4H), 5.09 (m, 2H), 4.40-4.68 (m, 2H), 4.16 (q, J=7.5 Hz, 2H), 3.32 (m, 2H), 2.03-2.51 (m, 2H), 1.50-2.03 (m, 1OH), 1.43 (s, 9H), 1.69 (t, J=7.5 Hz, 3H), 0.94 (d, J=6.0 Hz, 3H), 0.92 (d, J=6.0 Hz, 3H). ESI-MS (M+H$^+$)=659.

EXAMPLE 5

Preparation of Compound 5

Compound 5 was prepared in a manner similar to that described in Example 1.

$^1$H NMR (CD$_3$OD) δ 0.86-1.04 (m, 6H), 1.23 (s, br, 3H), 1.60-1.71 (m, 6H), 2.06-2.85 (m, 6H), 3.38 (m, 2H), 4.10-4.28 (m, 2H), 4.34-4.45 (m, 1H), 4.60-4.72 (m, 1H), 5.13 (s, 2H), 5.91 (d, 1H, J=15.9), 6.82 (dd, 1H, J=15.9, 4.7), 7.27-7.54 (m, 5H). ESI-MS (M+H$^+$)=589.

EXAMPLE 6

Preparation of Compound 6

Compound 6 was prepared in a manner identical to that of intermediate 7 described in Example 1.

$^1$H NMR (CDCl$_3$) δ 0.94-0.98 (m, 6H), 1.07 (d, 3H, J=6.3), 1.27 (s, 9H), 1.66-1.73 (m, 5H), 2.21-2.50 (m, 2H), 3.20-3.30 (m, 2H), 4.16 (q, 2H, J=6.9 Hz), 4.42 (br, s, 1H), 4.58 (br, s, 1H), 5.10 (s, 2H), 5.9 (d, 1H, J=15.6 Hz), 6.82 (dd, 1H, J=15.3 Hz, 5.1 Hz), 7.2-7.34 (m, 4H), 7.60 (d, 1H, J=7.5 Hz). ESI-MS (M+H$^+$)=631.

EXAMPLE 7

Preparation of Compound 7

Compound 7 was prepared in a manner similar to that described in Example 1.

$^1$H NMR (CDCl$_3$) δ 0.86-0.87 (d, 6H, J=4.2), 1.09 (s, 9H), 1.18-1.22 (t, 3H, J=7.2), 1.66 (m, 5H), 2.30 (s, br, 2H), 3.21-3.24 (d, 2H, J=7.2), 3.35-3.40 (t, 1H, J=6.6), 3.74-3.76 (d, 1H, J=6.9), 4.10 (q, 2H, J=7.2), 4.16 (s, br, 1H), 4.51 (s, br, 2H), 5.03-5.05 (d, 2H, J=4.8), 5.64-5.65 (d, 1H, J=15.9), 6.72-6.77 (dd, 1H, J=4.5), 6.93-6.96 (d, 1H, J=6.9), 7.28 (s, br, 5H), 7.60 (s, br, 1H). ESI-MS (M+H$^+$)=616.

EXAMPLE 8

Preparation of Compound 8

Compound 8 was prepared in a manner similar to that described in Example 1.

$^1$H NMR (CDCl$_3$) δ 7.74 (d, J=7.5 Hz, 1H), 7.24-7.33 (m, 10H), 7.05 (d, J=8.5 Hz, 1H), 6.80 (dd, J=15.5, 5.5 Hz, 1H), 6.17 (s, 1H), 5.90 (d, J=15.5 Hz, 1H), 5.73 (d, J=6.5 Hz, 1H), 5.10 (s, 2H), 4.47-4.62 (m, 4H), 4.27-4.29 (m, 1H), 4.18-4.20 (m, 3H), 3.24-3.27 (m, 2H), 2.23-2.48 (m, 2H), 1.90-2.14 (m, 1H), 1.89 (s, 2H), 1.47-1.73 (m, 3H), 1.26 (t, J=3.6 Hz, 3H), 1.21 (d, J=10.2 Hz, 3H), 0.87 (d, J=8.0 Hz, 3H), 0.85 (d, J=8.0 Hz 3H). ESI-MS (M+H$^+$)=665.

EXAMPLE 9

Preparation of Compound 9

Compound 9 was prepared in a manner similar to that described in Example 1.

ESI-MS (M+H$^+$)=639.

EXAMPLE 10

Preparation of Compound 10

Compound 10 was prepared in a manner similar to that described in Example 1.

$^1$H NMR (CDCl$_3$) δ 0.88-0.98 (m, 6 H), 1.19-1.86 (m, 15H), 2.0-2.08 (m, 1H), 2.15-2.39 (m, 2H), 2.47-2.59 (m, 1H), 2.94 (m, 2H), 3.98-4.20 (m, 3H), 4.30-4.36 (m, 1H), 4.60-4.64 (m, 1H), 5.09 (m, 2H), 5.89 (d, J=15.6,1H), 6.89 (dd, 1H, 15.6, 4.8), 7.26-7.33 (m, 5H). ESI-MS (M+H$^+$)=639.

EXAMPLE 11

Preparation of Compound 11

Compound 11 was prepared in a manner similar to that described in Example 1.

$^1$H NMR (CDCl$_3$) δ 7.90 (d, J=7.0 Hz, 1H), 7.31 (s, 5H), 6.77-6.85 (m, 2H), 6.41 9 (br, s, 1H), 5.90 (d, J=15 Hz, 1H), 5.78 (d, J=7 Hz, 1H), 5.07 (s, 2H), 4.87 (br, s, 1H), 4.41-4.62 (m, 2H), 4.07-4.14 (m, 4H), 3.21-3.37 (m, 2H), 2.94-3.18 (m, 2H), 2.28-2.48 (m, 3H), 1.28-2.13 (m, 10H), 1.39 (s, 9H), 1.26 (t, 4.5 Hz, 3H), 0.92 (d, J=6.3 Hz, 3H, 0.90 (d, J=6.3 Hz, 3H) ESI-MS (M+H$^+$)=702.

EXAMPLE 12

Preparation of Compound 12

Compound 12 was prepared in a manner similar to that described in Example 1.
ESI-MS (M+H$^+$)=680.

EXAMPLE 13

Preparation of Compound 13

Compound 13 was prepared in a manner similar to that described in Example 1.
$^1$H NMR (CDCl$_3$) δ 7.94 (d, J=7.0 Hz, 1H), 7.31 (s, 5H), 6.81 (dd, J=15, 5 Hz, 1H), 6.38 (br s, 1H), 5.84-5.93 (m, 2H), 5.31 (br s, 1H), 5.07 (s, 2H), 4.41-4.64 (m, 2H), 4.11-4.16 (m, 4H), 3.62-3.64 (m, 2H), 3.60 (s, 3H), 3.43-3.51 (m, 2H), 3.23-3.29 (m, 2H), 3.06-3.20 (m, 2H), 2.28-2.48 (m, 2H), 1.20-1.96 (m, 8H), 1.26 (t, J=4.5 Hz, 3H), 0.92 (d, J=6.5 Hz, 3H), 0.90 (d, J=6.5 Hz, 3H). ESI-MS (M+H$^+$)=660.

EXAMPLE 14

Preparation of Compound 14

Compound 14 was prepared in a manner similar to that described in Example 1.
$^1$H NMR (CDCl$_3$) δ 0.93 (m, 6H), 1.25-1.30 (m, 3H), 1.47-1.98 (m, 5H), 2.20-2.60 (m, 5H), 2.93 (3, 3H), 3.11-3.45 (m, 4H), 4.12-4.19 (m, 2H), 4.45-4.48 (m, 3H), 5.09 (s, 2H), 5.86-5.92 (d, 1H, J=15.9 Hz), 6.75-6.82 (dd, 1H, J=15.9 Hz, 5.1 Hz), 7.33-7.36 (m, 5H), 8.12 (br, s, 1H), 8.23 (br, s, 1H). ESI-MS (M+H$^+$)=637.

EXAMPLE 15

Preparation of Compound 15

Compound 15 was prepared in a manner similar to that described in Example 1.
ESI-MS (M+H$^+$)=631.

EXAMPLE 16

Preparation of Compound 16

Compound 16 was prepared in a manner similar to that described in Example 1.
$^1$H NMR (CDCl$_3$) δ 0.81-0.86 (m, 6H), 1.11-1.22 (m, 5H), 1.29-1.34 (m, 2H), 1.55-1.77 (m, 9H), 2.37 (s, br, 3H), 2.93 (s, 2H), 3.25 (s, br, 2H), 3.62-3.64 (m, 1H), 4.10 (q, 2H, J=6.6), 4.28-4.48 (m, 3H), 4.93-5.07 (m, 2H), 5.83 (d, 1H, J=15), 5.99 (s, 1H), 6.75 (dd, 1H, J=16.5, 6.3), 7.26 (s, br, 5H), 7.82 (m, 1H), 8.19 (s, 1H).

EXAMPLE 17

Preparation of Compound 17

Compound 17 was prepared in a manner similar to that described in Example 1.
$^1$H NMR (CD$_3$OD) δ 0.92-1.00 (m, 6H), 1.18-1.33 (m, 15H), 1.58-1.82 (m, 6H), 2.02-2.35 (m, 4H), 3.20-3.32 (m, 2H), 4.14-4.32 (m, 4H), 4.62-4.66 (m, 1H), 5.07-5.13 (m, 2H), 5.29 (d, 1H, J=5.4), 5.92 (d, 1H, J=15.6), 6.88 (dd, 1H, J=15.6, 5.7), 7.29-7.36 (m, 5H). ESI-MS (M+H$^+$)=632.

EXAMPLE 18

Preparation of Compound 18

Compound 18 was prepared in a manner similar to that described in Example 1.
$^1$H NMR (CDCl$_3$) δ 0.90-0.92 (m, 12H), 3.65 (t, 3H, J=6.9), 1.50-1.61 (m, 4H), 1.77 (m, 1H), 2.01-2.07 (m, 3H), 2.37 (m, 2H), 3.27-3.36 (m, 2H), 3.65 (t, 2H, J=5.4), 3.96(t, 1H, J=6.9), 4.15(q, 2H, J=6.9), 4.30(t, 2H, J=5.4), 4.60(m, 2H), 5.60(d, 1H, J=8.4), 5.89(d, 1H, J=15.6), 6.64(s, 1H), 6.80(dd, 1H, J=15.6), 7.07(d, 1H, J=7.8), 7.76(d, 1H, J=7.5). ESI-MS (M+H$^+$)=545.

EXAMPLE 19

Preparation of Compound 19

Compound 19 was prepared in a manner similar to that described in Example 1.
$^1$H NMR (CDCl$_3$) δ 0.84-0.89 (m, 12H), 1.15-1.22 (m, 6H), 1.45-1.57 (m, 3H), 1.75 (s, br, 3H), 1.94-2.09 (m, 2H), 2.32 (s, br, 2H), 3.27 (d, 2H, J=7.8), 3.87 (t, 1H, J=6.9), 4.00-4.13 (m, 4H), 4.53 (s, br, 2H), 5.20 (d, 1H, J=8.4), 5.83 (d, 1H, J=15.3), 6.42 (s, 1H), 6.75 (dd, 1H, J=15.6, 5.4), 6.92 (d, 1H, J=8.1), 7.67 (d, 1H, J=7.2). ESI-MS (M+H$^+$)=533.

EXAMPLE 20

Preparation of Compound 20

Compound 20 was prepared in a manner similar to that described in Example 1.
$^1$H NMR (CDCl$_3$) δ 0.90-0.93 (m, 18H), 1.24-1.29 (t, 3H, J=5.4Hz), 1.52-2.20 (m, 4H), 2.40 (br, s, 2H), 3.32-3.35 (d, 2H), 3.82-3.84 (m, 2H), 3.91-3.96 (t, 1H, J=7.8 Hz), 4.13-4.20 (q, 2H, J=7.5Hz), 4.58 (br s, 2H), 5.25-5.27 (d, 1H, J=8.1Hz), 5.89 (d, 1H, J=15.3 Hz), 6.32 (br, s, 1H), 6.81 (dd, 1H, J=15.6 Hz, 5.1 Hz), 6.92 (m, 1H), 7.77 (m, 1H). ESI-MS (M+H$^+$)=539.

EXAMPLE 21

Preparation of Compound 21

Compound 21 was prepared in a manner similar to that described in Example 1.
$^1$H NMR (CDCl$_3$) δ 0.92-0.96 (m, 12H), 1.27 (t, 3H, J=7.2), 1.43 (s, 9H), 2.04-2.11 (m, 2H), 2.38 (s, br, 2H), 3.23-3.35 (m, 2H), 3.83 (t, 1H, J=7.2), 4.16 (q, 2H, J=7.2), 4.61 (m, 2H), 5.00-5.03 (m, 1H,), 5.89 (d, 1H, J=15.3), 6.48 (s, br, 1H), 6.81 (dd, 1H, J=15.6, 5.1), 7.00 (m, 1H), 7.68 (m, 1H). ESI-MS (M+H$^+$)=539.

EXAMPLE 22

Preparation of Compound 22

Compound 22 was prepared in a manner similar to that described in Example 1.
$^1$H NMR (CDCl$_3$) δ 0.91 (s, br, 12H), 1.21-1.25 (m, 4H), 1.34-1.36 (m, 1H), 1.51-1.75 (m, 1H), 2.00-2.13 (m, 2H), 2.34 (m, 2H), 3.26-3.29 (m, 2H), 3.64 (s, br, 2H), 3.94-3.96 (m, 1H), 4.15 (q, 2H, J=6.9), 4.22 (m, 2H), 4.54 (s, 2H), 4.59 (s, br, 1H), 5.45 (d, 1H, J=7.5), 5.89 (d, 1H, J=15.6), 6.61 (s, br, 1H), 6.80 (dd, 1H, J=15.9, 4.5), 7.01 (d, 1H, J=7.2), 7.30 (m, 5H), 7.74 (d, 1H, J=7.2). ESI-MS (M+H$^+$)=616.

EXAMPLE 23

Preparation of Compound 23

Compound 23 was prepared in a manner similar to that described in Example 1.
ESI-MS (M+H$^+$)=545.

EXAMPLE 24

Preparation of Compound 24

Compound 24 was prepared in a manner similar to that described in Example 1.
ESI-MS (M+H$^+$)=558.

EXAMPLE 25

Preparation of Compound 25

Compound 25 was prepared in a manner similar to that described in Example 1.
$^1$H NMR (CD$_3$OD) δ 0.95-1.00 (m, 12 H), 1.26-1.29 (m, 6H), 1.57-1.85 (m, 5H), 2.03-2.14 (m, 3H), 2.27-2.32 (m, 1H), 2.45-2.52 (m, 1H), 3.93 (s, br, 2H), 4.03-4.04 (m, 1H), 4.16-4.20 (m, 5H), 4.37-4.41 (m, 1H), 4.59-4.63 (m, 1H), 5.94 (d, 1H, J=15.6), 6.89 (dd, 1H, J=15.6, 4.5). ESI-MS (M+H$^+$)=568.

EXAMPLE 26

Preparation of Compound 26

Compound 26 was prepared in a manner similar to that described in Example 1.
$^1$H NMR (CDCl$_3$) δ 0.86-0.96 (m, 12H), 1.27 (t, 3H, J=6.9), 1.49-1.82 (m, 10H), 1.95-2.02 (m, 1H), 2.40 (s, br, 2H), 3.32-3.34 (m, 2H), 4.16 (q, 2H, J=6.9), 4.55-4.67 (m, 3H), 5.89 (d, 1H, J=15.3), 6.39 (s, br, 1H), 6.72 (d, 1H, J=5.4), 6.81 (dd, 2H, J=15.9, 5.1), 7.31-7.76 (m, 5H). ESI-MS (M+H$^+$)=557.

EXAMPLE 27

Preparation of Compound 27

Compound 27 was prepared in a manner similar to that described in Example 1.
ESI-MS (M+H$^+$)=690.

EXAMPLE 28

Preparation of Compound 28

Compound 28 was prepared in a manner similar to that described in Example 1.
$^1$H NMR (CDCl$_3$) δ 0.89-0.94 (m, 6H), 1.22-1.28 (m, 5H), 1.57-2.03 (m, 8H), 2.43 (m, 2H), 3.33 (d, 2H, J=6.6), 3.65 (s, 3H), 3.67 (s, 3H), 4.15 (q, 2H, J=6.9), 4.26 (m, 1H), 4.44 (m, 1H), 4.60 (m, 1H), 5.28 (s, 1H), 5.91 (d, 1H, J=15.6), 6.24-6.29 (m, 1H), 6.82 (dd, 1H, J=15.9, 5.4), 7.89 (m, 1H). ESI-MS (M+H$^+$)=542.

EXAMPLE 29

Preparation of Compound 29

Compound 29 was prepared in a manner similar to that described in Example 1.
$^1$H NMR (CDCl$_3$) δ 7.78 (d, J=7.5 Hz, 1H), 7.28 (s, 5H), 7.01 (d, J=7.5 Hz, 1H), 6.79 (dd, J=15.5, 5.5 Hz, 1H), 6.50 (s, 1H), 5.89 (d, J=15.5 Hz, 1H), 5.38 (d, J=7.0 Hz, 1H), 4.46-4.61 (m, 4H), 4.06-4.21 (m, 4H), 3.29 (d, J=9.0 Hz, 2H), 2.35 (br, s, 2H), 2.03 (s, 3H), 1.47-1.72 (m, 3H), 1.44 (s, 9H), 1.17-1.28 (m, 6H), 0.88 (d, J=8.4 Hz, 3H), 0.86 (d, J=8.4 Hz 3H). ESI-MS (M+H$^+$)=631.

EXAMPLE 30

Preparation of Compound 30

Compound 30 was prepared in a manner similar to that described in Example 1.
ESI-MS (M+H$^+$)=663.

EXAMPLE 31

Preparation of Compound 31

Compound 31 was prepared in a manner similar to that described in Example 1.
$^1$H NMR (CDCl$_3$) δ 0.84-0.94 (m, 6H), 1.07 (m, 3H), 1.25 (m, 3H), 1.27 (s, 9H), 1.44 (s, 9H), 1.66-1.73 (m, 5H), 2.37 (br, s, 1H), 3.33 (d, 2H, J=8.1), 4.08-4.19 (m, 5H), 4.42-4.58 (m, 2H), 5.53-5.16 (d, 1H, J=4.8 Hz), 5.87-5.92 (d, 1H, J=15.6 Hz), 6.77-6.84 (dd, 1H, J=15.3 Hz, 5.1 Hz), 7.34-7.37 (d, 1H, J=8.1 Hz), 7.650-7.60 (m, 1H). ESI-MS (M+H$^+$)= 597.

EXAMPLE 32

Preparation of Compound 32

Compound 32 was prepared in a manner similar to that described in Example 1.
ESI-MS (M+H$^+$)=561.

EXAMPLE 33

Preparation of Compound 33

Compound 33 was prepared in a manner similar to that described in Example 1.
$^1$H NMR (CDCl$_3$) δ 0.83-0.88 (m, 6H), 1.10-1.20 (m, 9H), 1.30-1.35 (t, 2H, J=7.5), 1.57-1.96 (m, 5H), 2.38 (s, br, 2H), 3.02-3.09 (q, 1H, J=7.8), 3.27-3.39 (m, 4H), 4.10 (q, 2H, J=6.9), 4.34 (s, br, 2H), 4.50 (m, 1H), 4.60 (m, 1H), 4.95 (s, br, 1H), 5.80-5.85 (d, 1H, J=15.6), 6.25 (s, br, 1H), 6.73 (dd, 1H, J=4.5), 7.31 (s, br, 1H), 7.69 (s, br, 1H). ESI-MS (M+H$^+$)= 527.

EXAMPLE 34

Preparation of Compound 34

Compound 34 was prepared in a manner similar to that described in Example 1.
$^1$H NMR (CDCl$_3$) δ 0.93 (s, br, 6H), 1.28 (t, 3H, J=6.9), 1.60-2.00 (m, 9H), 2.29 (m, 1H), 2.49 (m, 1H), 3.21-3.34 (m, 4H), 3.65-3.69 (m, 6H), 4.17 (q, 2H, J=6.6), 4.30 (m, 1H), 4.50 (m, 1H), 4.78 (m, 1H), 5.14 (m, 1H), 5.87 (d, 1H, J=15), 6.49-6.56 (m, 1H), 6.80-6.86 (m, 2H). ESI-MS (M+H$^+$)=570.

EXAMPLE 35

Preparation of Compound 35

Compound 35 was prepared in a manner similar to that described in Example 1.

¹H NMR (CDCl₃) δ 0.94 (dd, 6H, J=12, 4.8), 1.29 (t, 3H, J=6.9), 1.67-2.04 (m, 9H), 2.30-2.50 (m, 2H), 2.94 (s, 3H), 2.96 (s, 3H), 3.18 (s, br, 2H), 3.35 (s, br, 2H), 4.05 (m, 1H), 4.18 (q, 2H, J=6.9), 4.49-4.52 (m, 1H), 4.61-4.77 (m, 1H), 5.30 (s, 1H), 5.90 (d, 1H, J=15.6), 6.25-6.34 (m, 1H), 6.82 (m, 1H), 7.38 (m, 1H), 7.77 (d, 1H, J=7.5). ESI-MS (M+H⁺)=610.

EXAMPLE 36

Preparation of Compound 36

Compound 36 was prepared in a manner similar to that described in Example 1.

¹H NMR (CDCl₃) δ 0.838 (m, 12H), 1.18 (t, 3H, J=6.3), 1.44-1.68 (m, 5H), 2.04-2.10 (m, 3H), 2.28 (m, 2H), 3.20-3.23 (m, 2H), 3.90-3.95 (m, 1H), 4.07-4.10 (m, 2H), 4.54 (s, br, 1H), 5.01 (s, 2H), 5.52-5.55 (m, 1H), 5.84 (d, 1H, J=15.6), 6.63 (s, 1H), 6.75 (dd, 1H, J=15.6, J=4.8), 7.73 (d, 1H, J=6.9). ESI-MS (M+H⁺)=573.

EXAMPLE 37

Preparation of Compound 37

Compound 37 was prepared in a manner similar to that described in Example 1.

¹H NMR (CDCl₃) δ 0.89 (m, 6H), 1.23 (t, 3H, J=10.2), 1.45-1.99 (m, 6H), 2.36-2.58 (m, 2H), 2.94-3.09 (m, 2H), 3.26-3.34 (m, 2H), 4.10-4.20 (m, 3H), 4.44-4.54 (m, 2H), 5.04 (s, 2H), 5.89 (d, 1H, J=15.3), 6.79 (dd, 1H, J=15.3, 4.8), 7.16-7.30 (m, 10H). ESI-MS (M+H⁺)=621.

EXAMPLE 38

Preparation of Compound 38

Compound 38 was prepared in a manner similar to that described in Example 1.

¹H NMR (CD₃OD) δ 0.79-0.91 (m, 6 H), 1.20-1.28 (m, 3H), 1.45-1.83 (m, 6H), 2.32-2.53 (m, 2H), 2.92-3.24 (m, 4H), 4.10-4.20 (m, 2H), 4.41-4.58 (m, 3H), 5.13 (s, 2H), 5.91 (dd, 1H, J=15.6, 1.5), 6.77-6.91 (m, 3H), 7.18-7.32 (m, 7H). ESI-MS (M+H⁺)=637.

EXAMPLE 39

Preparation of Compound 39

Compound 39 was prepared in a manner similar to that described in Example 1.

¹H NMR (CD₃OD) δ 0.79-0.91 (m, 6 H), 1.20-1.28 (m, 3H), 1.45-1.83 (m, 6H), 2.36-2.57 (m, 2H), 2.92-3.24 (m, 4H), 4.10-4.20 (m, 2H), 4.41-4.58 (m, 3H), 5.13 (s, 2H), 5.91 (dd, 1H, J=15.6, 1.5), 6.82-6.91 (m, 3H), 7.21-7.35 (m, 7H). ESI-MS (M+H⁺)=639.

EXAMPLE 40

Preparation of Compound 40

Compound 40 was prepared in a manner similar to that described in Example 1.

¹H NMR (CD₃OD) δ 0.79-0.90 (m, 6 H), 1.20-1.29 (m, 3H), 1.45-1.83 (m, 6H), 2.36-2.57 (m, 2H), 2.94-3.10 (m, 2H), 3.26-3.34 (m, 2H), 4.10-4.20 (m, 2H), 4.44-4.61 (m, 3H), 5.10 (s, 2H), 5.90 (dd, 1H, J=15.6, 1.5), 6.83-6.94 (m, 4H), 7.24-7.32 (m, 5H). ESI-MS (M+H⁺)=657.

EXAMPLE 41

Preparation of Compound 41

Compound 41 was prepared in a manner similar to that described in Example 1.

¹H NMR (CDCl₃) δ 0.79 (s, br, 6H), 1.12-1.22 (m, 7H), 1.38-1.96 (m, 3H), 2.32 (s, br, 1H), 2.90-3.05 (m, 2H), 3.21 (m, 2H), 4.10 (q, 2H, J=6.9), 4.37-4.58 (m, 3H), 4.95-5.02 (m, 3H), 5.85 (d, 1H, J=15.9), 6.17-6.18 (m, 2H), 6.70-6.77 (m, 2H), 7.03 (m, 1H), 7.25 (s, br, 5H), 7.54 (s, 1H), 8.16 (d, 1H, J=7.2). ESI-MS (M+H⁺)=610.

EXAMPLE 42

Preparation of Compound 42

Compound 42 was prepared in a manner similar to that described in Example 1.
ESI-MS (M+H⁺)=711.

EXAMPLE 43

Preparation of Compound 43

Compound 43 was prepared in a manner similar to that described in Example 1.

¹H NMR (CDCl₃) δ 0.69-0.83 (m, 6H), 1.21 (t, 3H, J=6.9), 1.29 (d, 1H, J=5.1), 1.44 (m, 1H), 1.86-2.23 (m, 6H), 2.97-2.99 (m, 2H), 3.13-3.21 (m, 2H), 3.88 (s, 1H), 4.09 (q, 2H, J=6.9), 4.43 (m, 1H), 4.71-4.77 (m, 1H), 5.02 (s, 2H), 5.36-5.40 (m, 1H), 5.65 (d, 1H, J=15.9), 6.61 (dd, 1H, J=15.3, J=4.5), 7.08-7.26 (m, 10H), 7.46-7.49 (m, 1H). ESI-MS (M+H⁺)=607.

EXAMPLE 44

Preparation of Compound 44

Compound 44 was prepared in a manner similar to that described in Example 1.
ESI-MS (M+H⁺)=579.

EXAMPLE 45

Preparation of Compound 45

Compound 45 was prepared in a manner similar to that described in Example 1.

¹H NMR (CDCl₃) δ 7.83 (d, J=8 Hz, 1H), 7.28-7.36 (m, 5H), 6.81 (dd, J=16, 6 Hz, 1H), 6.47 (s, 1H), 5.91 (d, J=15 Hz, 1H), 5.53 (d, J=8 Hz, 1H), 5.07-5.13 (m, 2H), 4.60-4.68 (m, 2H), 4.13 (q, J=7 Hz, 2H), 3.97 (dd, J=8, 3.6 Hz, 1H), 3.28-3.31 (m, 2H), 2.49 (t, J=7 Hz, 2H), 2.29-2.42 (m, 2H), 1.90-2.21 (m, 6H), 2.06 (s, 3H), 1.76 (m, 1H), 1.60 (m, 1H), 1.26 (t, J=7 Hz, 3H), 0.94 (d, J=6.9Hz, 3H) 0.91 (d, J=6.9 Hz, 3H). ESI-MS (M+H⁺)=591.

EXAMPLE 46

Preparation of Compound 46

Compound 46 was prepared in a manner similar to that described in Example 1.

¹H NMR (CDCl₃) δ 7.75 (d, J=7.5 Hz, 1H), 7.50 (d, J=8.4 Hz, 1H), 7.24-7.52 (m, 5H), 6.82 (dd, J=15, 5 Hz, 1H), 6.54 (s, 1H), 5.89 (dd, J=15, 1.8 Hz, 1H), 5.42 (d, J=7 Hz, 1H), 5.02-5.12 (m, 2H), 4.60-4.67 (m, 2H), 4.13 (q, J=7.2 Hz, 2H), 3.28-3.30 (m, 2H), 2.49 (t, J=7.5 Hz, 2H), 2.33-2.43 (m, 2H), 1.90-2.14 (m, 6H), 2.06 (s, 3H), 1.46-1.79 (m, 3H), 1.26 (t, J=7.2 Hz, 3H) 0.92 (d, J=1.5 Hz, 6H). ESI-MS (M+H⁺)=605.

EXAMPLE 47

Preparation of Compound 47

Compound 47 was prepared in a manner similar to that described in Example 1.
ESI-MS (M+H⁺)=639.

EXAMPLE 48

Preparation of Compound 48

Compound 48 was prepared in a manner similar to that described in Example 1.
ESI-MS (M+H⁺)=546.

EXAMPLE 49

Preparation of Compound 49

Compound 49 was prepared in a manner similar to that described in Example 1.
¹H NMR (CDCl₃) δ 1.26 (t, 3H, J=6.9), 1.55-1.63 (m, 1H), 1.75-1.82 (m, 1H), 1.94-2.02 (m, 1H), 2.22-2.31 (m, 1H), 2.41-2.51 (m, 1H), 3.59-3.60 (m, 1H), 3.68-3.73 (m, 1H), 3.82-3.87 (m, 2H), 4.15 (q, 2H, J=6.9), 4.27-4.29 (m, 1H), 4.44-4.50 (m, 1H), 4.63 (s, br, 1H), 5.10 (s, 2H), 5.95 (d, 1H, J=15.6), 6.85 (dd, 1H, J=15.6, 4.5), 7.2-7.34 (m, 4H), 8.16 (d, 1H, J=8.7). ESI-MS (M+H⁺)=571.

EXAMPLE 50

Preparation of Compound 50

Compound 50 was prepared in a manner similar to that described in Example 1.
ESI-MS (M+H⁺)=594.

EXAMPLE 51

Preparation of Compound 51

Compound 51 was prepared in a manner similar to that described in Example 1.
¹H NMR (CDCl₃) δ 0.88 (s, br, 6H), 1.18-1.77 (m, 12H), 2.38 (m, 1H), 2.93 (s, 3H), 2.97 (s, 3H), 3.29 (m, 2H), 4.10 (q, 2H, J=6.9), 4.49 (m, 2H), 5.15-5.21 (m, 1H), 5.37 (q, 1H, J=5.7), 5.80-5.85 (m, 2H), 6.07 (s, br, 1H), 6.73 (dd, 1H, J=15, 5.4), 7.29 (d, 1H, J=8.7), 7,82 (m, 1H), 8.70 (m, 1H). ESI-MS (M+H⁺)=596.

EXAMPLE 52

Preparation of Compound 52

Compound 52 was prepared in a manner similar to that described in Example 1.
¹H NMR (CDCl₃) δ 0.83-0.87 (m, 6H), 1.14 (s, 6H), 1.16-1.20 (m, 6H), 1.42-1.67 (m, 6H), 2.22-2.26 (m, 2H), 3.32-4.10 (m, 4H), 4.47 (br, s, 2H), 5.80-5.85 (d, 1H, J=15.3 Hz), 6.70-6.77 (dd, 1H, J=15.3 Hz, 5.1 Hz), 7.79-7.87 (br, s, 2H). ESI-MS (M+H⁺)=497.

EXAMPLE 53

Preparation of Compound 53

Compound 53 was prepared in a manner similar to that described in Example 1.
¹H NMR (CDCl₃) δ 0.96 (s, br, 6H), 1.16-1.30 (m, 15H), 1.62-2.02 (m, 6H), 2.33-2.46 (m, 2H), 2.98 (d, 3H, J=8.7), 3.34 (s, br, 2H), 3.88-3.91 (m, 1H), 4.14-4.19 (m, 3H), 4.40 (m, 1H), 4.60-4.76 (m, 1H), 5.76-6.14 (m, 3H), 6.81 (d, 1H, J=15), 7.60 (m, 1H). ESI-MS (M+H⁺)=575.

EXAMPLE 54

Preparation of Compound 54

Compound 54 was prepared in a manner similar to that described in Example 1.
¹H NMR (CDCl₃) δ 0.97 (t, 6H, J=0.8), 1.08 (d, 3H, J=5.7), 1.28 (s, b, 12H), 1.55-1.86 (m, 6H), 2.05 (m, 1H), 2.42 (m, 2H), 3.31 (d, 2H, J=8.1), 4.14-4.25 (m, 5H), 4.37-4.45 (m, 3H), 4.60 (m, 1H), 5.91-6.10 (m, 3H), 6.83 (dd, 1H, J=15.6, 4.5), 7.26-7.76 (m, 9H). ESI-MS (M+H⁺)=719.

EXAMPLE 55

Preparation of Compound 55

Compound 55 was prepared in a manner similar to that described in Example 1.
¹H NMR (CDCl₃) δ 0.96-0.99 (m, 6H), 1.14 (d, 3H, J=6.6), 1.24 (s, 9H), 1.28 (t, 3H, J=6.9), 1.39 (t, 3H, J=6.9), 1.58-2.04 (m, 5H), 2.35-2.40 (m, 2H), 3.05 (q, 2H, J=7.5), 3.31-3.34 (m, 2H), 3.87-3.89 (m, 1H), 4.09-4.10 (m, 1H), 4.17 (q, 2H, J=7.2), 4.41 (m, 1H), 4.59 (m, 1H), 4.74 (m, 1H), 5.73 (d, 1H, J=6.0), 5.84-5.96 (m, 1H), 6.22 (s, 1H), 6.41 (q, 1H, J=15.9, 4.8), 7.57-7.60 (m, 1H), 7.69 (d, 1H, J=7.2). ESI-MS (M+H⁺)=589.

EXAMPLE 56

Preparation of Compound 56

Compound 56 was prepared in a manner similar to that described in Example 1.
ESI-MS (M+H⁺)=603.

EXAMPLE 57

Preparation of Compound 57

Compound 57 was prepared in a manner similar to that described in Example 1.
¹H NMR (CDCl₃) δ 0.85-0.90 (m, 6H), 1.27 (t, 3H, J=7.2 Hz), 1.60-1.66 (m, 5H), 2.33 (m, 1H), 2.79 (m, 1H), 2.94 (m, 1H), 3.20 (m, 2H), 4.17 (q, 2H, J=6.9 Hz), 4.39 (m, 1H), 4.55 (m, 2H), 5.10 (s, 2H), 5.91 (d, 1H, J=15.9 Hz), 6.40 (m, 1H), 6.85 (dd, 1H, J=15.9, 5.1 Hz), 7.31 (m, 20H), 7.84 (m, 1H). ESI-MS (M+H⁺)=637.

EXAMPLE 58

Preparation of Compound 58

Compound 58 was prepared in a manner similar to that described in Example 1.
¹H NMR (CDCl₃) δ 0.88-0.94 (m, 6H), 1.27 (t, 3H, J=7.2 Hz), 1.60-1.66 (m, 5H), 2.07 (m, 1H), 2.43 (m, 2H), 2.72-2.80 (m, 2H), 3.30 (m, 2H), 4.17 (q, 2H, J=6.9 Hz), 4.39 (m, 1H), 4.55 (m, 2H), 5.10 (s, 2H), 5.91 (d, 1H, J=15.9 Hz), 6.10-6.20 (m, 2H), 6.30 (m, 2H), 6.85 (dd, 1H, J=15.9, 5.1 Hz), 7.31 (m, 5H), 7.60 (m, 1H). ESI-MS (M+H⁺)=588.

EXAMPLE 59

Preparation of Compound 59

Compound 59 was prepared in a manner similar to that described in Example 1.
$^1$H NMR (CD$_3$OD) δ 0.86-1.04 (m, 6H), 1.21-1.52 (m, 12H), 1.61-1.71 (m, 6H), 2.06-2.86 (m, 6H), 3.40 (m, 2H), 4.10-4.27 (m, 2H), 4.34-4.45 (m, 1H), 4.60-4.72 (m, 1H), 5.13 (s, 2H), 5.90 (d, 1H, J=15.6), 6.81 (dd, 1H, J=15.6, 4.8), 7.27-7.54 (m, 5H). ESI-MS (M+H$^+$)=645.

EXAMPLE 60

Preparation of Compound 60

Compound 60 was prepared in a manner similar to that described in Example 1.
$^1$H NMR (CD$_3$OD) δ 0.92-1.00 (m, 6H), 1.19-1.23 (m, 6H), 1.57-1.80 (m, 6H), 2.03-2.36 (m, 4H), 3.19-3.31 (m, 2H), 4.16-4.34 (m, 4H), 4.58-4.62 (m, 1H), 5.04-5.11 (m, 2H), 5.24 (d, 1H, J=5.1), 5.91 (d, 1H, J=15.3), 6.89 (dd, 1H, J=15.3, 5.4), 7.30-7.35 (m, 5H). ESI-MS (M+H$^+$)=576.

EXAMPLE 61

Preparation of Compound 61

Compound 61 was prepared in a manner similar to that described in Example 1.
ESI-MS (M+H$^+$)=576.

EXAMPLE 62

Preparation of Compound 62

Compound 62 was prepared in a manner similar to that described in Example 1.
ESI-MS (M+H$^+$)=617.

EXAMPLE 63

Preparation of Compound 63

Compound 63 was prepared in a manner similar to that described in Example 1.
ESI-MS (M+Na$^+$)=867.

EXAMPLE 64

Preparation of Compound 64

Compound 64 was prepared in a manner similar to that described in Example 1.
$^1$H NMR (CDCl$_3$) δ 0.94-0.99 (m, 6H), 1.07 (m, 3H), 1.28 (m, 15H), 1.60 (m, 3H), 2.10 (br, s, 2H), 2.29 (br, s, 2H), 3.32-3.35 (d, 2H), 4.09 (m, 6H), 4.32 (br, s, 1H), 4.60 (br, s, 1H), 5.76 (m, 1H), 5.84-5.89 (d, 1H, J=14.7Hz), 5.98 (br, s, 1H), 6.81 (dd, 1H, J=15.9 Hz, 5.4 Hz), 7.38 (m, 1H), 7.60 (m, 1H). ESI-MS (M+H$^+$)=569.

EXAMPLE 65

Preparation of Compound 65

Compound 65 was prepared in a manner similar to that described in Example 1.
$^1$H NMR (CDCl$_3$) δ 0.94-0.99 (m, 6H), 1.28 (t, 3H, J=6.9), 1.75-1.82 (m, 2H), 2.10-2.33 (m, 3H), 3.03-3.15 (m, 2H), 3.22-3.31 (m, 2H), 4.16 (q, 2H, J=7.5), 4.39-4.51 (m, 2H), 4.80-4.83 (m, 1H), 5.77 (d, 1H, J=15.6), 5.96 (s, 1H), 6.66-6.74 (m, 2H), 7.15-7.62 (m, 10H), 7.7 (d, 2H, J=8.1). ESI-MS (M+H$^+$)=577.

EXAMPLE 66

Preparation of Compound 66

Compound 66 was prepared in a manner similar to that described in Example 1.
ESI-MS (M+H$^+$)=630.

EXAMPLE 67

Preparation of Compound 67

Compound 67 was prepared in a manner similar to that described in Example 1.
$^1$H NMR (CDCl$_3$) δ 0.91 (s, br, 6H), 1.26 (t, 3H, J=6.9), 1.42 (s, 18H), 1.56-1.63 (m, 5H), 1.80-1.82 (m, 2H), 2.04 (m, 1H), 2.35-2.41 (m, 3H), 3.12 (s, br, 2H), 3.32 (s, br, 2H), 4.16 (m, 3H), 4.54 (s, br, 2H), 5.89 (d, 1H, J=15.6), 6.81(m, 2H). ESI-MS (M+H$^+$)=654.

EXAMPLE 68

Preparation of Compound 68

Compound 68 was prepared in a manner similar to that described in Example 1.
ESI-MS (M+H$^+$)=809.

EXAMPLE 69

Preparation of Compound 69

Compound 69 was prepared in a manner similar to that described in Example 1.
ESI-MS (M+H$^+$)=557.

EXAMPLE 70

Preparation of Compound 70

Compound 70 was prepared in a manner similar to that described in Example 1.
ESI-MS (M+H$^+$)=547.

EXAMPLE 71

Preparation of Compound 71

Compound 71 was prepared in a manner similar to that described in Example 1.
ESI-MS (M+H$^+$)=562.

EXAMPLE 72

Preparation of Compound 72

Compound 72 was prepared in a manner similar to that described in Example 1.
ESI-MS (M+H$^+$)=605.

EXAMPLE 73

Preparation of Compound 73

Compound 73 was prepared in a manner similar to that described in Example 1.
ESI-MS (M+H$^+$)=600.

EXAMPLE 74

Preparation of Compound 74

Compound 74 was prepared in a manner similar to that described in Example 1.
$^1$H NMR (CDCl$_3$) δ 0.88-0.98 (m, 6 H), 1.19-1.86 (m, 15H), 2.0-2.08 (m, 1H), 2.15-2.39 (m, 2H), 2.47-2.59 (m, 1H), 2.94 (m, 2H), 3.98-4.20 (m, 3H), 4.30-4.36 (m, 1H), 4.60-4.64 (m, 1H), 5.09 (m, 2H), 5.89 (d, 1H, J=15.6), 6.89 (dd, 1H, 15.6, 4.8), 7.26-7.33 (m, 5H). ESI-MS (M+H$^+$)=602.

EXAMPLE 75

Preparation of Compound 75

Compound 75 was prepared in a manner similar to that described in Example 1.
$^1$H NMR(CDCl$_3$) δ 0.89-0.93(m, 6H), 1.13-1.15(m, 3H), 1.22-1.27(m, 3H), 1.55-1.76(m, 4H), 1.95-2.-2(m, 1H), 2.03-2.46(m, 2H), 3.28-3.30(m, 2H), 4.11-4.18(m, 3H), 4.33(br s, 1H), 4.54-4.56(br s, 2H), 5.07(s, 2H), 5.84-5.94(d, 1H, J=15.9 Hz), 6.03-6.06(d, J=7.2 Hz), 6.76-6.83(dd, 1H, J=15.0 Hz, 5.4 Hz), 7.31(br s, 5H), 8.02(br s, 1H). ESI-MS (M+H$^+$)=575.

EXAMPLE 76

Preparation of Compound 76

Compound 76 was prepared as follows: Compound 74 (0.047 g, 0.11 mmol) was dissolved in CH$_2$Cl$_2$ (1.5 ml). Et$_3$N (0.037 ml, 3.0 eq.) was then added to the above solution. The resultant solution was stirred at room temperature for 30 minutes. Methyl chloroformate (0.013 ml, 1.5 eq.) was subsequently added. The reaction mixture was stirred at room temperature for another 20 hours and then concentrated to afford a residue. The residue was purified by flash column chromatography (5% MeOH in CH$_2$Cl$_2$) to afford compound 76 as a white solid (64 mg, 85%).
$^1$H NMR (CDCl$_3$) δ 0.88-0.98 (m, 6 H), 1.19-1.83 (m, 15H), 2.0-2.08 (m, 1H), 2.15-2.38 (m, 2H), 2.47-2.59 (m, 1H), 3.07 (m, 2H), 3.59 (s, 3H), 3.98-4.20 (m, 3H), 4.310-4.36 (m, 1H), 4.60-4.64 (m, 1H), 5.08 (m, 2H), 5.88 (d, 1H, J=15.6), 6.89 (dd, 1H, 15.6, 4.8), 7.27-7.32 (m, 5H). ESI-MS (M+H$^+$)=660.

EXAMPLE 77

Preparation of Compound 77

Compound 77 was prepared in a manner similar to that described in Example 1.
ESI-MS (M+H$^+$)=523.

EXAMPLE 78

Preparation of Compound 78

Compound 78 was prepared in a manner similar to that described in Example 1.
ESI-MS (M+H$^+$)=557.

EXAMPLE 79

Preparation of Compound 79

Compound 79 was prepared in a manner similar to that described in Example 1.
ESI-MS (M+H$^+$)=423.

EXAMPLE 80

Preparation of Compound 80

Compound 80 was prepared as follows: Compound 59 (0.023 g, 0.036 mmol) was added to a solution of HCl in 1,4-dioxane (4.0 M, 2 ml). The solution was stirred at room temperature for 30 minutes and then concentrated to give compound 80 as a white solid (21 mg, 99%);
$^1$H NMR (CD$_3$OD) δ 0.86-1.04 (m, 6H), 1.23 (s, br, 3H), 1.60-1.71 (m, 6H), 2.06-2.85 (m, 6H), 3.38 (m, 2H), 4.10-4.28 (m, 2H), 4.34-4.45 (m, 1H), 4.60-4.72 (m, 1H), 5.13 (s, 2H), 5.91 (d, 1H, J=15.9), 6.82 (dd, 1H, J=15.9, 4.7), 7.27-7.54 (m, 5H). ESI-MS (M+H$^+$)=589.

EXAMPLE 81

Preparation of Compound 81

Compound 81 was prepared in 20% yield from compound 52 and methyl chloroformate.
$^1$H NMR(CDCl$_3$) δ 0.94-0.99 (m, 6H), 1.07 (m, 3H), 1.28 (m, 12H), 1.60 (m, 3H), 2.10 (br s, 2H), 2.29 (br s, 2H), 3.32-3.35 (d, 2H), 3.69 (s, 3H), 4.18 (m, 4H), 4.39 (br s, 1H), 4.61 (br s, 1H), 5.59-5.81 (m, 2H), 5.89-5.95 (d, 1H, J=16.2Hz), 6.82 (dd, 1H, J=15.3 Hz, 5.7 Hz), 7.34 (m, 1H), 7.56 (m, 1H). ESI-MS (M+H$^+$)=555.

EXAMPLE 82

Preparation of Compound 82

Compound 82 was prepared in a manner similar to that described in Example 1.
$^1$H NMR(CDCl$_3$) δ 0.95 (m, 6H), 1.02-1.04 (m, 3H), 1.27 (s, 12H), 1.56-1.82 (m, 5H), 2.03 (s, 3H), 2.18 (m, 1H), 2.40 (m, 2H), 3.31-3.34 (m, 2H), 4.15-4.18 (m, 3H), 4.36 (m, 1H), 4.46 (m, 1H), 4.61 (m, 1H), 5.92 (d, 1H, J=15 Hz), 6.38 (s, 1H), 6.63 (s, 1H), 6.82 (d, 1H, J=15 Hz), 7.53 (d, 1H, J=6 Hz), 7.65 (d, 1H, J=6 Hz). ESI-MS (M+H$^1$)=539.

EXAMPLE 83

Preparation of Compound 83

Compound 83 was prepared in a manner similar to that described in Example 1.
$^1$H NMR (CDCl$_3$) δ 0.96 (t, 6H, J=6 Hz), 1.08 (d, 3H, J=6 Hz), 1.26 (s, 9H), 1.54-2.42 (m, 8H), 3.35 (d, 2H, J=9 Hz), 3.68 (t, 2H, J=6 Hz), 4.14-4.27-4.38 (m, 2H), 4.45 (br, 1H), 4.60 (br, 1H), 5.92 (d, 2H, J=15 Hz), 6.32 (s, 1H), 6.83 (dd, 1H, J=15.0 Hz, 6.0 Hz), 7.39 (d, 1H, J=6 Hz), 7.66 (d, 1H, J=6 Hz). ESI-MS (M+Na$^+$)=625.

EXAMPLE 84

Preparation of Compound 84

Compound 84 was prepared in a manner similar to that described in Example 1.
$^1$H NMR (CDCl$_3$) δ 0.97 (q, 6H, J=6 Hz), 1.13 (d, 3H, J=6 Hz), 1.26 (s, 12H), 1.55-2.06 (m, 6H), 2.41 (br, 2H), 3.32 (d, 2H, J=9 Hz), 4.04-4.09 (m, 2H, J=6 Hz), 4.41 (br, 1H), 4.59 (br, 1H), 5.93 (d, 1H, J=15 Hz), 6.32 (s, 1H), 6.83 (dd, 1H, J=15.0 Hz, 6.0 Hz), 7.02 (d, 1H, J=6 Hz), 7.58 (d, 1H, J=6 Hz), 7.79 (d, 1H, J=6 Hz). ESI-MS (M+H$^+$)=629.

EXAMPLE 85

Preparation of Compound 85

Compound 85 was prepared in a manner similar to that described in Example 1 in a 68% yield.
$^1$H NMR (CDCl$_3$) δ 7.83 (d, J=8 Hz, 1H), 7.28-7.36 (m, 5H), 6.81 (dd, J=16, 6 Hz, 1H), 6.47 (s, 1H), 5.91 (d, J=15 Hz, 1H), 5.53 (d, J=8 Hz, 1H), 5.07-5.13 (m, 2H), 4.60-4.68 (m, 2H), 4.13 (m, 3H), 3.97 (dd, J=8, 3.6 Hz, 1H), 3.28-3.31 (m, 2H), 2.49 (t, J=7 Hz, 2H), 2.29-2.42 (m, 2H), 1.90-2.21 (m, 6H), 2.06 (s, 3H), 1.76 (m, 1H), 1.26 (m, 12H), 0.95 (d, J=6.9 Hz, 3H). ESI-MS (M+H$^+$)=649.

EXAMPLE 86

Preparation of Compound 86

Compound 86 was prepared in a manner similar to that described in Example 1 in a 57% yield.
$^1$H NMR (CDCl$_3$) δ 7.83 (d, J=8 Hz, 1H), 7.28-7.36 (m, 5H), 6.81 (dd, J=16, 6 Hz, 1H), 6.47 (s, 1H), 5.91 (d, J=15 Hz, 1H), 5.53 (d, J=8 Hz, 1H), 5.07-5.13 (m, 2H), 4.60-4.68 (m, 2H), 4.13 (q, J=7 Hz, 2H), 3.97 (dd, J=8, 3.6 Hz, 1H), 3.28-3.31 (m, 2H), 2.06-2.86 (m, 6H), 1.90-2.21 (m, 6H), 2.06 (s, 3H), 1.76 (m, 1H), 1.21-1.52 (m, 12H). ESI-MS (M+H$^+$)=663.

EXAMPLE 87

Preparation of Compound 87

Compound 87 was prepared in a manner similar to that described in Example 1.
$^1$H NMR (CDCl$_3$) δ 0.98 (d, 6H, J=6 Hz), 1.09 (s, 12H), 1.27 (t, 3H, J=6 Hz), 1.50-2.49 (m, 8H), 3.32 (q, 2H, J=3 Hz), 3.63 (q, 1H, J=3 Hz), 3.87-3.90 (m, 1H), 4.16 (q, 2H, J=6 Hz), 4.29-4.45 (m, 1H), 4.77 (m, 1H), 5.84 (br, 1H), 5.93 (d, 1H, J=15 Hz), 6.12 (d, 1H, J=6 Hz), 6.81 (dd, 1H, J=15.0 Hz, 6.0 Hz), 7.33-7.44 (m, 5H), 8.48 (d, 1H, J=9 Hz). ESI-MS(M+H$^+$)=651.

EXAMPLE 88

Preparation of Compound 88

Compound 88 was prepared in a manner similar to that described in Example 1.
$^1$H NMR (CDCl$_3$) δ 0.91-0.96 (m, 6H), 1.04-1.06 (m, 3H), 1.23 (m, 12H), 1.51-2.05 (m, 8H), 2.40 (br s, 2H), 3.30 (m, 2H), 4.15 (m, 4H), 4.39 (m, 1H), 4.54 (m, 2H), 5.19-5.32 (m, 2H), 5.84-5.97 (m, 3H), 6.82 (dd, 1H, J=15.6 Hz, 5.4 Hz), 7.35 (m, 1H), 7.60 (m, 1H). ESI-MS (M+H$^+$)=581.

EXAMPLE 89

Preparation of Compound 89

Compound 89 was prepared in a 85% yield by reacting compound 1 with pivaloyl chloride in the presence of Et$_3$N and DMAP.
$^1$H NMR (CDCl$_3$) δ 0.94-0.98 (m, 6H), 1.08 (d, J=6.3 Hz, 3H), 1.25 (s, 9H), 1.66-1.73 (m, 5H), 2.21-2.50 (m, 2H), 3.20-3.30 (m, 2H), 4.16 (q, J=6.9 Hz, 2H), 4.42 (br, 1H), 4.58 (br, 1H), 5.10 (s, 2H), 5.9 (d, J=15.6 Hz, 1H), 6.82 (dd, J=15.3 Hz, 5.1 Hz, 1H), 7.2-7.34 (m, 4H), 7.60 (d, J=7.5 Hz, 1H). ESI-MS (M+H$^+$)=659.

EXAMPLE 90

Preparation of Compound 90

Compound 6 was dissolved in an 1N NaOH/EtOH solution. The mixture was stirred for 1 hour and concentrated to afford a residue. The residue was purified by column chromatography to give compound 90 in a 20% yield.
$^1$H NMR (CDCl$_3$) δ 0.83-0.93 (m, 6H), 1.02-1.04 (d, 4H, J=5.7Hz), 1.16-1.31 (m, 11H), 1.52-1.74 (m, 5H), 2.0 (m, 1H), 2.30-2.43 (m, 2H), 3.24-3.26 (m, 2H), 4.15 (m, 2H), 4.41 (br s, 1H), 4.63 (br s 1H), 5.08 (s, 2H), 5.9 (m, 1H), 6.82 (m, 1H), 7.29-7.33 (m, 5H), 7.47 (d, 1H, J=8.1 Hz), 7.69 (m, 1H). ESI-MS (M+H$^+$)=603.

EXAMPLE 91

Preparation of Compound 91

Compound 91 was prepared in a manner similar to that described in Example 1.
$^1$H NMR (CDCl$_3$) δ 0.93 (q, 6H, J=3 Hz), 1.05 (d, 3H, J=6 Hz), 1.21-1.24 (m, 15H), 1.42-2.05 (m, 6H), 2.38 (br, 2H), 3.26-3.29 (m, 2H), 4.15 (br, 2H), 4.39 (m, 1H), 4.57 (m, 1H), 4.97-5.14 (m, 3H), 5.85-5.90 (m, 3H), 6.78 (dd, 1H, J=15.6 Hz, 5.4 Hz), 7.34 (m, 5H), 7.57 (d, 1H, J=7.2 Hz). ESI-MS (M+H$^+$)=645.

EXAMPLE 92

Preparation of Compound 92

Compound 92 was prepared in a manner similar to that described in Example 1.
$^1$H NMR (CDCl$_3$) δ 0.93-0.98 (m, 6H), 1.10 (d, 3H, J=6.3), 1.25 (s, 9H), 1.55-1.68 (m, 9H), 2.40 (m, 3H), 3.30-3.39 (m, 2H), 4.10-4.20 (m, 4H), 4.26-4.36 (m, 1H), 4.25-4.58 (m, 1H), 5.10 (q, 2H, J=12), 5.49 (d, 1H, J=16.5), 5.64 (s, 1H), 5.84 (d, 1H, J=5.4), 6.59 (dd, J=16.5, 5.0H), 7.29-7.34 (m, 5H), 7.96 (d, J=6.0). ESI-MS (M+H$^+$)=584.1.

EXAMPLE 93

Preparation of Compound 93

Compound 93 was prepared in a manner similar to that described in Example 1 in a 66% yield.
$^1$H NMR (CDCl$_3$) δ 0.86-095 (m, 6H), 1.22 (m, 4H), 1.41 (m, 11H), 1.55-1.90 (m, 9H), 2.32 (m, 2H), 3.25-3.35 (m, 3H), 3.39 (m, 1H), 4.11-4.19 (m, 2H), 4.34-4.47 (m, 2H), 4.85 (m, 1H), 5.08 (s, 2H), 5.84 (m, 2H), 6.09 (m, 1H), 6.73-6.75 (m, 1H), 7.73 (m, 1H). ESI-MS(M+H$^+$)=707.

EXAMPLE 94

Preparation of Compound 94

Compound 94 was prepared as follows: Compound 93 was added into a solution of HCl in 1,4-dioxane. The mixture was stirred at room temperature for 30 minutes and concentrated. CH$_2$Cl$_2$ was then added to the resultant residue and the mixture was cooled down to 0-5° C. N-methylmorpholine was added into the mixture, which was then stirred for 10 minutes. Benzochloromate was subsequently added to the solution, which was stirred at room temperature for another 2 hours to give a crude product. The crude product was purified by flash column chromatography to give compound 94.

¹H NMR (CDCl₃) δ 0.86-095 (m, 6H), 1.22 (m, 4H), 1.41 (m, 11H), 1.55-1.90 (m, 9H), 2.32 (m, 2H), 3.25-3.35 (m, 3H), 3.39 (m, 1H), 4.11-4.19 (m, 2H), 4.34-4.47 (m, 2H), 4.85 (m, 1H), 5.84 (m, 2H), 6.09 (m, 1H), 6.73-6.75 (m, 1H), 7.73 (m, 5H). ESI-MS (M+H⁺)=585.

EXAMPLE 95

Preparation of Compound 95

Compound 95 was prepared in a manner similar to that described in Example 1.
¹H NMR (CDCl₃) δ 0.93-0.98 (m, 6H), 1.07 (d, 3H, J=5.4), 1.27 (s, 9H), 1.52-2.10 (m, 8H), 2.40 (m, 2H), 3.23 (s, 3H), 3.28-3.31 (m, 2H), 3.68 (s, 3H), 4.16 (m, 2H), 4.44-4.45 (m, 1H), 4.63-4.64 (m, 1H), 5.10 (q, 2H, J=6), 5.90 (d, 1H, J=4.5), 6.51 (d, 1H, J=15.6), 6.83 (dd, 1H, J=5.1, 15.3), 7.35 (m, 5H), 7.57-7.62 (m, 1H). ESI-MS (M+H⁺)=646.

EXAMPLE 96

Preparation of Compound 96

Compound 96 was prepared in a manner similar to that described in Example 1 in a 38% yield.
¹H NMR (CDCl₃) δ 0.95 (q, 6H, J=8.4 Hz), 1.09 (d, 3H, J=6.3 Hz), 1.17 (d, 6H, J=6.6 Hz), 1.26 (s, 9H), 1.52-1.82 (m, 5H), 1.99-2.06 (m, 1H), 2.38 (br, 2H), 3.27-3.30 (m, 2H), 4.06-4.21 (m, 3H), 4.41 (m, 1H), 4.61 (m, 1H), 5.11 (q, 2H, J=3 Hz), 5.65 (d, 1H, J=7.8), 5.84-5.89 (m, 3H), 6.66 (dd, 1H, J=14.7 Hz, 5.4 Hz), 7.29-7.35 (m, 5H), 7.47 (d, 1H, J=7.8 Hz). ESI-MS(M+H⁺)=644.

EXAMPLE 97

Preparation of Compound 97

Compound 97 was prepared in a manner similar to that described in Example 1 in a 71% yield.
¹H NMR(CDCl₃) δ 0.25 (q, 2H, J=5.4 Hz), 0.50-0.56 (m, 2H), 0.93 (q, 6H, J=2.1 Hz), 1.03-1.18 (m, 4H), 1.24 (s, 9H), 1.50-2.07 (m, 7H), 2.36-2.41 (m, 2H), 3.25-3.28 (m, 2H), 3.92 (d, 2H, J=7.2 Hz), 4.14-4.16 (m, 2H), 4.40-4.45 (m, 1H), 4.58 (m, 1H), 5.08 (q, 2H, J=6.6 Hz), 5.87 (d, 1H, J=5.1 Hz), 5.93 (d, 1H, J=15.6 Hz), 6.08 (s, 1H), 6.82 (dd, 1H, J=15.9 Hz, 5.4 Hz), 7.29-7.38 (m, 5H), 7.63 (d, 1H, J=7.5 Hz). ESI-MS (M+Na⁺)=679.

EXAMPLE 98

Preparation of Compound 98

Compound 98 was prepared in a manner similar to that described in Example 1 in a 50% yield.
¹H NMR (CDCl₃) δ 0.85-098 (m, 6H), 1.06 (m, 4H), 1.26 (s, 9H), 1.44-1.63 (m, 9H), 1.75-1.80 (m, 7H), 2.05-2.34 (m, 2H), 3.27-3.29 (m, 2H), 3.70-3.72 (m, 1H), 4.14 (m, 2H), 4.42 (m, 1H), 4.59 (m, 1H), 5.08 (s, 2H), 5.88-5.98 (m, 4H), 6.09 (m, 1H), 6.80-6.87 (m, 1H), 7.25 (m, 10H), 7.65 (m, 1H). ESI-MS (M+H⁺)=707.

EXAMPLE 99

Preparation of Compound 99

Compound 99 was prepared by the procedures described follows:
8 ml of a 1 N LiOH aqueous solution at 0° C. was added to Intermediate 6 described in Example 1 (0.107 g, 0.243 mmol, 1 eq.) in THF (11 ml). The mixture was stirred at this temperature for 5 minutes, and then at room temperature for 1 hour. The reaction mixture was then partitioned between H₂O (10 ml) and EtOAc (10 ml). The aqueous layer was acidified to pH=2 with a 10% KHSO₄ aqueous solution and was extracted with EtOAc (2×10 ml). The organic layers were combined, dried over Na₂SO₄, and concentrated under vacuum to afford a crude corresponding carboxylic acid. Under an atmosphere of nitrogen, the carboxylic acid (0.100 g, 0.243 mmol, 1 eq.) was dissolved slowly in anhydrous DMF (1.2 ml, 0.2 M). After cesium carbonate (0.119 g, 0.365 mmol, 1.5 eq.) and benzyl bromide (0.062 g, 0.040 ml, 0.365 mmol, 1.5 eq.) were sequentially added into the above solution, the reaction mixture was stirred at ambient temperature overnight under N₂. The reaction was then quenched by addition of a 10% KHSO₄ aqueous solution (5 ml) slowly. The resultant solution was extracted with CH₂Cl₂ (5 ml×4). The organic layers were combined, washed with brine, dried over Na₂SO₄, and concentrated under vacuum to give a crude product. The crude product thus obtained was purified by flash chromatography (2% MeOH in CH₂Cl₂) on silica gel to afford Intermediate 8 (94 mg, 77%) as a white solid. ¹H NMR (CDCl₃) δ 0.85 (d, J=4.8 Hz, 6H), 1.19 (m, 1H), 1.32 (s, 9H), 1.38-1.71 (m, 4H), 1.95-2.08 (m, 2H), 2.25-2.30 (m, 2H), 3.19-3.27 (m, 2H), 4.15 (m, 1H), 4.51 (m, 1H), 5.08 (s, 2H), 5.88 (d, J=15.3 Hz, 1H), 6.57 (br s, 1H), 6.79 (dd, J=15.3, 4.8 Hz, 1H), 7.24 (m, 5H), 7.55(d, J=7.5 Hz, 1H). ESI-MS (M+H⁺)=502.

A 4.0 M solution of HCl in 1,4-dioxane (1.78 ml) was added to a solution of Intermediate 8 (0.094 g, 0.187 mmol, 1 eq.) in the same solvent (1.8 ml) at 23° C. After 2 hours of stirring, the reaction mixture was concentrated under reduced pressure. The residue thus obtained was dissolved in CH₂Cl₂ (15 ml). Z-Thr(t-Bu)-OH (0.058 g, 0.187 mmol, 1.0 eq.), 4-methylmorpholine (0.080 ml, 0.750 mmol, 4.0 eq.), HOBt (0.038 g, 0.281 mmol, 1.5 eq.), and EDC (0.054 g, 0.281 mmol, 1.5 eq.) were added sequentially. The resultant solution was stirred overnight at 23° C. and then the solvent was removed under vacuum. The residue was partitioned between a 10% KHSO₄ aqueous solution (1 ml) and CH₂Cl₂ (7 ml). The organic layer was dried over MgSO₄, filtered, and concentrated. The crude product thus obtained was purified by flash chromatography (70% EtOAc in hexanes) to afford compound 99 (0.117 g, 90%) as a white foam. ¹H NMR (CDCl₃) δ 0.94 (dd, J=8.4, 6.0 Hz, 6H), 1.05 (d, J=6.3 Hz, 3H), 1.25 (s, 9H), 1.46-1.80 (m, 6H), 1.99-2.06 (m, 1H), 2.38 (m, 1H), 3.27-3.30 (m, 2H), 4.15 (m, 2H), 4.40 (m, 1H), 4.58 (m, 1H), 5.04-5.15 (m, 4H), 5.87 (s, 2H), 5.96 (dd, J=15.9, 1.2 Hz, 1H), 6.86 (dd, J=15.6, 5,4 Hz, 1H), 7.28-7.33 (m, 10H), 7.61(d, J=7.2 Hz, 1H). ESI-MS (M+H⁺)=693.

EXAMPLE 100

Preparation of Compound 100

Compound 100 was prepared in a manner similar to that described in Example 1.
¹H NMR (CDCl₃) δ 0.90-096 (m, 6H), 1.02-1.04 (m, 3H), 1.24 (s, 9H), 1.49-1.69(m, 9H), 1.75-1.80 (m, 7H), 1.98-2.07 (m, 1H), 2.36 (m, 2H), 3.25-3.28 (m, 2H), 4.14 (m, 1H), 4.41 (m, 1H), 4.56 (m, 1H), 5.08 (s, 2H), 5.14-5.19 (m, 1H), 5.85-5.90 (m, 2H), 6.73-6.80 (m, 1H), 7.33 (m, 5H), 7.62 (m, 1H). ESI-MS (M+H⁺)=671.

EXAMPLE 101

Preparation of Compound 101

Compound 101 was prepared in a manner similar to that described in Example 1.

¹H NMR (CDCl₃) δ 1.07 (d, J=6.3 Hz, 3H), 1.28 (s, 9H), 1.66-1.73 (m, 4H), 2.21-2.50 (m, 8H), 2.88 (m, 2H), 3.20-3.30 (m, 2H), 4.16 (q, J=6.9 Hz, 2H), 4.42 (br, 1H), 4.58 (br, 1H), 5.01-5.10 (m, 3H), 5.91 (d, J=15.6 Hz, 1H), 6.82 (dd, J=15.3 Hz, 5.1 Hz, 1H), 7.2-7.34 (m, 4H), 7.60 (d, J=7.5 Hz, 1H). ESI-MS (M+H⁺)=632.

EXAMPLE 102

Preparation of Compound 102

Compound 102 was prepared in a 66% yield by reacting compound 112 with

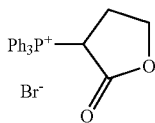

(1.5 eq.) via a Wittig reaction for 24 hours.

¹H NMR(CDCl₃) δ 0.93-0.98(m, 6H), 1.26(s, 9H), 1.66-1.73(m, 5H), 2.22-2.51(m, 4H), 3.19-3.30(m, 2H), 4.26(t, J=6.9 Hz, 2H), 4.44(br, 1H), 4.57(br, 1H), 5.12(s, 2H), 6.82(d, J=5.1 Hz, 1H), 7.22-7.34(m, 4H), 7.60(d, J=7.5 Hz, 1H). ESI-MS (M+H⁺)=629.

EXAMPLE 103

Preparation of Compound 103

Compound 103 was prepared in a manner similar to that described in Example 1 in a 63% yield.

¹H NMR(CDCl₃) δ 0.94-0.98 (m, 6H), 1.06 (d, 3H, J=5.7 Hz), 1.27 (s, 9H), 1.53-2.10 (m, 6H), 2.38-2.43 (m, 2H), 3.28-3.30 (m, 2H), 3.72 (s, 3H), 4.16 (br, 2H), 4.48 (m, 1H), 4.59 (m, 1H), 5.11 (q, 2H, J=6.6 Hz), 5.93 (d, 2H, J=15.9 Hz), 6.12 (br, 1H), 6.84 (dd, 1H, J=15.6 Hz, 5.1 Hz), 7.35-7.39 (m, 5H), 7.65 (d, 1H, J=6.9 Hz). ESI-MS (M+H⁺)=617.

EXAMPLE 104

Preparation of Compound 104

Compound 104 was prepared in a manner similar to that described in Example 1 in a 35% yield.

¹H NMR (CDCl₃) δ 0.93-0.98 (m, 12H), 1.06 (d, 4H, J=5.7 Hz), 1.27 (s, 9H), 1.53-2.16 (m, 7H), 2.39-2.43 (m, 2H), 3.28-3.34 (m, 2H), 3.90 (d, 2H, J=6.9 Hz), 4.16-4.18 (m, 2H), 4.47-4.49 (m, 1H), 4.60 (br, 1H), 5.1 (q, 2H, J=6.9 Hz), 5.89 (d, 1H, J=5.4 Hz), 5.94 (d, 1H, J=15.6 Hz), 6.08 (s, 1H), 6.83 (dd, 1H, J=15.6 Hz, 5.1 Hz), 7.31-7.40 (m, 5H), 7.63 (d, 1H, J=7.5 Hz). ESI-MS (M+H⁺)=659.

EXAMPLE 105

Preparation of Compound 105

Compound 105 was prepared in a manner similar to that described in Example 1 in a 79% yield.

¹H NMR (CDCl₃) δ 0.93-0.98 (m, 6H), 1.05 (d, 3H, J=5.4 Hz), 1.26 (s, 9H), 1.53-2.11 (m, 7H), 2.37 (br, 2H), 3.28-3.33 (m, 2H), 4.16 (br, 2H), 4.50-4.52 (m, 2H), 4.62 (d, 2H, J=5.7 Hz), 5.10 (q, 2H, J=6.6 Hz), 5.23 (d, 1H, J=10.2 Hz), 5.31 (d, 1H, J=17.4 Hz), 5.85-5.98 (m, 3H), 6.86 (dd, 1H, J=15.6 Hz, 5.4 Hz), 7.35-7.41 (m, 5H), 7.69-7.74 (m, 1H). ESI-MS (M+H⁺)=643.

EXAMPLE 106

Preparation of Compound 106

Compound 106 was prepared in a manner similar to that described in Example 1 in a 92% yield.

¹H NMR (CDCl₃) δ 0.92-0.97 (m, 6H), 1.1 (d, 3H, J=6 Hz), 1.28 (s, 9H), 1.52-2.19 (m, 6H), 2.43 (br, 2H), 3.19 (s, 3H), 3.28-3.30 (m, 2H), 3.78 (s, 3H), 4.17-4.19 (m, 2H), 4.38 (br, 1H), 4.90-4.95 (m, 1H), 5.10 (q, 2H, J=8.7 Hz), 5.96 (m, 2H), 7.30-7.35 (m, 5H), 7.44 (d, 1H, J=7.8 Hz). ESI-MS (M+H⁺)=620.

EXAMPLE 107

Preparation of Compound 107

Compound 107 was prepared in a 88% yield by reducing compound 103 with LiBH₄ (1.5 eq.).

¹H NMR(CDCl₃) δ 0.92-0.99(m, 6H), 1.26(s, 9H), 1.66-1.73(m, 5H), 2.21-2.50(m, 2H), 3.20-3.32(m, 2H), 3.62(m, 1H), 3.75(d, J=7.5 Hz, 2H), 4.42(br, 1H), 4.58(br, 1H), 5.10(s, 2H), 7.21-7.34(m, 4H), 7.61(d, J=7.5 Hz, 1H). ESI-MS (M+H⁺)=563.

EXAMPLE 108

Preparation of Compound 108

Compound 108 was prepared in a manner similar to that described in Example 1.
ESI-MS (M+H⁺)=612.

EXAMPLE 109

Preparation of Compound 109

Compound 109 was prepared as follows: Dry THF (5 ml) and 1-methyl-1-propenyl magnesium bromide (0.5 M in THF, 22 ml) were added to compound 106 (0.124 g, 0.2 mmol) under N₂. The mixture was stirred at room temperature under N₂ for 30 minutes, and then quenched by slowly adding a 10% HCl solution until the pH value was about 7. The mixture was then washed with brine and extracted with EtOAc (3×50 ml). The organic layers were combined, and dried with Na₂SO₄. The crude product was purified by silica gel chromatography using 2% MeOH/CH₂Cl₂ as an eluant to afford compound 109 as a white solid (0.085 mg, 69%).

¹H NMR (CDCl₃) δ 0.91-0.96 (m, 6H), 1.09 (d, 3H, J=6 Hz), 1.28 (s, 9H), 1.49-1.83 (m, 5H), 1.79 (s, 3H), 1.89 (d, 3H, J=6.9 Hz), 2.03-2.13 (m, 1H), 2.30-2.41 (m, 1H), 2.48 (m, 1H), 3.25-3.30 (m, 2H), 4.17-4.19 (m, 2H), 4.38-4.39 (m, 1H), 5.11 (q, 2H, J=7.8 Hz), 5.33-5.38 (m, 1H), 5.92-5.97 (m, 2H), 6.85 (q, 1H, J=6.3 Hz), 7.13-7.15 (m, 1H), 7.30-7.35 (m, 5H), 7.42 (d, 1H, J=7.8 Hz). ESI-MS (M+H¹)=615.

EXAMPLE 110

Preparation of Compound 110

Compound 110 was prepared in a manner similar to that of compound 109 in a 44% yield.

¹H NMR (CDCl₃) δ 0.95 (m, 6H), 1.09 (d, 3H, J=6.6 Hz), 1.27 (s, 9H), 1.52-1.85 (m, 5H), 2.05-2.14 (m, 1H), 2.38-2.42 (m, 2H), 3.28-3.33 (m, 2H), 4.17-4.19 (m, 2H), 4.40-4.42 (m, 1H), 4.79-4.84 (m, 1H), 5.11 (q, 2H, J=7.8 Hz), 5.84-5.92 (m, 3H), 6.36-6.56 (m, 2H), 7.31-7.35 (m, 5H), 7.42 (d, 1H, J=7.8 Hz), 7.61 (d, 1H, J=7.2 Hz). ESI-MS (M+H⁺)=587.

EXAMPLE 111

Preparation of Compound 111

Compound 111 was prepared in a manner similar to that of compound 109.

¹H NMR (CDCl₃) δ 0.96 (m, 6H), 1.08 (d, 3H, J=5.7 Hz), 1.27 (s, 9H), 1.54-1.78 (m, 5H), 2.03-2.07 (m, 1H), 2.25 (s, 3H), 2.40 (m, 2H), 3.28-3.32 (m, 2H), 4.16-4.19 (m, 2H), 4.60-4.61 (m, 1H), 5.11 (q, 2H, J=6.3 Hz), 5.88 (d, 1H, J=4.8 Hz), 6.02 (s, 1H), 6.16 (d, 1H, J=16.2 Hz), 6.66 (dd, 1H, J=15.9 Hz, 5.1 Hz), 7.35 (m, 5H), 7.73 (d, 1H, J=7.5 Hz). ESI-MS (M+H⁺)=601.

EXAMPLE 112

Preparation of Compound 112

Compound 112 was prepared in a 99% yield by reacting compound 107 with SO₃Py (2.5 eq.) via a Swem oxidation reaction for 1 hour.

¹H NMR (CDCl₃) δ 0.92-0.98 (m, 6H), 1.26 (s, 9H), 1.66-1.73 (m, 5H), 2.21-2.50 (m, 2H), 3.20-3.32 (m, 2H), 4.42 (br, 2H), 4.59 (br, 1H), 5.11 (s, 2H), 7.21-7.34 (m, 4H), 7.61 (d, J=7.5 Hz, 1H), 9.82 (s, 1H). ESI-MS (M+H⁺)=561.

EXAMPLE 113

Preparation of Compound 113

Compound 113 was prepared in a 68% yield in a manner similar to that of compound 89 using compound 102 as a starting material.

¹H NMR (CDCl₃) δ 0.94-0.99 (m, 6H), 1.25 (s, 9H), 1.66-1.73 (m, 5H), 2.22-2.51 (m, 4H), 3.19-3.30 (m, 2H), 4.26 (t, J=6.9 Hz, 2H), 4.44 (br, 1H), 4.57 (br, 1H), 5.12 (s, 2H), 6.82 (d, J=5.1 Hz, 1H), 7.22-7.34 (m, 4H), 7.61 (d, J=7.5 Hz, 1H). ESI-MS (M+H⁺)=657.

EXAMPLE 114

Preparation of Compound 114

Methylsulfoxide and triethylamine were added to a solution of compound 107. The solution was cooled to 0-5° C. with an ice-water bath, followed by addition of sulfur trioxide-pyridine complex. The reaction mixture was stirred at that temperature for 1 hour. After adding

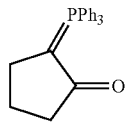

and stirring the reaction mixture at ambient temperature for another 3 hours, the reaction mixture was quenched by addition of saturated brine and subsequently extracted with ethyl acetate. The organic layers were combined, dried over MgSO₄, filtered, and concentrated to afford a dark red oil. The oil was purified though a chromatography (50% EA in hexane) to afford compound 114 as a white solid.

ESI-MS (M+H⁺)=627.

EXAMPLE 115

Preparation of Compound 115

Compound 115 was prepared in a manner similar to that described in Example 1 in a 65% yield.

¹H NMR (CDCl₃) δ 0.90-095 (m, 6H), 1.03-1.05 (m, 4H), 1.23 (s, 9H), 1.44-1.88 (m, 5H), 1.97 (m, 2H), 2.37 (m, 2H), 3.24-3.32 (m, 2H), 3.69 (s, 3H), 4.14 (m, 1H), 4.40-4.52 (m, 2H), 5.07 (s, 2H), 5.88-5.91 (m, 1H), 6.23 (m, 1H), 7.33 (m, 5H), 7.45 (m, 1H), 7.77 (m, 1H). ESI-MS (M+H⁺)=591.

EXAMPLE 116

Preparation of Compound 116

Compound 116 was prepared in a 77% yield in a manner similar to that of compound 109 using compound 106 as a starting material.

¹H NMR (CDCl₃) δ 0.94-0.99 (m, 6H), 1.09 (d, 3H, J=6 Hz), 1.27 (s, 9H), 1.53-1.84 (m, 5H), 2.02-2.12 (m, 1H), 2.20 (s, 3H), 2.32-2.43 (m, 2H), 3.24-3.35 (m, 2H), 5.11 (q, 2H, J=6 Hz), 5.90 (d, 1H, J=3 Hz), 5.98 (m, 1H), 7.32-7.36 (m, 5H), 7.42 (d, 1H, J=6 Hz), 7.83 (d, 1H, J=9 Hz). ESI-MS (M+H⁺)=575.

EXAMPLE 117

Preparation of Compound 117

Compound 117 was prepared by the procedures described below:

Triethylamine (0.25 ml, 1.757 mmol, 4.53 eq.) was added to a solution of Intermediate 4 described in Example 1 (0.100 g, 0.387 mmol, 1 eq.) in DMSO (1.1 ml). The solution was cooled to 0° C. with an ice bath, followed by addition of sulfur trioxide-pyridine complex (0.568 g, 1.742 mmol, 4.5 eq.). The ice bath was removed after the addition and the reaction mixture was stirred at room temperature for 1 hour. 1-Acetyl-3-(triphenyl-15-phosphanylidene)-pyrrolidin-2-one (0.600 g, 1.548 mmol, 4 eq.) was then added into the mixture. After stirring the mixture at room temperature overnight, the reaction was quenched by saturated brine (7 ml) and then extracted with ethyl acetate (3×10 ml). The organic layers were combined, washed with saturated brine (3×15 ml), dried over MgSO₄, filtered, and concentrated to afford a dark red oil. The oil was purified through a column chromatography (2% MeOH in CH₂Cl₂) to afford Intermediate 9 as a white solid (75 mg, 53%). ESI-MS (M+H⁺)=366.

Intermediate 9 (0.446 g, 1.220 mmol, 1 eq.) was dissolved in a solution of HCl in 1,4-dioxane (4.0 M, 10 ml) was added to. The solution was stirred at room temperature for 30 minutes and 1,4-dioxane was removed under vacuum. CH₂Cl₂ (1.5 ml) was then added to the residue, followed by addition of N-methylmorpholine (0.540 ml, 4.880 mmol, 4 eq.), Z-Thr (t-Bu)-Leu-OH (0.515 g, 1.220 mmol, 1.0 eq.), HOBt (0.250 g, 1.830 mmol, 1.5 eq.), and EDC (0.351 g, 1.830 mmol, 1.5 eq.). The reaction mixture was stirred at room temperature overnight and then concentrated under vacuum. The residue was partitioned between a 10% KHSO₄ (6.5 ml) aqueous solution and CH₂Cl₂ (45 ml). The organic layer was collected, dried over MgSO₄, filtered, and concentrated. The crude product was purified by flash chromatography (2% MeOH in CH₂Cl₂) to afford compound 117 (0.572 g, 70%) as a white solid. ¹H NMR (CDCl₃) δ 0.88-0.98 (m, 6H), 1.07 (d, J=6.0 Hz, 3H), 1.25 (s, 9H), 1.48-1.62 (m, 3H), 1.74-1.90 (m, 3H), 2.06-2.16 (m, 3H), 2.32-2.47 (m, 3H), 2.54 (s, 3H), 2.71 (m, 1H), 3.03 (m, 1H), 3.27-3.30 (m, 2H), 3.77 (dd, J=7.5, 7.5 Hz, 2H), 4.14-4.18 (m, 2H), 4.53 (m, 1H), 4.60 (m, 1H), 5.00-5.18 (m, 2H), 5.87 (d, J=5.1 Hz, 1H), 6.02 (br s, 1H), 6.43 (d, J=9.0 Hz, 1H), 7.27-7.34 (m, 5H), 7.76 (d, J=6.9 Hz, 1H). ESI-MS (M+H$^+$)=670.

EXAMPLE 118

Preparation of Compound 118

Compound 118 was prepared in a manner similar to that described in Example 1.

$^1$H NMR (CDCl$_3$) δ 0.9 (m, 6H), 1.16 (s, 9H), 1.49-2.17 (m, 8H), 2.38-2.41 (m, 2H), 3.32-3.35 (m, 2H), 3.58-3.70 (m, 2H), 4.27-4.28 (m, 1H), 4.37 (t, 3H, J=7.5 Hz), 4.57 (br, 1H), 5.10 (q, 2H, J=5.7 Hz), 6.30 (s, 1H), 6.49-6.52 (m, 2H), 6.63-6.65 (m, 1H), 7.16 (d, 1H, J=8.4 Hz), 7.34 (br, 5H), 8.17 (d, 1H, J=6.3 Hz). ESI-MS (M+H$^+$)=642.

EXAMPLE 119

Preparation of Compound 119

Compound 119 was prepared in a manner similar to that described in Example 1.
ESI-MS (M+H$^+$)=657.

EXAMPLE 120

Preparation of Compound 120

Compound 120 was prepared in a manner similar to that described in Example 1.

$^1$H NMR (CDCl$_3$) δ 0.85-0.90 (m, 6H), 1.39 (s, 9H), 1.56-1.81 (m, 5H), 2.01-2.09 (m, 4H), 2.41 (m, 1H), 3.16 (s, 3H), 3.28-3.30 (m, 2H), 3.44-3.48 (m, 2H), 3.78 (s, 3H), 4.30-4.40 (m, 2H), 4.83-4.88 (m, 1H), 5.09 (s, 2H), 5.64 (br s, 1H), 6.32 (br s, 1H), 7.26-7.33 (m, 5H), 7.77-7.79 (m, 1H). ESI-MS (M+H$^+$)=645.

EXAMPLE 121

Preparation of Compound 121

Compound 121 was prepared in a manner similar to that described in Example 1 in a 10% yield.

$^1$H NMR (CDCl$_3$) δ 0.87 (m, 6H), 1.26 (s, 9H), 1.53-1.76 (m, 5H), 1.99 (m, 6H), 2.38 (m, 2H), 2.88 (m, 1H), 3.14-3.48 (m, 4H), 4.14 (m, 1H), 4.35 (m, 2H), 4.56 (m, 1H), 5.07 (s, 2H), 6.40-6.46 (m, 1H), 7.04 (m, 1H), 7.31 (m, 5H), 8.08 (m, 1H). ESI-MS (M+H$^+$)=657.

EXAMPLE 122

Preparation of Compound 122

Compound 122 was prepared in a manner similar to that of compound 109 in a 60% yield.

$^1$H NMR (CDCl$_3$) δ 0.93 (m, 6H), 1.16 (s, 9H), 1.45-1.82 (m, 5H), 2.00-2.09 (m, 1H), 2.45 (s, 3H), 2.37-2.46 (m, 2H), 3.31-3.34 (m, 2H), 3.64-3.68 (m, 2H), 4.27-4.29 (m, 1H), 4.44-4.50 (m, 1H), 4.59-4.60 (m, 1H), 5.10 (q, 2H, J=5.1 Hz), 6.10 (s, 1H), 6.17 (d, 1H, J=1.2 Hz), 6.48 (br, 1H), 6.68 (dd, 2H, J=15.6 Hz, 5.7 Hz), 7.13 (d, 1H, J=8.1 Hz), 7.34 (br, 5H), 8.01 (d, 1H, J=6.9 Hz). ESI-MS (M+H$^+$)=614.

EXAMPLE 123

Preparation of Compound 123

Compound 123 was prepared in a manner similar to that of compound 109 in a 32% yield.

$^1$H NMR (CDCl$_3$) δ 0.92-0.98 (m, 6H), 1.06-1.11 (m, 6H), 1.26 (s, 9H), 1.53-2.10 (m, 6H), 2.39 (m, 2H), 2.56 (q, 2H, J=7.2 Hz), 3.28-3.31 (m, 2H), 4.15-4.18 (m, 2H), 4.44-4.45 (m, 1H), 4.58 (m, 1H), 5.11 (q, 2H, J=6.3 Hz), 5.89 (d, 1H, J=4.8 Hz), 6.04 (s, 1H), 6.19 (d, 1H, J=15.3 Hz), 6.69 (dd, 1H, J=15.9 Hz, 5.4 Hz), 7.35 (m, 5H), 7.71 (d, 1H, J=7.5 Hz). ESI-MS (M+H$^+$)=615.

EXAMPLE 124

Preparation of Compound 124

Compound 124 was prepared in a manner similar to that described in Example 1.
ESI-MS (M+H$^+$)=615.

EXAMPLE 125

Preparation of Compound 125

Compound 125 was prepared in a manner similar to that of compound 109 in a 55% yield.

$^1$H NMR (CDCl$_3$) δ 0.91 (q, 6H, J=6 Hz), 1.41 (s, 9H), 1.55-1.81 (m, 5H), 2.10 (m, 1H), 2.23 (s, 3H), 2.36-2.40 (m, 2H), 2.78 (m, 2H), 3.30-3.33 (m, 2H), 4.46-4.52 (m, 1H), 4.56-4.59 (m, 2H), 5.11 (q, 2H, J=6.6 Hz), 6.01 (d, 1H, J=8.4 Hz), 6.15 (d, 1H, J=15.6 Hz), 6.30 (s, 1H), 6.65 (dd, 1H, J=16.2 Hz, 5.4 Hz), 7.17 (d, 1H, J=8.4 Hz), 7.34 (m, 5H), 7.89 (d, 1H, J=7.8 Hz). ESI-MS (M+Na$^+$)=637.

EXAMPLE 126

Preparation of Compound 126

Compound 126 was prepared in a manner similar to that of compound 109 in an 82% yield.

$^1$H NMR (CDCl$_3$) δ 0.86-0.97 (m, 6H), 1.14-1.38 (m, 6H), 1.49-1.66 (m, 1H), 1.98-2.08 (m, 2H), 2.23 (s, 3H), 2.34-2.45 (m, 2H), 3.29-3.33 (m, 2H), 3.62-3.68 (m, 2H), 4.26 (dd, J=9.9, 5.4 Hz, 1H), 4.43 (m, 1H), 4.59 (m, 1H), 5.04-5.14 (m, 2H), 6.08-6.18 (m, 2H), 6.37 (br s, 1H), 6.64-6.71 (dd, J=16.2, 5.4 Hz, 2H), 7.13 (d, J=8.4 Hz, 1H), 7.28-7.34 (m, 5H), 7.98 (d, J=6.9 Hz, 1H). ESI-MS (M+H$^+$)=640.

EXAMPLE 127

Preparation of Compound 127

Compound 127 was prepared in a manner similar to that of compound 109 in a 78% yield.

$^1$H NMR (CDCl$_3$) δ 0.85-0.93 (m, 6H), 0.98 (s, 9H), 1.48-1.64 (m, 4H), 1.75-1.85 (m, 1H), 1.91 (m, 1H), 1.98-2.08 (m, 1H), 2.03 (s, 3H), 2.23 (s, 3H), 2.37-2.46 (m, 2H), 3.29-3.36 (m, 2H), 3.54-3.72 (m, 2H), 4.24 (m, 1H), 4.44 (m, 1H), 4.58 (m, 1H), 5.02-5.12 (m, 2H), 6.15 (d, J=15.9 Hz, 1H), 6.55-6.78 (m, 3H), 7.28-7.31 (m, 5H), 7.97 (d, J=6.6 Hz, 1H). ESI-MS (M+H$^+$)=628.

EXAMPLE 128

Preparation of Compound 128

Compound 128 was prepared in a manner similar to that of compound 109 in a 25% yield.

$^1$H NMR (CDCl$_3$) δ 0.89 (m, 6H), 1.39 (s, 9H), 1.53-2.14 (m, 7H), 2.22 (s, 3H), 2.39 (m, 2H), 3.29-3.30 (m, 2H), 3.46 (m, 2H), 4.21 (m, 2H), 4.43 (m, 1H), 4.58 (m, 1H), 5.09 (s, 2H), 6.18 (m, 2H), 6.46 (m, 1H), 6.62-6.69 (m, 1H), 7.32 (m, 5H), 7.93 (m, 1H). ESI-MS (M+H$^+$)=630.

EXAMPLE 129

Preparation of Compound 129

Compound 129 was prepared in a manner similar to that of compound 112 in a 38% yield.
$^1$H NMR (CDCl$_3$) δ 0.92-0.98(m, 6H), 1.27(s, 9H), 1.65-1.72(m, 5H), 2.22-2.51(m, 2H), 3.20-3.32(m, 2H), 4.43(br, 2H), 4.59(br, 1H), 5.12(s, 2H), 7.21-7.35 (m, 4H), 7.60(d, J=7.5 Hz, 1H), 9.82(s, 1H) ESI-MS (M+H$^+$)=604.3.

EXAMPLE 130

Preparation of Compound 130

Compound 130 was prepared in a manner similar to that of compound 131.
$^1$H NMR (CDCl$_3$) δ 0.93-0.98(m, 6H), 1.26(s, 9H), 1.65-1.72(m, 5H), 2.22-2.51(m, 2H), 3.20-3.32(m, 2H), 3.58(d, J=7.2 Hz, 2H), 3.86(m, 1H), 4.44(br, 2H), 5.12(s, 2H), 7.21-7.35(m, 4H), 7.60(d, J=7.5 Hz, 1H). ESI-MS (M+H$^+$)=624.3.

EXAMPLE 131

Preparation of Compound 131

Compound 131 was prepared in a 51% yield by reacting compound 107 with thionyl chloride in CH$_2$Cl$_2$ at room temperature for 6 hours.
$^1$H NMR (CDCl$_3$) δ 0.93-0.98(m, 6H), 1.28(s, 9H), 1.65-1.72(m, 5H), 2.22-2.50(m, 2H), 3.20-3.32(m, 2H), 3.58(d, J=7.2 Hz, 2H), 3.86(m, 1H), 4.42(br, 2H), 5.11(s, 2H), 7.21-7.35(m, 4H), 7.60(d, J=7.5 Hz, 1H). ESI-MS (M+H$^+$)=581.3.

EXAMPLE 132

Preparation of Compound 132

1-(2,2,2-Trifluoro-1-methyl-ethylidene)-pyrrolidinium (1.5 eq.) was prepared from methyltrifluoromethylketone and pyrrolidine at 0° C. Compound 112 (1.0 eq.) was then added in situ to afford compound 132 in a 43% yield.
$^1$H NMR (CDCl$_3$) δ 0.94-0.98(m, 6H), 1.27(s, 9H), 1.66-1.73(m, 5H), 2.25-2.53(m, 2H), 3.22-3.31(m, 2H), 4.44(m, 1H), 4.63(m, 1H), 5.10(s, 2H), 6.21(d, J=18.1 Hz, 1H), 6.98 (dd, J=18.1 Hz, 5.1 Hz, 1H), 7.22-7.35(m, 4H), 7.62(d, J=7.5 Hz, 1H). ESI-MS (M+H$^+$)=655.

EXAMPLE 133

Preparation of Compound 133

Compound 133 was prepared in a manner similar to that of compound 112 in a 35% yield.
$^1$H NMR (CDCl$_3$) δ 0.89-0.95 (m, 6H), 1.42 (s, 9H), 1.55-2.06 (m, 6H), 2.37-2.47 (m, 2H), 2.64-2.94 (m, 2H), 3.32-3.34 (m, 2H), 4.45-4.58 (m, 3H), 5.12 (s, 2H), 6.00-6.16 (m, 2H), 7.35 (m, 5H), 9.49 (d, 1H, J=16.5 Hz). ESI-MS (M+H$^1$)=575.

EXAMPLE 134

Preparation of Compound 134

Compound 134 was prepared in a manner similar to that of compound 112 in a 35% yield.

$^1$H NMR (CDCl$_3$) δ 0.87-1.26 (m, 20H), 1.69-1.97 (m, 14H), 2.43 (m, 1H), 3.64 (m, 1H), 4.18 (m, 2H), 4.40 (m, 1H), 5.09 (s, 2H), 5.90 (m, 1H), 7.36 (m, 5H), 9.50 (s, 1H). ESI-MS (M+H$^+$)=601.

EXAMPLE 135

Preparation of Compound 135

Compound 135 was prepared in a manner similar to that of compound 109.
$^1$H NMR (CDCl$_3$) δ 0.93 (q, 6H, J=5.7 Hz), 1.03-1.08 (m, 9H), 1.23 (s, 9H), 1.49-1.83 (m, 5H), 2.00-2.03 (m, 1H), 2.36 (m, 2H), 2.70-2.79 (m, 1H), 3.26-3.29 (m, 2H), 4.13-4.17 (m, 2H), 4.43-4.44 (m, 1H), 4.58-4.60 (m, 1H), 5.09 (q, 2H, J=5.4 Hz), 5.86 (d, 1H, J=5.1 Hz), 6.01 (s, 1H), 6.26 (d, 1H, J=15.6 Hz), 6.71 (dd, 1H, J=15.6 Hz, 5.4 Hz), 7.30-7.34 (m, 5H), 7.60 (d, 1H, J=7.8 Hz). ESI-MS (M+H$^+$)=629.

EXAMPLE 136

Preparation of Compound 136

Compound 136 was prepared in a manner similar to that of compound 109 in a 36% yield.
$^1$H NMR (CDCl$_3$) δ 0.93 (q, 6H, J=5.7 Hz), 1.06 (d, 3H, J=6.3 Hz), 1.23 (s, 9H), 1.44-1.77 (m, 5H), 1.99-2.07 (m, 1H), 2.39 (m, 2H), 3.27-3.30 (m, 2H), 4.15-4.18 (m, 2H), 4.39-4.41 (m, 1H), 4.62 (m, 1H), 5.10 (q, 2H, J=6 Hz), 5.82-5.87 (m, 3H), 6.28 (d, 1H, J=16.5 Hz). 6.47-6.56 (m, 2H), 6.77 (dd, 1H, J=15.3 Hz, 4.8 Hz), 7.29-7.34 (m, 5H), 7.66 (d, 1H, J=7.5 Hz). ESI-MS (M+Na$^+$)=635.

EXAMPLE 137

Preparation of Compound 137

Compound 137 was prepared in a manner similar to that of compound 109.
$^1$H NMR (CDCl$_3$) δ 0.94-0.97 (m, 6H), 1.08 (d, 3H, J=6.3 Hz), 1.27 (s, 9H), 1.52-1.86 (m, 11H), 2.02-2.09 (m, 1H), 2.40 (m, 2H), 3.29-3.32 (m, 2H), 4.16 (m, 2H), 4.41 (m, 1H), 4.62 (m, 1H), 5.11 (q, 2H, J=5.4 Hz), 5.81-5.89 (m, 2H), 6.61-6.79 (m, 3H), 7.35 (m, 5H), 7.53 (d, 1H, J=7.2 Hz). ESI-MS (M+H$^+$)=641.

EXAMPLE 138

Preparation of Compound 138

Compound 138 was prepared in a manner similar to that of compound 109 in a 26% yield.
$^1$H NMR (CDCl$_3$) δ 0.87-1.26 (m, 20H), 1.52-1.72 (m, 9H), 2.21-2.22 (m, 3H), 2.38 (m, 2H), 3.27-3.30 (m, 2H), 4.15 (m, 2H), 4.39 (m, 1H), 4.58 (m, 1H), 5.09 (s, 2H), 5.86 (m, 2H), 6.12-6.22 (m, 1H), 6.61-6.68 (m, 1H), 7.33 (m, 5H), 7.65 (m, 1H). ESI-MS (M+H$^+$)=641.

EXAMPLE 139

Preparation of Compound 139

Compound 139 was prepared in a manner similar to that of compound 109 in a 28% yield.
$^1$H NMR (CDCl$_3$) δ 0.62-0.70 (m, 8H), 0.79-0.80 (m, 6H), 0.99 (s, 9H), 1.26-1.85 (m, 6H), 2.12 (m, 2H), 3.00-3.03 (m, 2H), 4.16 (m, 2H), 4.46 (m, 1H), 4.62 (m, 1H), 5.06-5.16 (m, 2H), 5.89 (s, 1H), 6.10 (s, 1H), 6.32 (d, 1H, J=15.6 Hz), 6.74 (dd, 1H, J=15.6 Hz, 5.1 Hz), 7.36 (m, 5H), 7.69 (m, 1H). ESI-MS (M+Na$^+$)=649.

EXAMPLE 140

Preparation of Compound 140

Compound 140 was prepared in a manner similar to that of compound 109 in a 37% yield.
$^1$H NMR (CDCl$_3$) δ 0.93 (q, 6H, J=6 Hz), 1.04 (d, 3H, J=6 Hz), 1.23 (s, 9H), 1.49-1.83 (m, 5H), 1.89 (s, 3H), 1.99-2.09 (m, 1H), 2.37-2.42 (m, 2H), 3.27 (d, 2H, J=9 Hz), 4.12-4.17 (m, 2H), 4.39-4.44 (m, 1H), 4.58-4.63 (m, 1H), 5.09 (q, 2H, J=5.4 Hz), 5.78 (s, 1H), 5.86 (d, 1H, J=5.1 Hz), 5.94 (s, 1H), 6.00 (m, 2H), 6.72-6.74 (m, 2H), 7.30-7.34 (m, 5H), 7.63 (d, 1H, J=7.5 Hz). ESI-MS (M+H$^+$)=627.

EXAMPLE 141

Preparation of Compound 141

Compound 141 was prepared in a manner similar to that of compound 109 in a 82% yield.
$^1$H NMR (CDCl$_3$) δ 0.86-1.02 (m, 15H), 1.09-1.31 (m, 9H), 1.45-1.85 (m, 6H), 2.16-2.24 (m, 2H), 2.22 (s, 3H), 2.30-2.41 (m, 2H), 3.22-3.32 (m, 2H), 4.10 (dd, J=5.4, 5.4 Hz, 1H), 4.23 (ddd, J=8.1, 6.0, 2.4 Hz, 1H), 4.46 (m, 1H), 4.63 (m, 1H), 4.99-5.14 (m, 2H), 5.38 (d, J=5.1 Hz, 1H), 5.88 (br s, 1H), 6.69 (dd, J=15.9, 5.1 Hz, 1H), 7.14 (d, J=6.0 Hz, 1H), 7.32-7.37 (m, 5H), 7.43 (m, 1H). ESI-MS (M+H$^+$)=700.

EXAMPLE 142

Preparation of Compound 142

Compound 142 was prepared in a manner similar to that described in Example 1.
$^1$H NMR (CDCl$_3$) δ 0.73-0.87 (m, 5H), 1.03 (d, J=6.0 Hz, 3H), 1.05 (d, J=6.0 Hz, 3H), 1.14 (s, 3H), 1.22-1.28 (m, 18H), 1.77-1.82 (m, 1H), 2.04-2.12 (m, 1H), 2.32-2.48 (m, 2H), 3.28-3.32 (m, 2H), 4.13-4.19 (m, 6H), 4.32-4.35 (m, 1H), 4.69-4.78 (m, 1H), 5.05-5.16 (m, 2H), 5.50 (br s, 1H), 5.89 (d, J=18, 1H), 6.13 (d, J=16 Hz, 1H), 6.85 (dd, J=16.0, 5.5 Hz, 1H), 7.08 (d, J=9.0 Hz, 1H), 7.34 (m, 5H), 7.63 (d, J=6.0 Hz, 1H). ESI-MS (M+Na$^+$)=675.

EXAMPLE 143

Preparation of Compound 143

Compound 143 was prepared in a manner similar to that of compound 109 in a 82% yield.
$^1$H NMR (CDCl$_3$) δ 0.84-0.94 (m, 6H), 1.10 (d, J=6.0 Hz, 3H), 1.15-1.24 (m, 5H), 1.49-1.79 (m, 10H), 2.03 (m, 1H), 2.22 (s, 3H), 2.38 (m, 2H), 3.28-3.31 (m, 2H), 3.39 (m, 1H), 4.15 (m, 2H), 4.45-4.58 (m, 2H), 5.09 (s, 2H), 5.75 (d, J=5.7 Hz, 1H), 5.90 (br s, 1H), 6.15 (d, J=15.9 Hz, 1H), 6.65 (dd, J=15.9, 5.4 Hz, 1H), 7.12 (d, J=7.8 Hz, 1H), 7.30-7.34 (m, 5H), 7.75 (d, J=7.5 Hz, 1H). ESI-MS (M+H$^+$)=627.

EXAMPLE 144

Preparation of Compound 144

Compound 144 was prepared in a manner similar to that described in Example 1.
$^1$H NMR (CDCl$_3$) δ 0.86-1.27 (m, 17H), 1.47-1.76 (m, 14H), 1.97-2.05 (m, 1H), 2.38 (br s, 2H), 3.28 (m, 2H), 4.15 (m, 4H), 4.38 (m, 1H), 4.58 (m, 1H), 5.04-5.14 (m, 2H), 5.79-5.93 (m, 3H), 6.80 (dd, 1H, J=15.9 Hz, 5.7 Hz), 7.34 (m, 5H), 7.60 (m, 1H). ESI-MS (M+H$^+$)=671.

EXAMPLE 145

Preparation of Compound 145

Compound 145 was prepared in a manner similar to that of compound 109 in a 25% yield.
$^1$H NMR (CDCl$_3$) δ 0.73-0.87 (m, 5H), 0.95 (d, J=6.0 Hz, 3H), 1.14 (s, 9H), 1.47-1.69 (m, 13H), 1.90-1.99 (m, 3H), 2.00-2.36 (m, 3H), 3.17 (m, 2H), 4.05 (m, 2H), 4.30 (m, 1H), 4.51 (m, 1H), 4.94-5.04 (m, 2H), 5.77-5.81 (m, 2H), 6.21 (d, J=16.0 Hz 1H), 6.62 (dd, J=16.0, 5.5 Hz, 1H), 7.34 (m, 5H), 7.52 (d, J=7.8 Hz, 1H). ESI-MS (M+Na$^+$)=667.

EXAMPLE 146

In Vitro Assay

A fusion protein, prepared by fusing a severe acute respiratory syndrome 3CL protease to *E. coli* maltose-binding protein (MBP), was expressed in *E coli* BL21 (DE3) pLys S cells (Novagen, Oakland, Calif.). Fusion protein thus obtained was purified by amylose-affinity chromatography and cleaved with factor Xa to release the severe acute respiratory syndrome 3CL protease. Subsequently, the recombinant protease was purified to homogeneity using phenyl Sepharose CL-4B column (Pharmacia, Uppsala, Sweden) and was concentrated to form a 25 μM solution.

The enzymatic activity of severe acute respiratory syndrome 3CL protease (75 nM) was determined by incubation with a solution containing 15 μM of a substrate peptide (SITSAVLQSGFRKMA, SEQ ID No: 1) at 25° C. for 30 minutes in a medium containing 20 mM Tris-HCl (pH 7.5), 200 mM NaCl, 1 mM EDTA, 1 mM dithiothretol, and 1 mg/mL bovine serum albumin. The reaction was terminated by adding an equal volume of 0.2% trifluoroacetic acid. The reaction mixture was analyzed by reverse-phase HPLC using a C18 column. Cleaved products were resolved using a 5-95% linear gradient of acetonitrile in 0.9% trifluoroacetic acid. Quantification of peak areas was used to determine the extent of substrate conversion.

Compounds 1-145 were tested for their efficacy in inhibiting severe acute respiratory syndrome 3CL protease. Specifically, a test compound and the severe acute respiratory syndrome 3CL protease were pre-incubated at 25° C. for 20 minutes before they were incubated with the substrate peptide. Unexpectedly, 77 compounds show IC$_{50}$ values lower than 1 μM, 32 compounds show IC$_{50}$ values between 1 μM and 10 μM, and 12 compounds show IC$_{50}$ values above 10 μM.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound, wherein the compound is
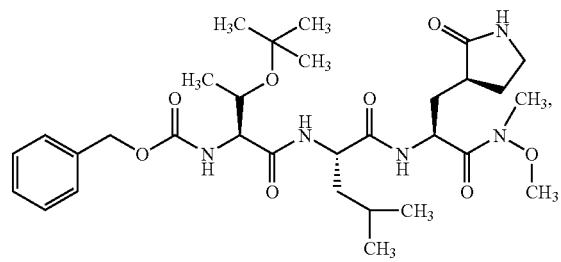
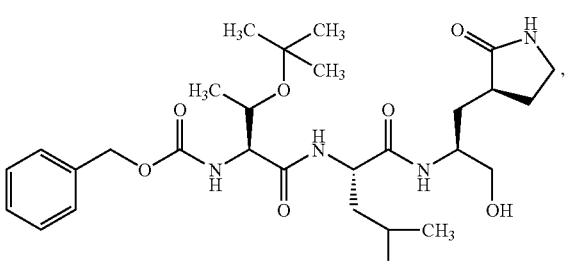
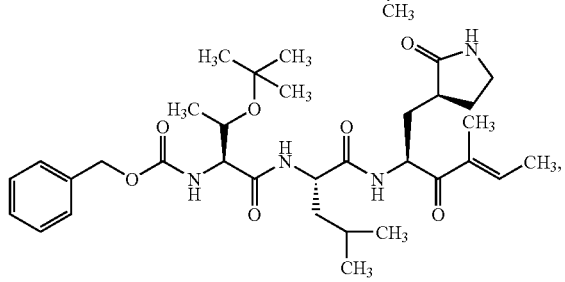
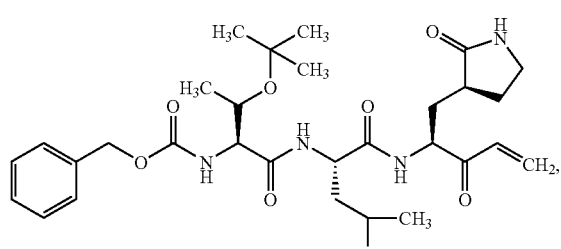
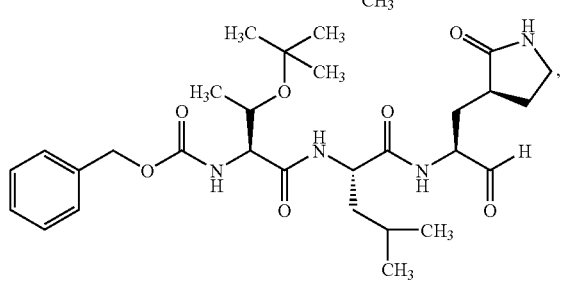
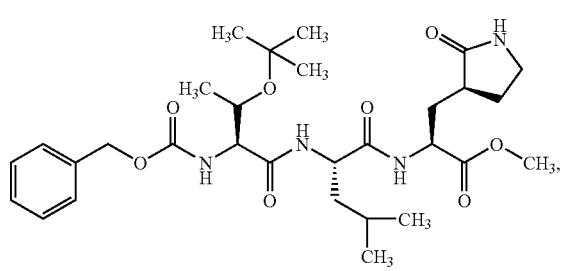
-continued
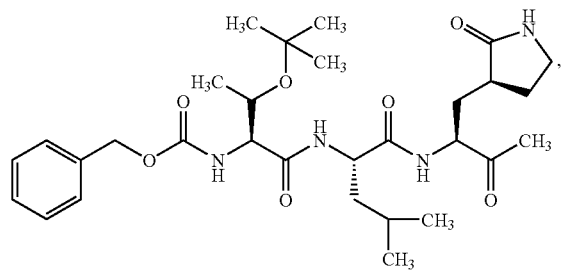
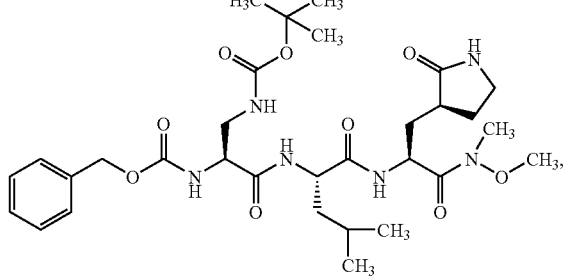
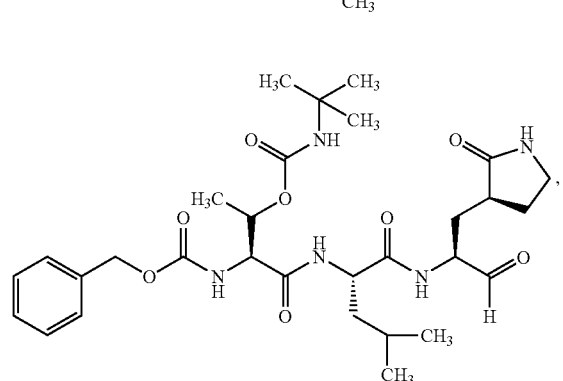
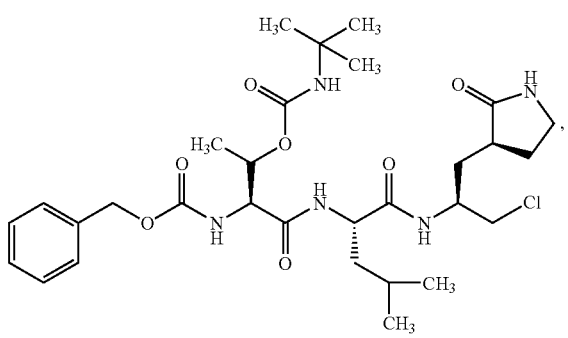
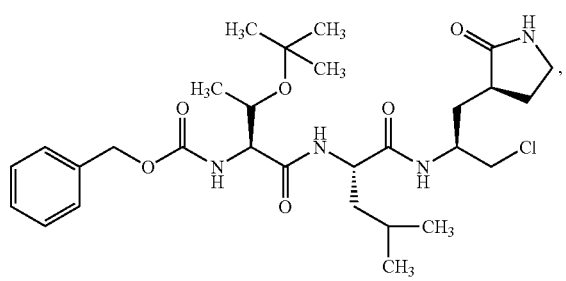

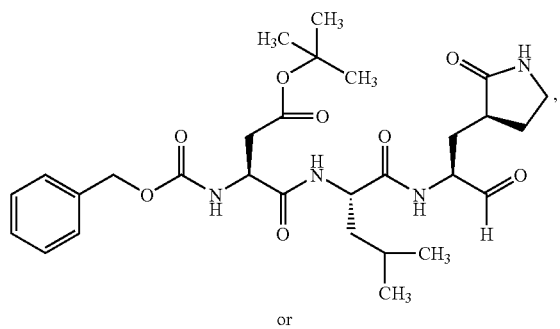
or
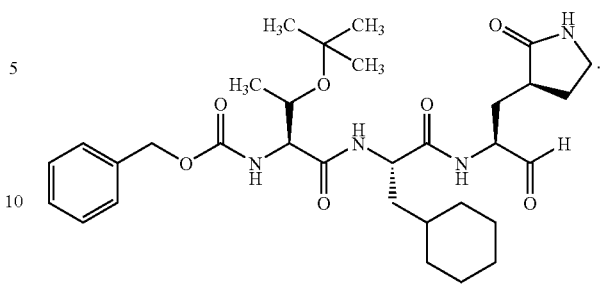
2. A pharmaceutical composition comprising a compound of claim 1 and a pharmaceutically acceptable carrier.
* * * * *